US012279840B2

(12) United States Patent
Denzinger et al.

(10) Patent No.: US 12,279,840 B2
(45) Date of Patent: Apr. 22, 2025

(54) SELECTABLE JAW CLOSURE OF A ROBOTIC SURGICAL SYSTEM

(71) Applicant: Cilag GmbH International, Zug (CH)

(72) Inventors: Christopher A. Denzinger, Cincinnati, OH (US); Mark D. Overmyer, Cincinnati, OH (US); Charles J. Scheib, Loveland, OH (US); Neil T. Markwardt, Redwood City, CA (US); Brian D. Black, Loveland, OH (US)

(73) Assignee: Cilag GmbH International, Zug (CH)

( * ) Notice: Subject to any disclaimer, the term of this patent is extended or adjusted under 35 U.S.C. 154(b) by 965 days.

(21) Appl. No.: 17/245,111

(22) Filed: Apr. 30, 2021

(65) Prior Publication Data
US 2022/0346890 A1 Nov. 3, 2022

(51) Int. Cl.
*A61B 34/30* (2016.01)
*A61B 17/29* (2006.01)
*B25J 15/00* (2006.01)
*B25J 18/02* (2006.01)

(52) U.S. Cl.
CPC ........... *A61B 34/30* (2016.02); *B25J 15/0028* (2013.01); *B25J 18/025* (2013.01); *A61B 2017/2936* (2013.01)

(58) Field of Classification Search
None
See application file for complete search history.

(56) References Cited

U.S. PATENT DOCUMENTS

| | | | |
|---|---|---|---|
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,210,411 B2 | 7/2012 | Yates et al. |
| 8,408,439 B2 | 4/2013 | Huang et al. |
| 8,453,914 B2 | 6/2013 | Laurent et al. |
| 8,663,220 B2 | 3/2014 | Wiener et al. |
| 9,186,142 B2 | 11/2015 | Fanelli et al. |
| 9,517,065 B2 | 12/2016 | Simms et al. |

(Continued)

OTHER PUBLICATIONS

U.S. Appl. No. 17/245,100.

(Continued)

*Primary Examiner* — Martin T Ton
(74) *Attorney, Agent, or Firm* — Frost Brown Todd LLP

(57) ABSTRACT

A surgical instrument includes an end effector, a shaft assembly, a drive, and an activating mechanism. The end effector includes first and second jaws. At least one of the first and second jaws is pivotable relative to the other of the first and second jaws between open and closed positions. The shaft assembly extends proximally from the end effector. The drive is operatively connected to a portion of at least one of the end effector or the shaft assembly. The activating mechanism includes an actuation body operatively connected to the drive. The portion is configured to perform a first actuation profile in response to the actuation body moving along a first predetermined path or perform a second actuation profile in response to the actuation body moving along a second predetermined path. Selection of the first predetermined path is configured to prevent the actuation body from accessing the second predetermined path.

20 Claims, 29 Drawing Sheets

(56) References Cited

U.S. PATENT DOCUMENTS

| | | | |
|---|---|---|---|
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,949,785 | B2 | 4/2018 | Price et al. |
| 10,092,292 | B2 | 10/2018 | Boudreaux et al. |
| 10,349,939 | B2 | 7/2019 | Shelton, IV et al. |
| 2006/0079874 | A1 | 4/2006 | Faller et al. |
| 2007/0191713 | A1 | 8/2007 | Eichmann et al. |
| 2008/0200940 | A1 | 8/2008 | Eichmann et al. |
| 2015/0313676 | A1* | 11/2015 | Deodhar ............... A61B 34/30 606/130 |
| 2015/0327850 | A1* | 11/2015 | Kostrzewski .... A61B 17/07207 74/57 |
| 2017/0281189 | A1* | 10/2017 | Nalagatla ............ A61B 17/115 |
| 2019/0209158 | A1* | 7/2019 | Felix .................... A61B 17/068 |
| 2021/0393340 | A1 | 12/2021 | Beckman et al. |

OTHER PUBLICATIONS

U.S. Appl. No. 17/245,332.

U.S. Appl. No. 17/245,351.

U.S. Appl. No. 17/022,520, entitled "Method of Applying Buttress to End Effector of Surgical Stapler," filed Sep. 19, 2020.

U.S. Appl. No. 17/077,067, entitled "Surgical Instrument and Carrier KART Supporting Ultrasonic Transducer," filed Oct. 22, 2020.

U.S. Appl. No. 17/077,086, entitled "Carrier KART and Jaw Closure of an Ultrasonic Surgical Instrument," filed Oct. 22, 2020.

U.S. Appl. No. 17/076,956, entitled "Surgical Instrument with an Articulatable Shaft Assembly and Dual End Effector Role," filed Oct. 22, 2020.

U.S. Appl. No. 17/076,959, entitled "Ultrasonic Surgical Instrument with a Distally Grounded Acoustic Wave," filed Oct. 22, 2020.

U.S. Appl. No. 17/077,098, entitled "Ultrasonic Surgical Instrument with a Multiplanar Articulation Joint," filed Oct. 22, 2020.

U.S. Appl. No. 17/077,110, entitled "Ultrasonic Surgical Instrument with a Mid-Shaft Closure System and Related Methods," filed Oct. 22, 2020.

U.S. Appl. No. 17/077,130, entitled "Surgical Instrument with Clamping Sensor Feedback and Related Methods," filed Oct. 22, 2020.

U.S. Appl. No. 17/077,136, entitled "Surgical Instrument with Non-Clamping Sensor Feedback and Related Methods," filed Oct. 22, 2020.

U.S. Appl. No. 17/077,139, entitled "Ultrasonic Surgical Instrument with a Fixed Transducer Grounding," filed Oct. 22, 2020.

U.S. Appl. No. 17/077,146, entitled "Ultrasonic Surgical Instrument with a Shaft Assembly and Elongated Waveguide Support Arrangement," filed Oct. 22, 2020.

U.S. Appl. No. 17/077,152, entitled "Damping Rings for an Ultrasonic Surgical Instrument," filed Oct. 22, 2020.

U.S. Appl. No. 17/077,250, entitled "Ultrasonic Surgical Instrument with a Carrier KART and Reusable Stage," filed Oct. 22, 2020.

U.S. Appl. No. 17/077,373, entitled "Surgical Instrument with a Carrier KART and Various Communication Cable Arrangements," filed Oct. 22, 2020.

U.S. Appl. No. 17/245,100, entitled "Translatable Barrel Cam of a Robotic Surgical System," filed Apr. 30, 2021.

U.S. Appl. No. 17/245,111, entitled "Selectable Jaw Closure of a Robotic Surgical System," filed Apr. 30, 2021.

U.S. Appl. No. 17/245,332, entitled "Variable Jaw Closure of a Robotic Surgical System," filed Apr. 30, 2021.

U.S. Appl. No. 17/245,351, entitled "Multi-Zone Jaw Closure of a Robotic Surgical System," filed Apr. 30, 2021.

\* cited by examiner

SELECTABLE JAW CLOSURE OF A ROBOTIC SURGICAL SYSTEM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

Additional examples of such surgical instruments include an ultrasonic surgical instrument with end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned; U.S. Pub. No. 2007/0191713, entitled "Ultrasonic Device for Cutting and Coagulating," published Aug. 16, 2007, now abandoned; U.S. Pub. No. 2008/0200940, entitled "Ultrasonic Device for Cutting and Coagulating," published Aug. 21, 2008, now abandoned, U.S. Pat. No. 9,949,785, entitled "Ultrasonic Surgical Instrument with Electrosurgical Feature," issued Apr. 24, 2018; and U.S. Pat. No. 8,663,220, entitled "Ultrasonic Surgical Instruments," issued Mar. 4, 2014. The disclosure of each of the above-cited U.S. Patent Publications and U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
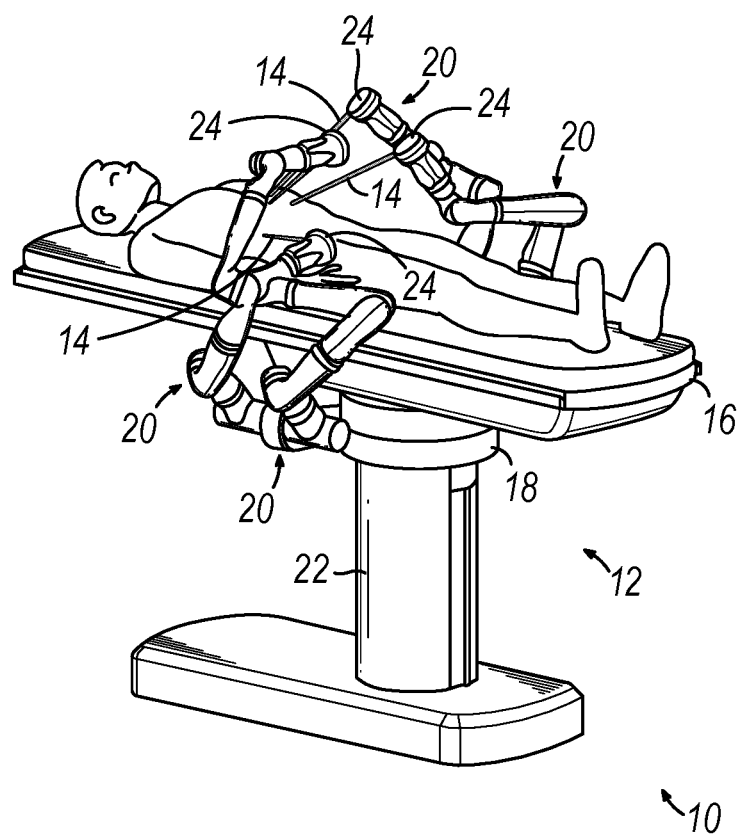
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "longitudinal," "inner," "outer," and "upper," also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. EXEMPLARY ROBOTICALLY-ENABLED MEDICAL SYSTEM

FIG. 1 shows an exemplary robotically-enabled medical system, including a first example of a table-based robotic system (10). Table-based robotic system (10) of the present example includes a table system (12) operatively connected to a surgical instrument (14) for a diagnostic and/or therapeutic procedure in the course of treating a patient. Such procedures may include, but are not limited, to bronchoscopy, ureteroscopy, a vascular procedure, and a laparoscopic procedure. To this end, surgical instrument (14) is configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
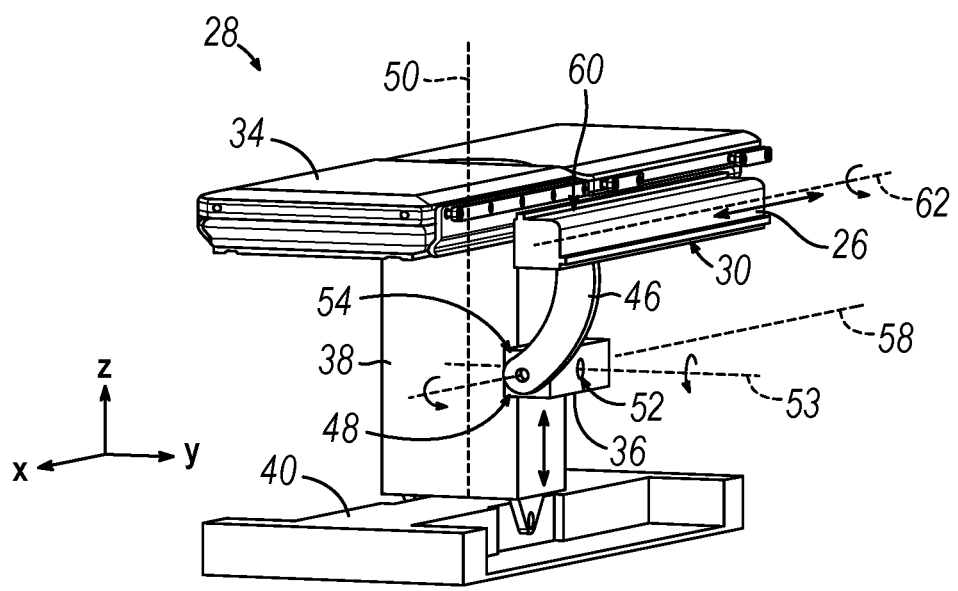
FIG. 2 depicts a perspective view of a second example of a table-based robotic system.
Figure 3:
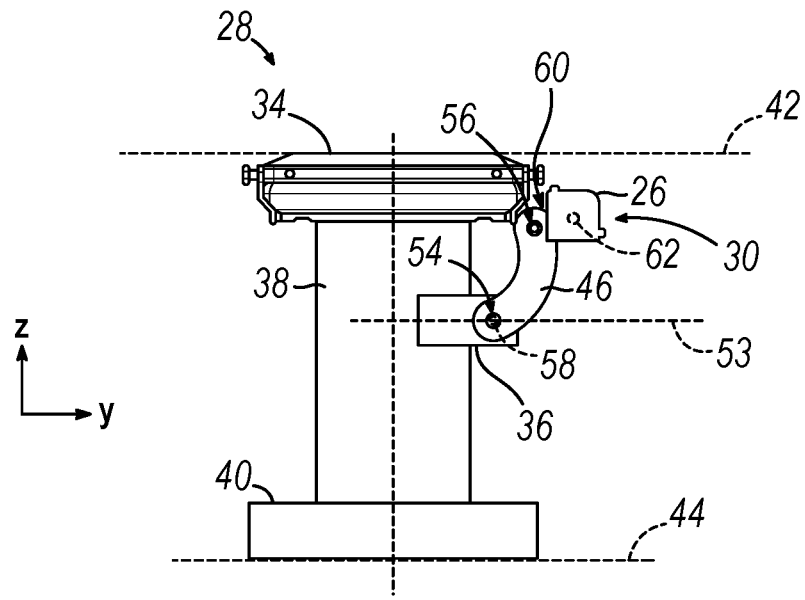
FIG. 3 depicts an end elevational view of the table-based robotic system of FIG. 2.
Figure 4:
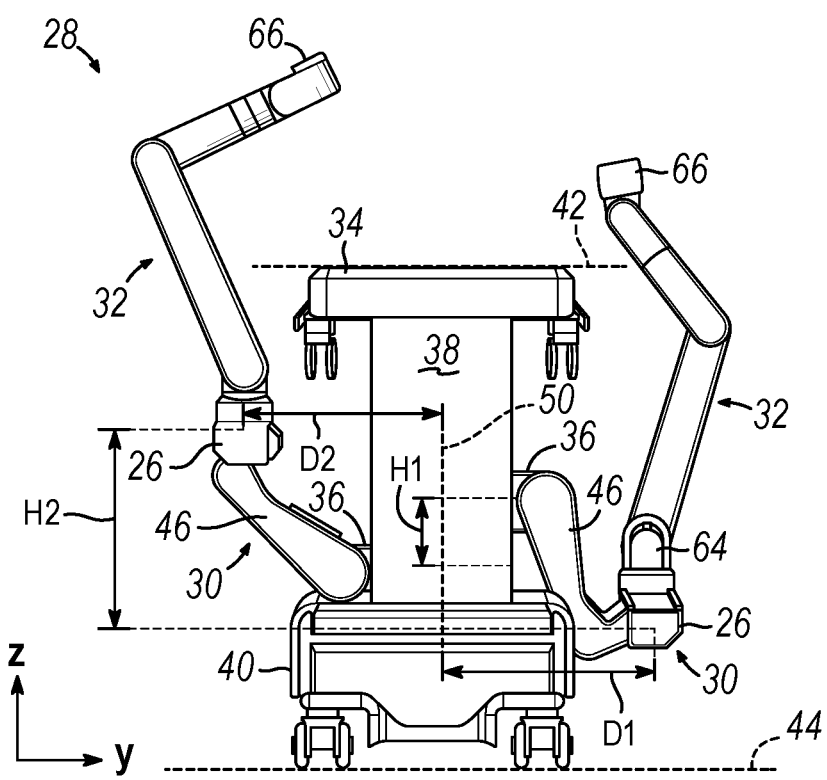
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as surgical instrument (14) (see FIG. 6A), the instrument includes an instrument-based insertion architecture.

Figure 5:
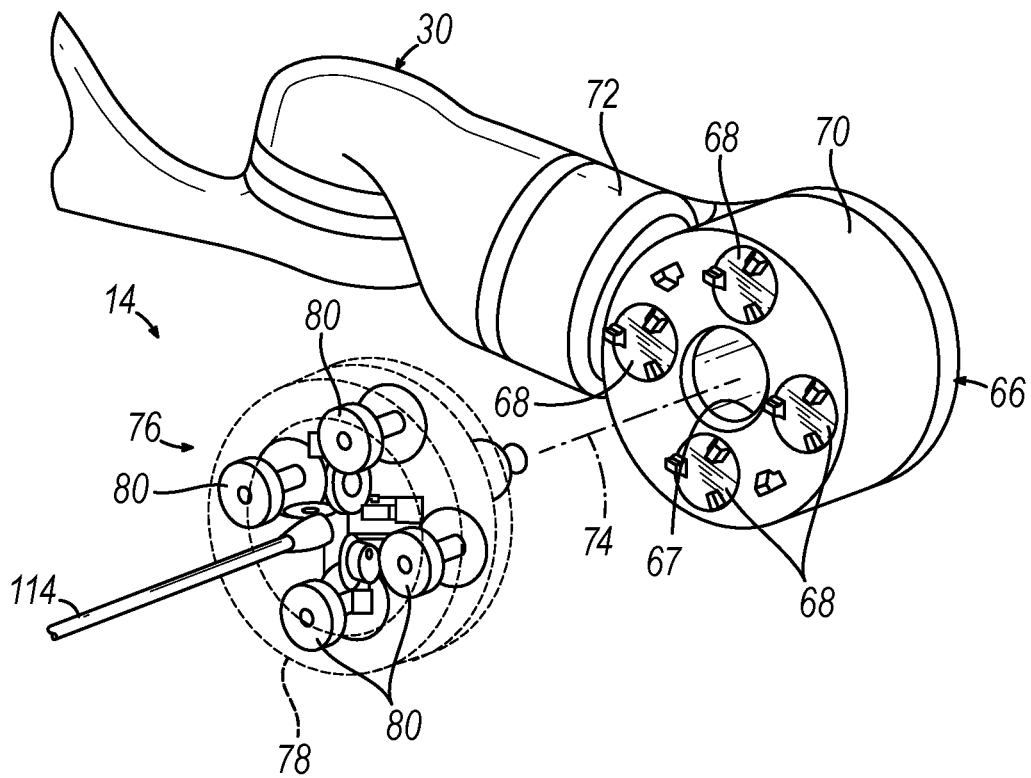
FIG. 5 depicts a partially exploded perspective view of the robotic arm of FIG. 4 having an instrument driver and a first exemplary surgical instrument.

FIG. 5 shows one example of instrument driver (66) in greater detail with surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. Exemplary Surgical Instrument

Figure 6A:
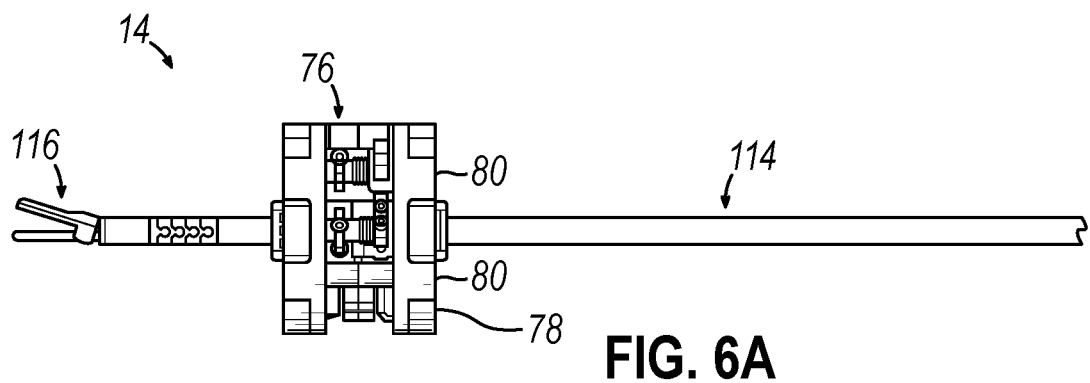
FIG. 6A depicts a side elevational view of the surgical instrument of FIG. 5 in a retracted position.
Figure 6B:
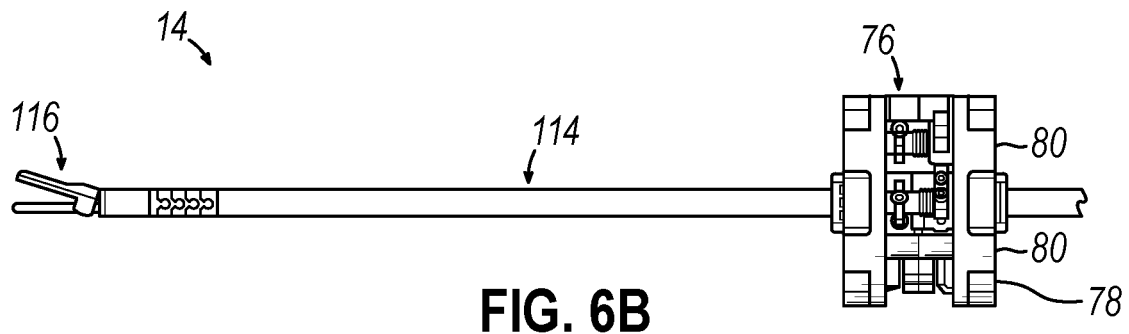
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of instrument base (76) with an axis substantially parallel to the axes of the drive inputs (80) as discussed briefly above. With shaft assembly (114) positioned at the center of instrument base (76), shaft assembly (114) is coaxial with instrument driver axis (74) when attached and movably received in clearance bore (67). Thus, rotation of rotational assembly (70) causes shaft assembly (114) of surgical instrument (14) to rotate about its own longitudinal axis while clearance bore (67) provides space for translation of shaft assembly (114) during use.

To this end, FIGS. 5-6B show surgical instrument (14) having the instrument-based insertion architecture as discussed briefly above. Surgical instrument (14) includes elongated shaft assembly (114), end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriages, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

II. EXEMPLARY SURGICAL STAPLER

In some instances, it may be desirable to use various alternative surgical instruments with robotic systems (10, 28) described above in addition to, or in lieu of, surgical instrument (14). Such alternative surgical instruments may be desirable to provide improved operability when used with robotic systems (10, 28). For instance, as described above, surgical instrument (14) may move between a retracted position and extended position. Additionally, it may be beneficial to translate a portion of surgical instrument (14) along a support structure to provide increased surgical access without increasing the dimensions of surgical instrument (14). As also described above, use of rotational assembly (70) of robotic arm (20, 32) may enable rotation of the entire surgical instrument (14), rather than specific structures of surgical instrument (14) being rotatable.

One such example of these alternative surgical instruments includes a second exemplary surgical instrument (210), which may also be referred to as surgical stapler (210) and is discussed below in greater detail. Additional examples of alternative surgical instruments and/or associated features for incorporation with robotic systems (10, 28) are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024; U.S. patent application Ser. No. 17/077,067, entitled "Surgical Instrument and Carrier KART Supporting Ultrasonic Transducer," filed on Oct. 22, 2020, issued as U.S. Pat. No. 12,035,935 on Jul. 16, 2024; U.S. patent application Ser. No. 17/077,086, entitled "Carrier KART and Jaw Closure of an Ultrasonic Surgical Instrument," filed on Oct. 22, 2020, issued as U.S. Pat. No. 12,016,587 on Jun. 25, 2024; U.S. patent application Ser. No. 17/077,130, entitled "Surgical Instrument with Clamping Sensor Feedback and Related Methods," filed on Oct. 22, 2020, published as U.S. Pat. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, issued as U.S. Pat. No. 11,950,798 on Apr. 9, 2024; U.S. patent application Ser. No. 17/077,250, entitled "Ultrasonic Surgical Instrument with a Carrier KART and Reusable Stage," filed on Oct. 22, 2020, issued as U.S. Pat. No. 11,998,228 on Jun. 4, 2024; U.S. patent application Ser. No. 17/077,373, entitled "Surgical Instrument with a Carrier KART and Various Communication Cable Arrangements," filed on Oct. 22, 2020, issued as U.S. Pat. No. 11,931,059 on Mar. 19, 2024; U.S. patent application Ser. No. 17/077,139, entitled "Ultrasonic Surgical Instrument with a Fixed Transducer Grounding," filed on Oct. 22, 2020, published as U.S. Pat. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pat. Pub. No. 2022/0125460 on Apr. 28, 2022; U.S. patent application Ser. No. 17/077,152, entitled "Damping Rings for an Ultrasonic Surgical Instrument," filed on Oct. 22, 2020, issued as U.S. Pat. No. 11,806,037 on Nov. 7, 2023; U.S. patent application Ser. No. 17/077,110, entitled "Ultrasonic Surgical Instrument with a Mid-shaft Closure System and Related Methods," filed on Oct. 22, 2020, issued as U.S. Pat. No. 11,944,341 on Apr. 2, 2024; U.S. patent application Ser. No. 17/076,956, entitled "Surgical Instrument with an Articulatable Shaft Assembly and Dual End Effector Roll," filed on Oct. 22, 2020, issued as U.S. Pat. No. 11,890,030 on Feb. 6, 2024; U.S. patent application Ser. No. 17/076,959, entitled "Ultrasonic Surgical Instrument with a Distally Grounded Acoustic Waveguide," filed on Oct. 22, 2020, issued as U.S. Pat. No. 11,998,227 on Jun. 4, 2024; and/or U.S. patent application Ser. No. 17/077,098, entitled "Ultrasonic Surgical Instrument with a Multiplanar Articulation Joint," filed on Oct. 22, 2020, published as U.S. Pat. Pub. No. 2022/0125467 on Apr. 28, 2022, which is now abandoned. The disclosure of each of the above-cited U.S. Patent Applications is incorporated by reference herein in its entirety. Various features of these alternative examples of surgical instruments may be readily incorporated into a surgical robotic system, such as robotic systems (10, 28), such that the invention is not intended to be unnecessarily limited to these particular alternative surgical instruments discussed herein.

A. Overview

Figure 7:
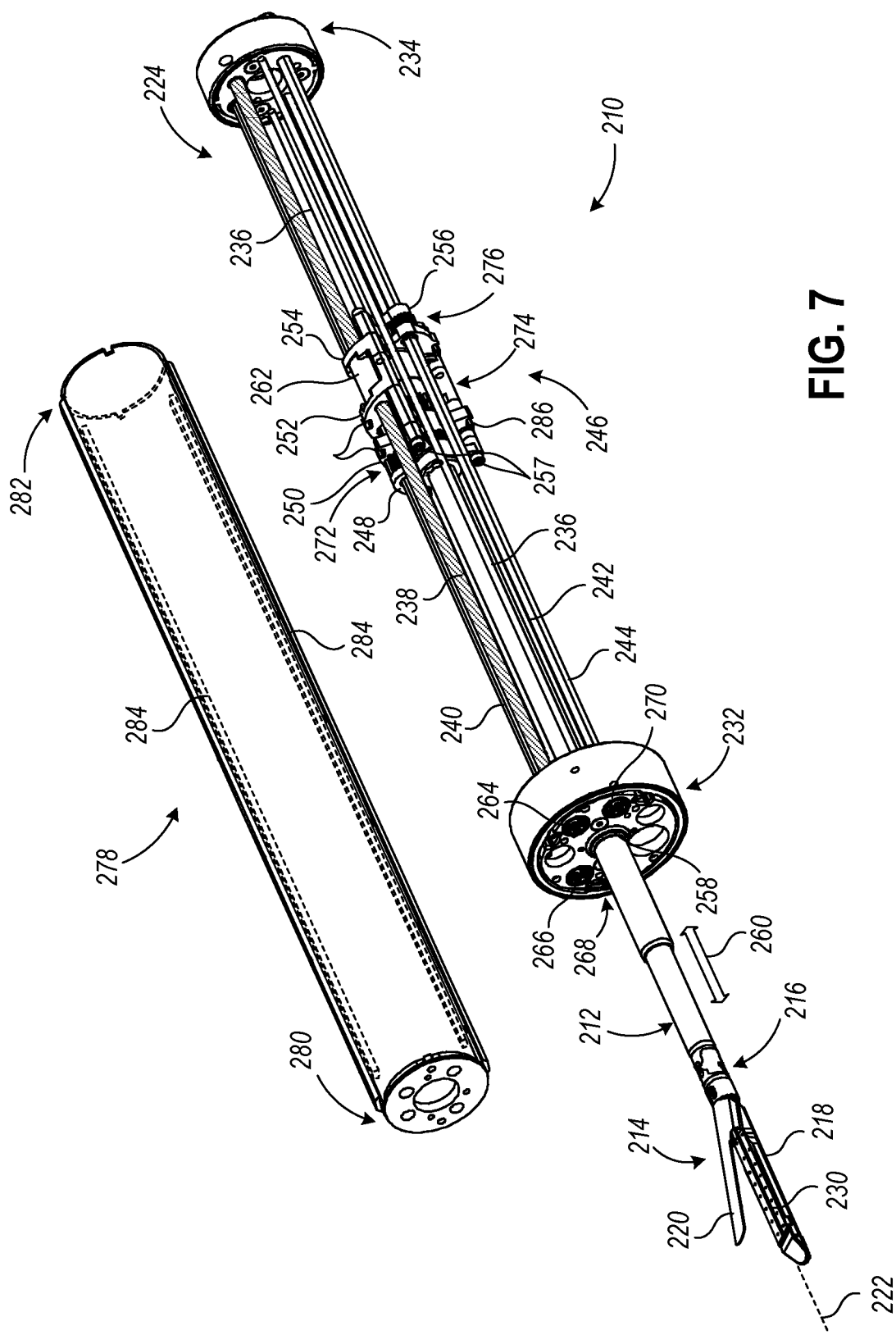
FIG. 7 depicts a perspective view of a second exemplary surgical instrument having a first example of a carriage operatively connected to an end effector configured for cutting and sealing transected tissue with a plurality of staples.

FIG. 7 is an exemplary surgical instrument (210) that may incorporate some or all of the principles of the present disclosure. Surgical instrument (210) may be similar in some respects to any of the instruments described above with reference to FIGS. 1-6B and, therefore, may be used in conjunction with a robotic surgical system, such as robotic systems (10, 28) of FIGS. 1-6B. As illustrated, surgical instrument (210) includes an elongated shaft (212), an end effector (214) arranged at a distal end of shaft (212), and an articulable wrist (216), which may also be referred to herein as a "wrist joint," that interposes and couples end effector (214) to the distal end of shaft (212).

Surgical instrument (210) can have any of a variety of configurations capable of performing one or more surgical functions. In the present example, end effector (214) comprises a surgical stapler, which may also be referred to herein as an "endocutter," configured to cut and staple tissue for fastening. As illustrated, end effector (214) includes opposing jaws (218, 220) configured to move, which may also be referred to as "articulate," between open and closed positions. Alternatively, end effector (214) may comprise other types of instruments requiring opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In another example, end effector (214) may instead comprise any end effector or instrument capable of being operated in conjunction with a robotic system, such as robotic systems (10, 28), and related methods. Such end effectors, and more generally instruments, include, but are not limited to, a suction irrigator, an endoscope (e.g., a camera), an ultrasonic instrument, an RF instrument, or any combination thereof.

One or both of jaws (218, 220) may be configured to pivot and actuate end effector (214) between open and closed positions. In the illustrated example, upper jaw (220) is rotatable, and more particularly pivotable, relative to lower jaw (218) to move between an open, unclamped position and a closed, clamped position. In other examples, however, lower jaw (218) may move relative to upper jaw (220). In still other examples, both lower and upper jaws (218, 220) may move to actuate end effector (214) between open and closed positions.

In the present example, lower jaw (218) is referred to as a "cartridge" or "channel" jaw, and upper jaw (220) is referred to as an "anvil" jaw. Lower jaw (218) may include a frame that houses or supports a staple cartridge, and upper jaw (220) is pivotally supported relative to upper jaw (220) and defines a surface that operates as an anvil to deform staples ejected from the staple cartridge during operation.

Wrist (216) enables end effector (214) to pivot relative to shaft (212) and thereby position end effector (214) at various desired orientations and locations relative to a surgical site. In the present example, wrist (216) is configured such that end effector (214) pivots laterally left and laterally right relative to a longitudinal axis (222) of shaft (212). In other examples, wrist (216) may alternatively provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a robotic surgical system (e.g., end effector (214)) with respect to a given reference Cartesian frame. As used herein, "surge" refers to forward and backward translational movement, "heave" refers to translational movement up and down, and "sway" refers to translational movement left and right. With regard to rotational terms, "roll" refers to tilting side to side, "pitch" refers to tilting forward and backward, and "yaw" refers to turning left and right.

Still referring to FIG. 7, surgical instrument (210) includes a drive housing (224) that houses an actuation system designed to facilitate articulation of wrist (216) and actuation of end effector (214) (e.g., clamping, firing, rotation, articulation, energy delivery, etc.). Drive housing (224), alternately referred to as a "stage," provides various coupling features that releasably couple surgical instrument (210) to an instrument driver of a robotic surgical system. Drive housing (224) includes a plurality of drive members (226, 228) (see FIG. 8A) that extend to wrist (216) and end effector (214). Selective actuation of one or more of drive members (226, 228) causes end effector (214) to pivot relative to shaft (212) at wrist (216). Selective actuation of one or more other drive members (not shown) causes end effector (214) to actuate, such as by closing and/or opening jaws (218, 220) and thereby enabling end effector (214) to clamp tissue. Once tissue is clamped between opposing jaws (218, 220), actuating end effector (214) may further include "firing" end effector (214), which may refer to causing a cutting element (not shown), such as a knife, to distally advance within a slot (230) defined in lower jaw (218). While moving distally, cutting element (not shown) transects tissue clamped between opposing jaws (218, 220). Moreover, as cutting element (not shown) advances, a plurality of staples (not shown) contained within staple cartridge (e.g., housed within lower jaw (218)) are urged into deforming contact with corresponding anvil surfaces, such as pockets, provided on upper jaw (220). In one example, the deployed staples may form multiple rows of staples configured to seal opposing sides of the transected tissue.

Drive housing (224) has a distal end (232) and an opposing, proximal end (234). Distal end (232) may also be referred to herein as a "handle." In some examples, one or more struts (236), such as two such struts (236), extend longitudinally between the distal and proximal ends (232, 234) to fix a distance between distal and proximal ends (232, 234), provide structural stability to drive housing (224), and secure distal end (232) relative to proximal end (234).

Drive housing (224) also includes a lead screw (238) and one or more splines (240, 242, 244), which also extend longitudinally between the distal and proximal ends (232, 234). In the present example, drive housing (224) includes a first spline (240), a second spline (242), and a third spline (244). While three splines (240, 242, 244) are depicted in the drive housing (224), more or less than three such splines (240, 242, 244) may be included in an alternative drive housing (224) in another example. Unlike struts (236), lead screw (238) and splines (240, 242, 244) are rotatably mounted to distal and proximal ends (232, 234). To this end, selective rotation of lead screw (238) and splines (240, 242, 244) causes various functions of drive housing (224) to transpire, such as translating end effector (214) along longitudinal axis (222), pivoting end effector (214) at wrist (216), opening or closing jaws (218, 220), and/or firing end effector (214).

Drive housing (224) further includes a carriage (246) movably mounted along lead screw (238) and splines (240, 242, 244) and houses various activating mechanisms configured to cause operation of specific functions of end effector (214). Carriage (246) may comprise two or more layers, shown in the present example as a first layer (248), a second layer (250), a third layer (252), a fourth layer (254), and a fifth layer (256). Lead screw (238) and splines (240, 242, 244) each extend through portions of one or more of layers (248, 250, 252, 254, 256) to allow carriage (246) to translate along longitudinal axis (222) with respect to lead screw (238) and splines (240, 242, 244). In some examples, layers (248, 250, 252, 254, 256) may be secured to each other in series using one or more mechanical fasteners (257) extending between first layer (248) and fifth layer (256) and through coaxially aligned holes defined in some or all of layers (248, 250, 252, 254, 256). While five layers (248, 250, 252, 254, 256) are shown in the present example, more or less than five such layers may be included in an alternative carriage (246) such that the invention is not intended to be unnecessarily limited to five layers (248, 250, 252, 254, 256).

Shaft (212) is coupled to and distally extends from carriage (246) through a central aperture (258) in distal end (232). Carriage (246) is movable between distal and proximal ends (232, 234) along longitudinal axis (222) and is thereby able to advance or retract end effector (214) relative to drive housing (224), as indicated by the arrows (260). More specifically, in some examples, carriage (246) includes a carriage nut (262) mounted to lead screw (238) and secured between third and fourth layers (252, 254). The outer surface of lead screw (238) defines outer helical threading and carriage nut (262) defines corresponding internal helical threading configured to be received within outer helical threading. As a result, rotation of lead screw (238) causes carriage nut (262) to advance or retract carriage (246) along longitudinal axis (222) and correspondingly advance or retract end effector (214) relative to drive housing (224).

As indicated above, lead screw (238) and splines (240, 242, 244) are rotatably mounted to distal and proximal ends (232, 234). More specifically, distal end (232) of drive housing (224) may include one or more rotatable drive inputs actuatable to independently rotate lead screw (238) and splines (240, 242, 244). In the present example, drive housing (224) includes a first drive input (264), a second drive input (266), a third drive input (268), and a fourth drive input (270). As described below, each drive input (264, 266, 268, 270) may be matable with a corresponding drive output of an instrument driver such that rotation of a given drive output correspondingly rotates the associated drive input (264, 266, 268, 270) and thereby rotates the mated lead screw (238) or spline (240, 242, 244). While four drive inputs (264, 266, 268, 270) are shown in the present example, more or less than four may be included in an alternative drive housing such that the invention is not intended to be unnecessarily limited to four such drive inputs (264, 266, 268, 270).

First drive input (264) as shown is operatively coupled to lead screw (238) such that rotation of first drive input (264) correspondingly rotates lead screw (238), which causes carriage nut (262) and carriage (246) to advance or retract along longitudinal axis (222), depending on the rotational direction of lead screw (238). Second drive input (266) as shown is operatively coupled to first spline (240) such that rotation of second drive input (266) correspondingly rotates first spline (240). In one example, first spline (240) is operatively coupled to a first activating mechanism (272) of carriage (246), and first activating mechanism (272), in turn, is operable to open and close jaws (218, 220). Third drive input (268) as shown is operatively coupled to second spline (242) such that rotation of third drive input (268) correspondingly rotates second spline (242). In one example, second spline (242) is operatively coupled to a second activating mechanism (274) of carriage (246), and second activating mechanism (274) is operable to articulate end effector (214) at wrist (216). Fourth drive input (270) as shown is operatively coupled to third spline (244) such that rotation of fourth drive input (270) correspondingly rotates third spline (244). In one example, third spline (244) is operatively coupled to a third activating mechanism (276) of carriage (246), and third activating mechanism (276) is operable to fire cutting element (not shown) of end effector (214).

Drive housing (224) of the present example also includes a shroud (278) sized to receive and otherwise surround carriage (246), lead screw (238), and splines (240, 242, 244). Shroud (278) comprises a tubular structure having a distal end (280) matable with distal end (232) of drive housing (224), and a proximal end (282) matable with proximal end (234) of drive housing (224). Rails (284) extend longitudinally and parallel to lead screw (238) and are sized to be received within corresponding notches (286) defined on an outer periphery of carriage (246) and, more particularly, on the outer periphery of one or more of carriage layers (248, 250, 252, 254, 256). As carriage (246) translates along longitudinal axis (222), rails (284) are configured to maintain an angular position of carriage (246) and bear any torsional loading that may otherwise adversely affect movement and/or operation of carriage (246) during use.

Figure 8A:
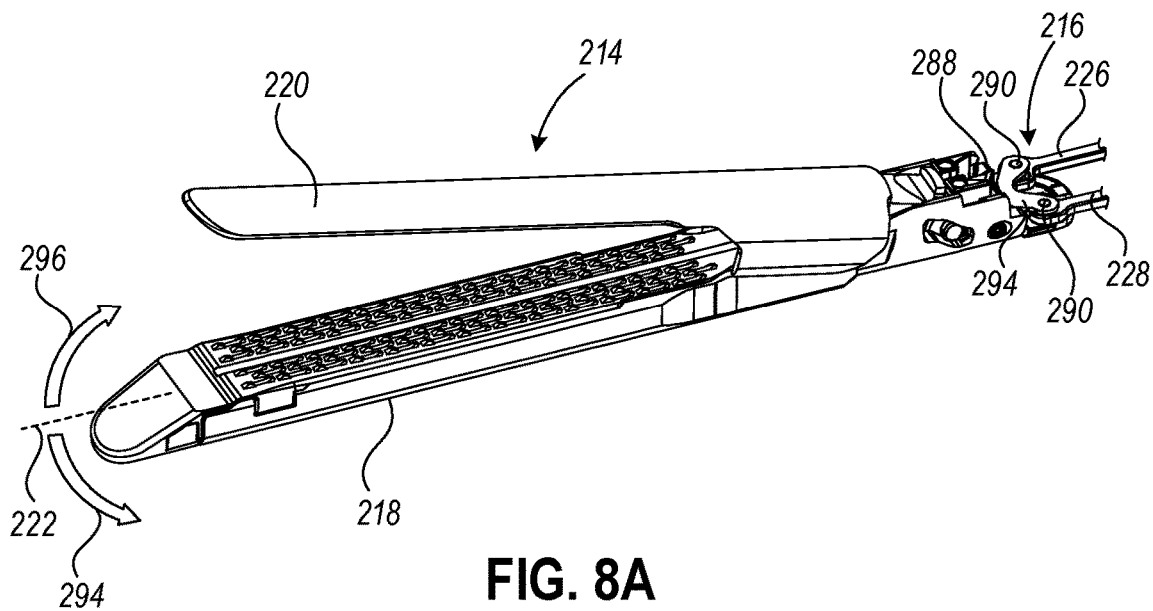
FIG. 8A depicts an enlarged perspective view of the end effector of FIG. 7 showing a wrist configured to articulate the end effector.

As shown in FIG. 8A, wrist (216) more particularly has drive members (226, 228) interconnected with end effector (214) and configured to articulate end effector (214) relative to longitudinal axis (222). End effector (214) is mounted to an end effector mount (288) having two articulation pins (290), and a distal end of each drive member (226, 228) is rotatably mounted to a corresponding one of articulation pins (290). Drive members (226, 228) are also interconnected at distal ends via a distal link (292), which together comprise a linkage configured to support articulation of end effector mount (288) and, in turn, articulation of end effector (214).

Drive members (226, 228) translate antagonistically and parallel along longitudinal axis (222), such that as first drive member (226) moves distally second drive member (228) moves proximally, and vice versa. Moreover, distal movement of first drive member (226) and simultaneous proximal movement of second drive member (228) cooperatively act on end effector mount (288) to cause end effector (214) to rotate counterclockwise, as indicated by an arrow (294). In contrast, proximal movement of first drive member (226) and simultaneous distal movement of second drive member (228) cooperatively act on end effector mount (288) to cause end effector (214) to rotate clockwise, as indicated by an arrow (296).

Figure 8B:
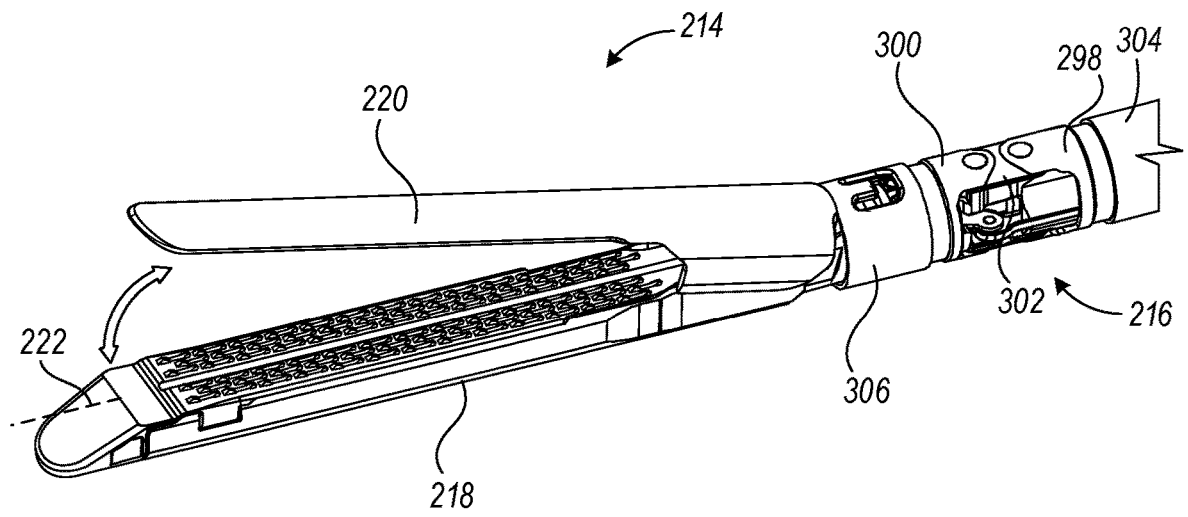
FIG. 8B depicts the enlarged perspective view of the end effector similar to FIG. 8A, but showing an upper jaw configured to selectively move between open and closed positions relative to a lower jaw.

FIG. 8B shows end effector (214) having jaws (218, 220) configured to selectively move between open and closed positions. To this end, wrist (216) has a proximal clevis (298), distal clevis (300), and a closure link (302) configured to operatively couple proximal and distal devises (298, 300) across wrist (216). Proximal clevis (298) of the present example is coupled a distal end of a closure tube (304) whereas distal clevis (300) is coupled to a closure ring (306). Axial movement of closure tube (304) along longitudinal axis (222) correspondingly moves proximal clevis (298) in the same axial direction, and closure link (302) is configured to transmit the axial load through wrist (216) to close jaws (218, 220) of end effector (214). Closure link (302) transmits closure load via translation of closure tube (304) from distal clevis (300) to proximal clevis (298) such that closure ring (306) correspondingly pushes or pulls on upper jaw (220) to open or close upper jaw (220) relative to lower jaw (218) as applicable.

While the above articulation of end effector (214) relative to longitudinal axis (222) and movement of upper jaw (220) between open and closed positions is shown as described herein, it will be appreciated that such articulation and movement may be performed at end effector (214) with alternative structures. The invention is thus not intended to be unnecessarily limited to the particular end effector (214) with associated wrist (216) and shown and described herein.

Figure 9:
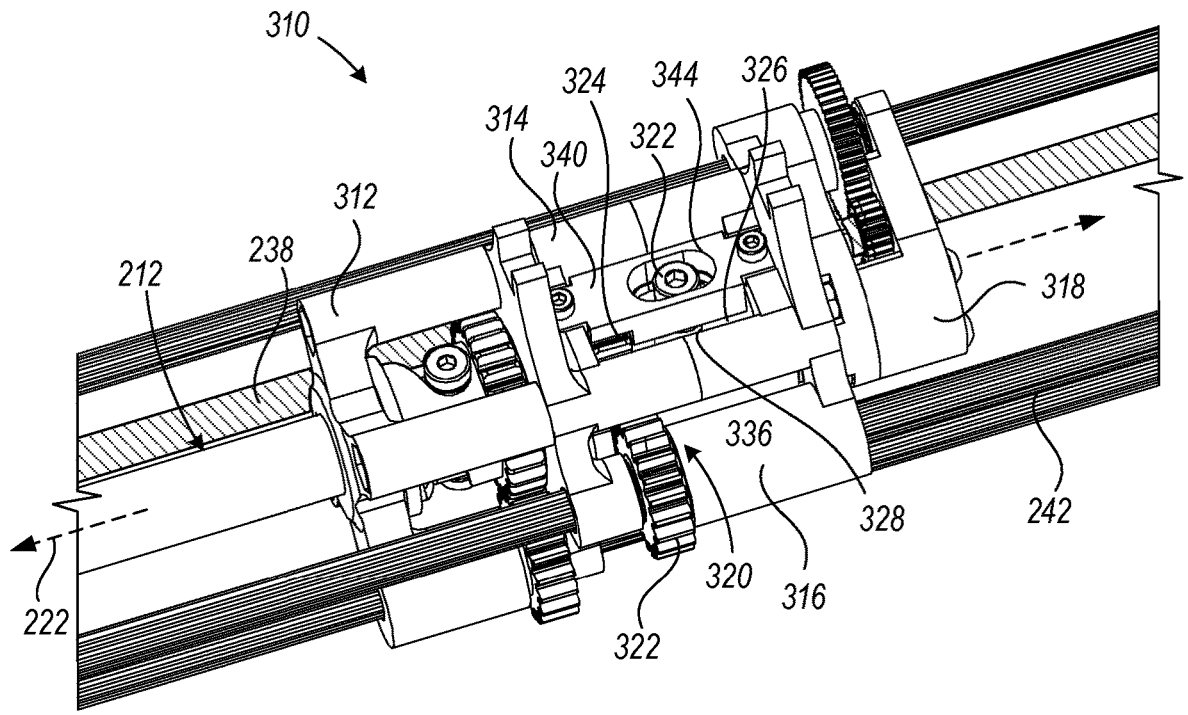
FIG. 9 depicts an enlarged perspective view of a second example of a carriage incorporated into the surgical instrument of FIG. 7 and having an articulation activating mechanism.
Figure 10:
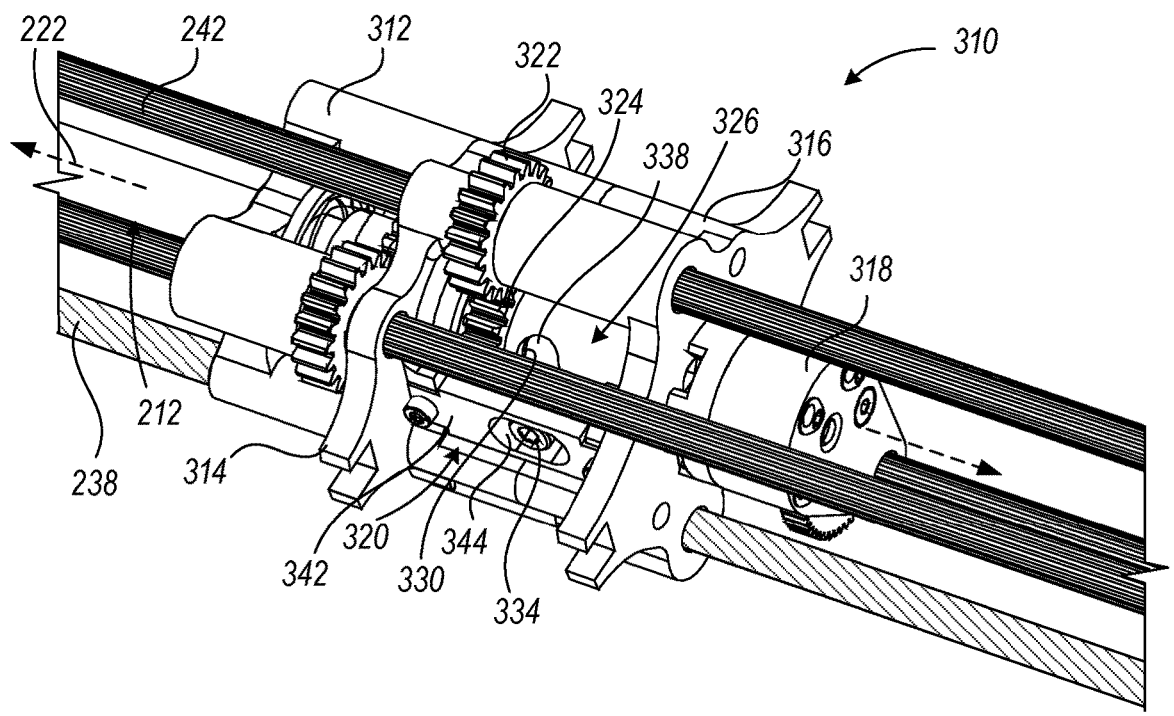
FIG. 10 depicts another enlarged perspective view of the carriage of FIG. 9 incorporated into the surgical instrument of FIG. 7.

B. Activating Mechanisms for Articulation and Jaw Movement i. Articulation Activating Mechanism with Barrel Cam FIGS. 9 and 10 show another example of a carriage (310) similar in some respects to carriage (246) (see FIG. 7) discussed above and may replace carriage (246) (see FIG. 7) in one or more examples such that like numbers below indicate like features discussed above. Carriage (310) is thus like carriage (246) (see FIG. 7) unless noted otherwise below. Carriage (310) more particularly has two or more layers, such as a first layer (312), a second layer (314), a third layer (316), and a fourth layer (318). Shaft (212) is coupled to and extends distally from carriage (310) such that carriage (310) is configured to move along longitudinal axis (222) to correspondingly advance or retract end effector (214) shown in FIG. 8A.

With reference to FIGS. 8A and 9-10, carriage (310) includes an activating mechanism (320) configured to articulate end effector (214) relative to longitudinal axis (222) (see FIG. 8A) at wrist (216). Second spline (242) is operatively coupled to activating mechanism (320) such that rotating second spline (242) correspondingly actuates activating mechanism (320) and thereby causes wrist (216) to articulate. More specifically, a drive gear (322) is included with second spline (242) and positioned to intermesh with a driven gear (324) coupled to an articulation barrel (326). As spline (242) rotates, drive gear (322) drives driven gear (324) and correspondingly rotates articulation barrel (326) about longitudinal axis (222).

Articulation barrel (326) of the present example includes a first cam profile (328) and a second cam profile (330). Activating mechanism (320) further includes a first follower pin (332) and a second follower pin (334). First follower pin (332) extends through first cam profile (328) and is coupled to a first carrier (336), and second follower pin (334) extends through second cam profile (330) and is coupled to a second carrier (338). Each cam profile (328, 330) extends about a circumference of articulation barrel (326) (e.g., in a helical pattern), but cam profiles (328, 330) are defined at opposite angles relative to each other. As drive gear (322) drives driven gear (324), articulation barrel (326) correspondingly rotates about longitudinal axis (222), thus urging follower pins (332, 334) to traverse the oppositely-angled cam profiles (328, 330), respectively. As follower pins (332, 334) traverse cam profiles (328, 330), underlying carriers (336, 338) are urged in equal but opposite axial directions along longitudinal axis (222). Depending on a rotational direction of drive gear (322), carriers (336, 338) may be drawn axially toward each other or moved axially away from each other.

In one or more examples, activating mechanism (320) further includes a first articulation torque bar (340) and a second articulation torque bar (342). Articulation torque bars (340, 342) extend between second and third layers (314, 316) and are secured to each layer (314, 316). Each articulation torque bar (340, 342) defines a slot (344) sized to receive heads of corresponding follower pins (332, 334). During use of activating mechanism (320), articulation torque bars (340, 342) are configured to maintain an axial position of corresponding follower pins (332, 334).

Figure 11:
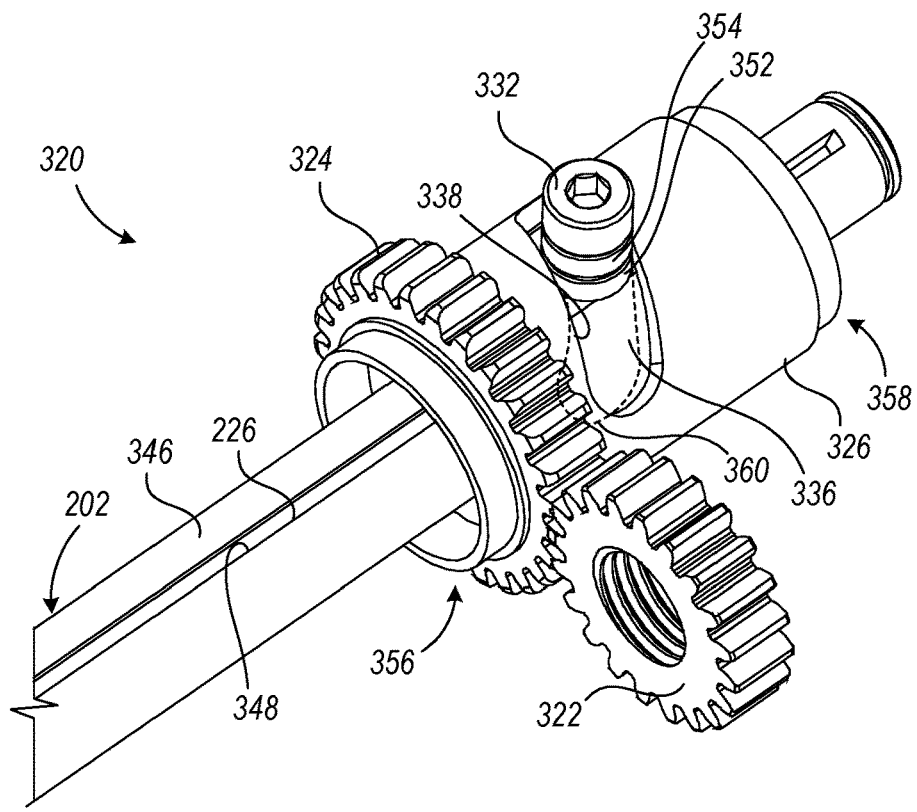
FIG. 11 depicts a perspective view of the articulation activating mechanism of FIG. 9.
Figure 12:
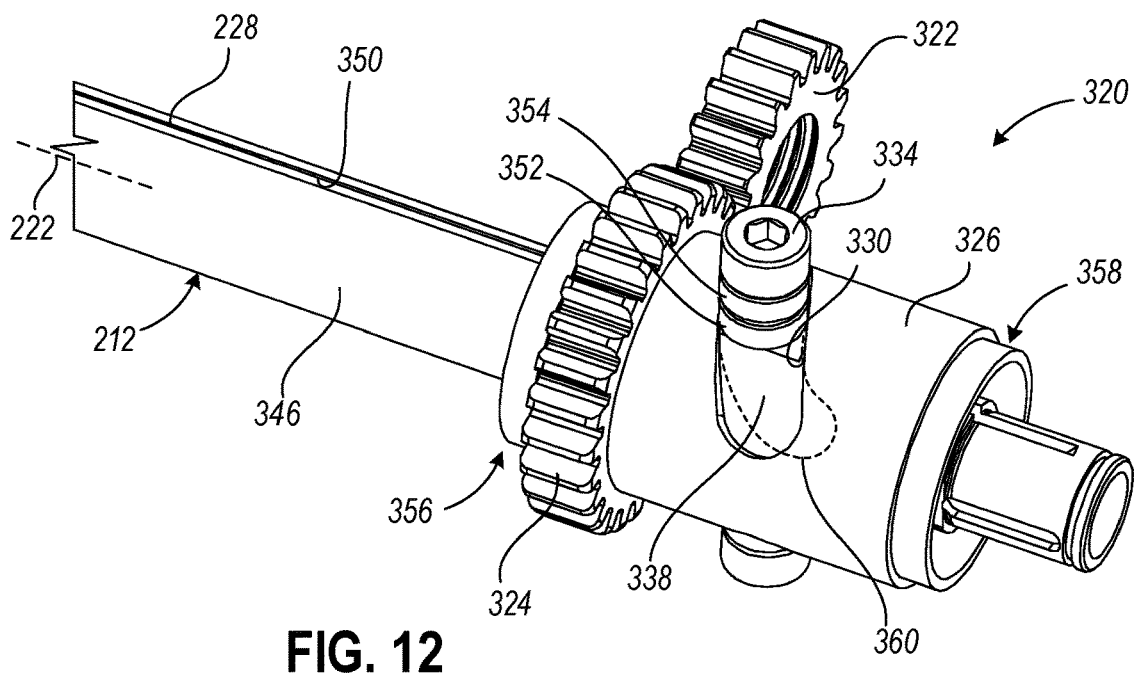
FIG. 12 depicts another perspective view of the articulation activating mechanism of FIG. 9.

FIGS. 11 and 12 more particularly show articulation barrel (326) having a generally cylindrical structure that extends about shaft (212) about an inner grounding shaft (346). First and second carriers (336, 338) interpose inner grounding shaft (346) and articulation barrel (326) and are independently movable along longitudinal axis (222). First carrier (336) is operatively coupled to first drive member (226), which extends distally to wrist (216) (see FIG. 8A) at least partially within a slot (348) defined in inner grounding shaft (346). Additionally, second carrier (338) is operatively coupled to second drive member (228), which extends distally to wrist (216) (see FIG. 8A) at least partially within a slot (350) defined in inner grounding shaft (346).

Follower pins (332, 334) extend through corresponding cam profiles (328, 330) and are coupled to associated carriers (336, 338), respectively. In one example, one or both of follower pins (332, 334) may include bearings, such as a first bearing (352) and a second bearing (354). Such first and second bearings (352, 354) are stacked on top of each other with a shaft of each follower pin (332, 334) extending through first and second bearings (352, 354). First bearings (352) are configured to bear against the inner walls of cam profiles (328, 330) as articulation barrel (326) rotates and follower pins (332, 334) are urged to traverse cam profiles (328, 330) respectively, reducing friction thereagainst. Second bearings (354) are configured to bear against the inner walls of slot (344) (see FIGS. 9-10) defined in corresponding torque articulation bars (340, 342) (see FIGS. 9-10) to prevent rotational movement of follower pins (332, 334) as articulation barrel (326) rotates.

Articulation barrel (326) has a distal end (356) and a proximal end (358), and driven gear (324) may be defined proximate to distal end (356) in one example, provided proximate to proximal end (358) in another example, or alternatively positioned anywhere in between distal and proximal ends (356, 358) in still other examples. Cam profiles (328, 330) are positioned between distal and proximal ends (356, 358) and may comprise straight slots extending at a constant angle about a circumference of articulation barrel (326), but at opposite angular directions. In one example with straight cam profiles (328, 330), movement and force applied to carriers (336, 338) and drive members (226, 228) is constant during articulation of end effector (214) (see FIG. 8A). In such an example, cam profiles (328, 330) may be more particularly described as helical cam slots and follower pins (332, 334) may be more particularly described as linear cam followers.

In another example, cam profiles (328, 330) may not be entirely straight, but may alternatively diverge at one or more inflection points along a length, which may also be referred to as a "path," of cam profile (328, 330). More specifically, cam profiles (328, 330) may diverge from straight and define a more or less aggressive path, such as path (360), depending on a direction at the inflection point. Higher or lower angles of cam profiles (328, 330) alter mechanical advantage obtained as follower pins (332, 334) traverse cam profiles (328, 330) and act on interconnected carriers (336, 338), respectively. Such differing mechanical advantages may be beneficial in one or more uses of articulating end effector (214) relative to longitudinal axis (222).

ii. Jaw Activating Mechanism with Barrel Cam

Figure 13:
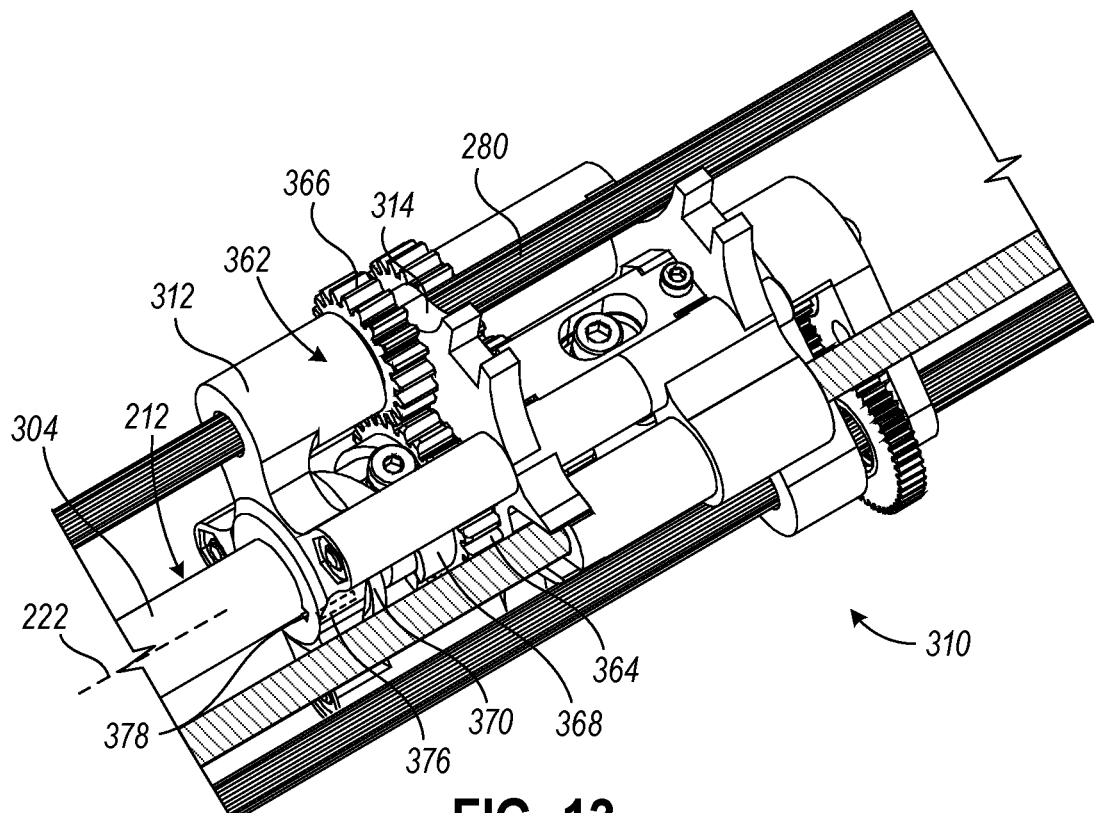
FIG. 13 depicts an enlarged perspective view of the carriage of FIG. 9 having a jaw activating mechanism.
Figure 14:
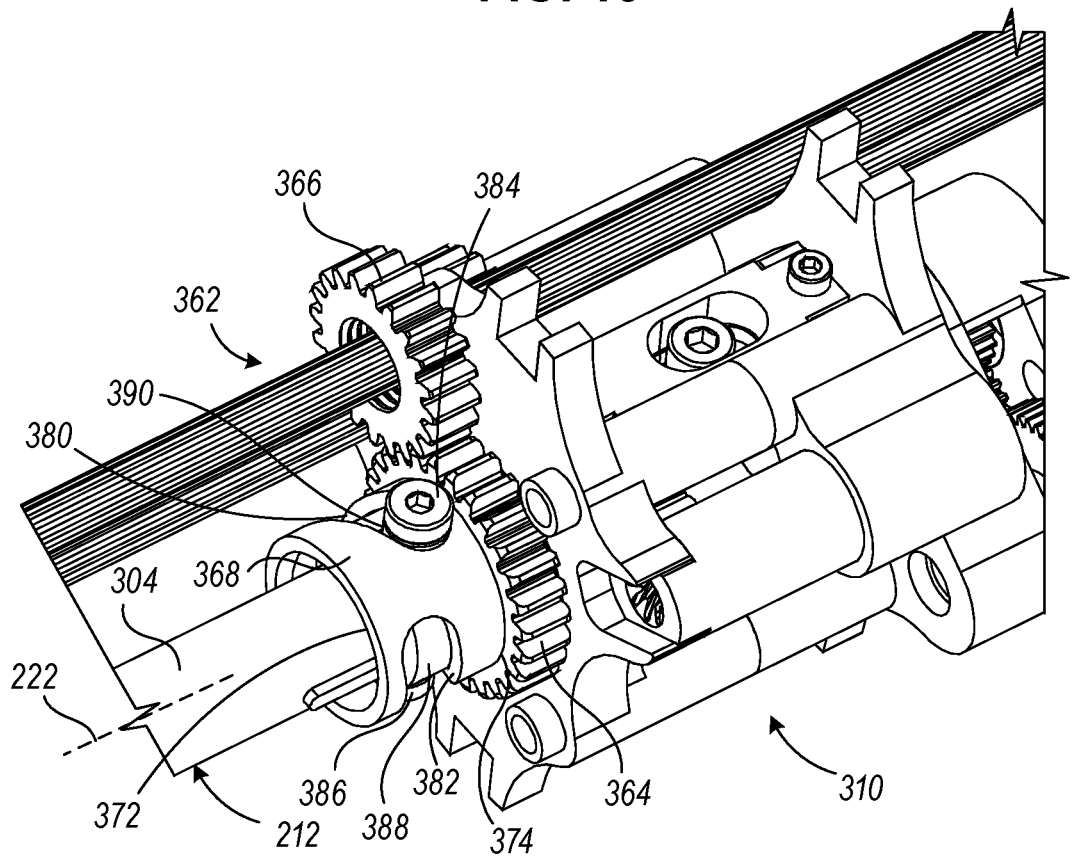
FIG. 14 depicts another enlarged perspective view of the carriage of FIG. 13 with the jaw activating mechanism.

FIGS. 13-14 show carriage (310) discussed above including another activating mechanism (362) configured to move upper jaw (220) relative to lower jaw (218) between the open and closed positions as shown with further reference to FIG. 8B. To this end, first spline (240) is configured to direct such movement of upper jaw (220) such that rotating first spline (240) (e.g., via rotation of second drive input (266)) (see FIG. 7) correspondingly actuates activating mechanism (362) and thereby causes closure tube (304) of shaft (212) to advance or retract along longitudinal axis (222).

Activating mechanism (362) further includes a driven gear (364) that intermeshes with a drive gear (366) of first spline (240) such that rotation of drive gear (366) correspondingly rotates driven gear (364). As shown in the present example, driven gear (364) is coupled with a closure barrel (368). As spline (240) rotates, drive gear (364) drives driven gear (366) and causes closure barrel (368) to rotate about longitudinal axis (222). Closure barrel (368) is positioned in carriage (310) between first and second layers (312, 314). One or more thrust bearings may be arranged at one or both axial ends of closure barrel (368) to effectively bear axial loading on closure barrel (368) and reduce friction during use of activating mechanism (362). More particularly, a plurality of thrust bearings (370) in the present example is arranged at a distal end (372) of closure barrel (368), which is opposite from a proximal end (374) of closure barrel (368) and interpose closure barrel (368) and first layer (248). Additionally, activating mechanism (362) further includes a key (376) on the outer surface of closure tube (304). Key (376) is received within a slot (378) defined in first layer (312) of carriage (310). Actuating activating mechanism (362) causes closure tube (304) to translate along longitudinal axis (222) and correspondingly causes key (376) to translate longitudinally within slot (378) to thereby prevent closure tube (304) from rotating during longitudinal movement of closure tube (304).

Closure barrel (368) has a generally cylindrical structure that extends about closure tube (304) and defines a first cam profile (380) and a second cam profile (382). Each cam profile (380, 382) extends a distance about a circumference of closure barrel (368) (e.g., in a generally helical pattern). While closure barrel (368) provides two cam profiles (380, 382) the invention is not intended to be unnecessarily limited to two such cam profiles (380, 382) such that an alternative number of cam profiles may be similarly incorporated into closure barrel (368).

Activating mechanism (362) further includes a first follower pin (384) and a second follower pin (386) extending through first and second cam profiles (380, 382), respectively, and are operatively coupled to a proximal end of closure tube (304). In one example, first and second follower pins (384, 386) are each coupled to a carrier (388) arranged at the proximal end of closure tube (304). Carrier (388) is configured to receive the proximal end of closure tube (304) and may radially interpose a portion of closure tube (304) and closure barrel (368), and movement of carrier (388) along longitudinal axis (222) will correspondingly move closure tube (304) in a like axial direction.

As drive gear (364) drives driven gear (364), closure barrel (368) correspondingly rotates about longitudinal axis (222), thus urging follower pins (384, 386) to traverse cam profiles (380, 382), respectively. In turn, carrier (388) moves along longitudinal axis (222) and closure tube (304) is urged in the same axial direction. Depending on the rotational direction of drive gear (366), carrier (388) and closure tube (304) may move distally (i.e., to the left in FIG. 14) or proximally (i.e., to the right in FIG. 14) and thereby close or open jaws (218, 220) of end effector (214) as shown in FIG. 8B.

In one example, one or both of follower pins (384, 386) may include one or more bearings (390), and shaft of each follower pin (384, 386) extends through bearings (390). Bearings (390) are configured to bear against inner walls of cam profiles (380, 382) as closure barrel (368) rotates and follower pins (384, 386) traverse cam profiles (380, 382) thereby reducing friction during use.

Figure 15:
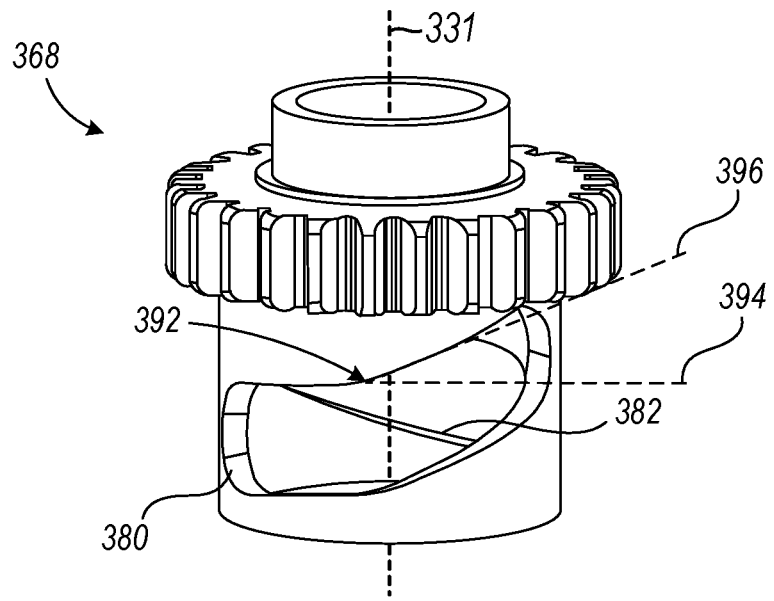
FIG. 15 depicts a first exemplary barrel cam of the jaw activating mechanism of FIG. 13.

FIG. 15 shows one example of the closure barrel (368) in greater detail. As discussed briefly above, each cam profile (380, 382) has a slot extending generally helically about a portion of the circumference of closure barrel (368). In such an example, cam profiles (380, 382) may be more particularly described as helical cam slots, and follower pins (384, 386) may be more particularly described as linear cam followers. Each cam profile (380, 382) has a straight slot extending helically at a constant angle, which may also be referred to herein as a slope, about the circumference of closure barrel (368). The movement applied to carrier (388) and converted into an axial load on closure tube (304) (see FIGS. 13-14) may be constant during actuation of activating mechanism (362) (FIGS. 13-14) through this constant angle.

In one example, one or both of cam profiles (380, 382) may not be entirely straight, but may alternatively diverge at one or more inflection points (392) along a helical length of cam profile (380, 382). More specifically, at inflection point (392), cam profiles (380, 382) change from extending a first distance about the circumference of closure barrel (368) at a first slope (394) to a second distance at a second slope (396) such that second slope (396) has a more or less aggressive path as compared to first slope (394). A higher or lower slope of cam profile (380, 382) will correspondingly alter a mechanical advantage obtained as follower pins (384, 386) traverse cam profiles (380, 382) and act on interconnected carrier (388). Such mechanical advantage may result in higher axial loads being applied to closure tube (304) (see FIGS. 13-14) and allow jaws (218, 220) (see FIG. 8B) to clamp down with enhanced force and/or greater precision during use.

III. EXEMPLARY ALTERNATIVE ACTIVATING MECHANISMS

A. Overview

Figure 16:
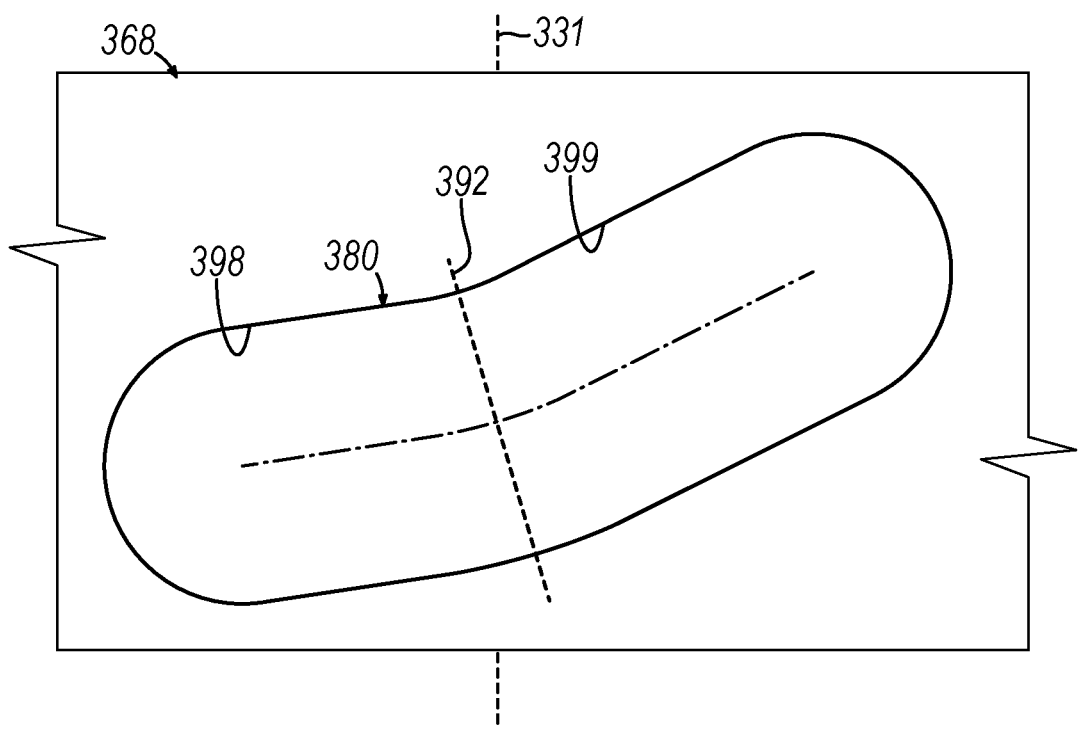
FIG. 16 depicts a schematic view of a portion of barrel cam of the FIG. 15.

It may be desirable to perform different actions using the same activating mechanism, while also tailoring the activating mechanism to the desired action. It may be desirable to use the same activating mechanism to perform multiple tasks to reduce equipment changeovers. One such example of an activating mechanism is activating mechanism (362) shown and described with reference to FIGS. 13-14. As previously described, activating mechanism (362) may include closure barrel (368), also referred to as a barrel cam. FIG. 16 shows a schematic view of a portion of closure barrel (368) of FIG. 15. More particularly, cam profile (380) is shown schematically in an "un-rolled" configuration. In this "un-rolled" configuration, cam profile (380) is shown as if closure barrel (368) was cut along a longitudinal rotation axis (331) and laid out in a plane.

As used herein, a cam profile "slope" refers to an angle of a cam profile, such as cam profile (380), taken at a point relative to the rotation axis (331) when un-rolled in a plane, such as in FIG. 16. The slope essentially extends as a line from this point and intersects the rotation axis (331) to collectively define supplementary angles cumulatively equal to 180°. As also used herein, a relatively higher slope is formed with a greater difference between these supplementary angles, whereas a relatively lower slope is formed with less difference between these supplementary angles. For instance, an example of a relatively high slope is the intersection of a cam profile slope and the rotation axis forming a 1° angle and a 179° angle set of supplementary angles, whereas an example of a relatively low slope is the intersection of a cam profile slope and the rotation axis forming an 89° angle and a 91° angle set of supplementary angles. By way of further example, a "zero" slope is the intersection of a cam profile slope and the rotation axis forming a 90° angle and another 90° angle set of supplementary angles. Generally, higher slope applications of a cam profile have less mechanical advantage, but rotational input (e.g., a rotational input distance), yields greater linear output (e.g., a linear output distance), such that the linear output moves more quickly (e.g., speed). In contrast, lower slope applications of a cam profile have more mechanical advantage, but the same rotational input (e.g., a rotational input distance), yields less linear output (e.g., a linear output distance), such that the linear output moves more slowly (e.g., speed). This relationship between mechanical advantage and speed may be referred to in any of these terms and, in conjunction with high and low slopes, applies to each example of a cam profile discussed herein.

Closure barrel (368) allows a first end effector action when a first predetermined path (398) is selected and a second end effector action when a second predetermined path (399) is selected. In some versions, the first end effector action may include a manual operation. Additionally, in some versions, the second end effector action may include a robotic operation. While first and second predetermined paths (398, 399) are shown with respect to first cam profile (380) of FIG. 16, these principles also apply to second cam profile (382).

Figure 17:
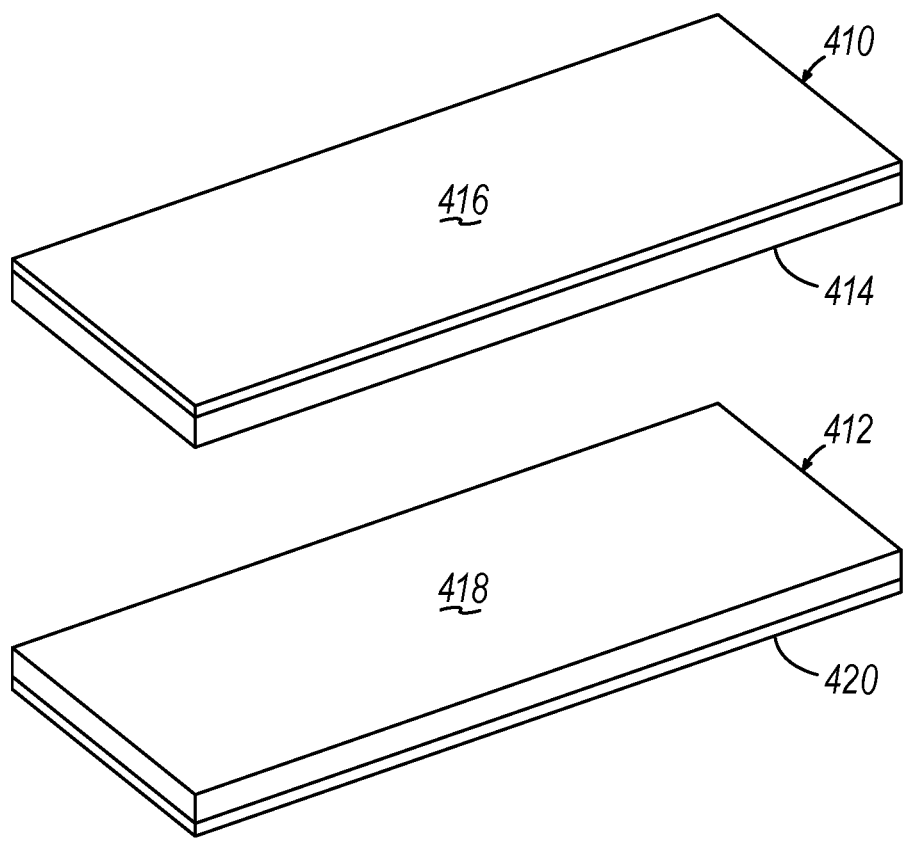
FIG. 17 depicts a perspective view of first and second exemplary buttresses, each of which may be applied to a jaw of the end effector of FIG. 8A.

Manual operation may include applying one or more buttresses (410, 412) to first and/or second jaws (e.g., lower and upper jaws (218, 220) of end effector (214)). Regarding the application of buttresses (401, 412), FIG. 17 shows a perspective view of first and second exemplary buttresses (each also referred to individually as a "buttress assembly"), each of which may be applied to a jaw of end effector (214) of FIG. 8A. Buttress (410) comprises a buttress body (414) and an upper adhesive layer (416). Similarly, buttress (412) comprises a buttress body (418) and a lower adhesive layer (420). In the present example, each buttress body (414, 418) comprises a strong yet flexible material configured to structurally support a line of staples (not shown). Buttresses (410, 412) described herein may be combined with any one or more of the teachings disclosed in U.S. patent application Ser. No. 17/022,520, entitled "Method of Applying Buttress (410, 412) to End Effector of Surgical Stapler," filed on Sep. 16, 2020, issued as U.S. Pat. No. 11,660,093 on May 30, 2023, the disclosure of which is incorporated by reference herein in its entirety and/or U.S. Pat. No. 10,349,939, entitled "Method of Applying a Buttress (410, 412) to a Surgical Stapler," issued on Jul. 16, 2019, the disclosure of which is incorporated by reference herein in its entirety.

Adhesive layer (416) on buttress body (414) adheres buttress body (414) to underside of upper jaw (220). Similarly, adhesive layer (420) on buttress body (418) adheres buttress body (418) to a stapling assembly (e.g., a staple cartridge of lower jaw (218)).

With respect to FIGS. 15-17, rotating closure barrel (368) in a first direction along first predetermined path (398) may provide for manual application of one or more buttresses (410, 412). Conversely, rotating closure barrel (368) in a second direction along second predetermined path (399), opposite to the first direction, may provide for robotically driven grasping and/or clamping. As a result, there may be benefits associated with providing an activating mechanism with multiple paths (e.g., first and second predetermined paths (398, 399)) that include differing mechanical advantages and/or angle profiles. In some versions, closure barrel (368) may apply one or more buttresses (410, 412) with a certain stroke and load through first predetermined path (398), which is also referred to as a clamping zone. In some instances, closure barrel (368) may grasp tissue within an acceptable time and load to achieve the desired closure load on tissue through second predetermined path (399), which is also referred to as a grasping zone. The clamping zone may utilize a higher mechanical advantage and a lower speed as compared to the grasping zone which may utilize a lower mechanical advantage and a higher speed.

While using the same activating mechanism to perform different actions may be desirable, it is further beneficial to ensure that the desired action is selected. For example, it is beneficial to ensure the desired predetermined path (e.g., first and second cam profiles (380, 382) of closure barrel (368)) is selected for two different actions of end effector (214). Likewise, it may be beneficial to prevent closure of end effector (214) where the undesired predetermined path (e.g., first and second cam profiles (380, 382)) is inadvertently selected.

As previously described, robotic surgical system (10) includes at least one robotic arm (32) and at least one surgical instrument (210), with surgical instrument (210) including shaft assembly (212), and end effector (214). As will be described in greater detail below with reference to FIGS. 18A-33, surgical instrument (210) includes an exemplary activating mechanism (510, 610, 710, 810, 910, 1010, 1110, 1210, 1310, 1410) instead of activating mechanism (362) and an exemplary drive (512, 612, 712, 812, 912, 1012, 1112, 1212, 1312, 1412). Additionally, activating mechanism (510, 610, 710, 810, 910, 1010, 1110, 1210, 1310, 1410) includes an exemplary actuation body (514, 614, 714, 814, 914, 1014, 1114, 1214, 1314, 1414) operatively connected to drive (512, 612, 712, 812, 912, 1012, 1112, 1212, 1312, 1412).

B. First Exemplary Alternative Activating Mechanism

Figure 18A:
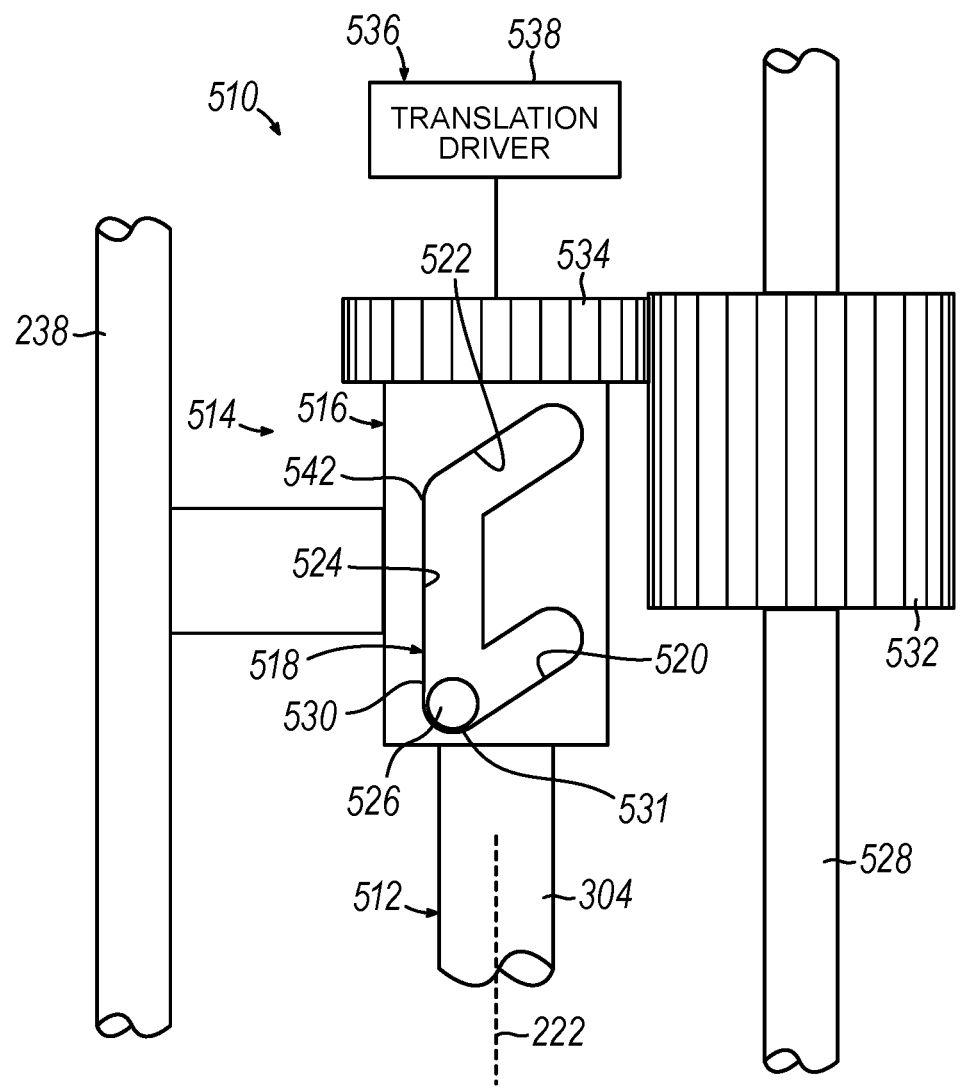
FIG. 18A depicts a schematic view of a first exemplary alternative activating mechanism configured for use with the carriage of FIG. 13, where the activating mechanism includes a barrel cam, with a follower positioned in a neutral position of the barrel cam.
Figure 18B:
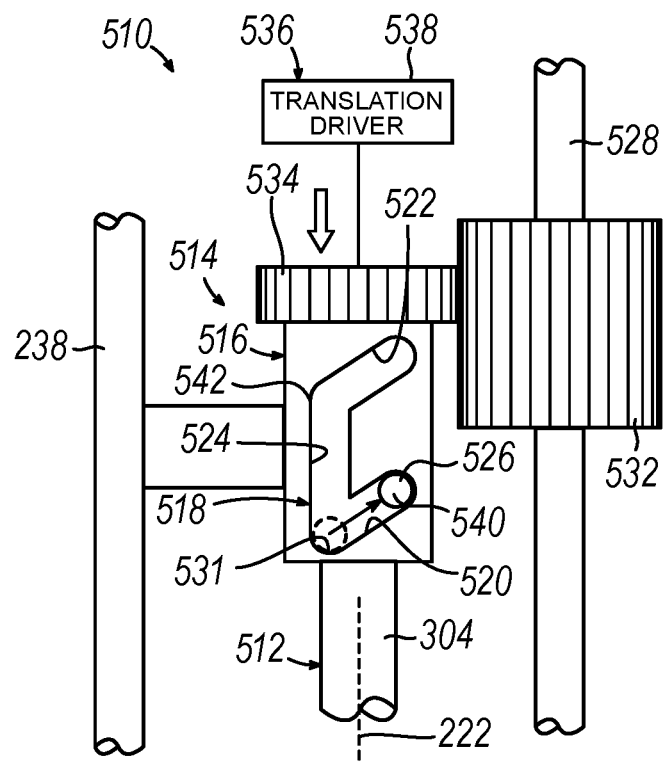
FIG. 18B depicts a schematic view of the activating mechanism of FIG. 18A, but with the follower moved along a first predetermined path of the barrel cam.
Figure 18C:
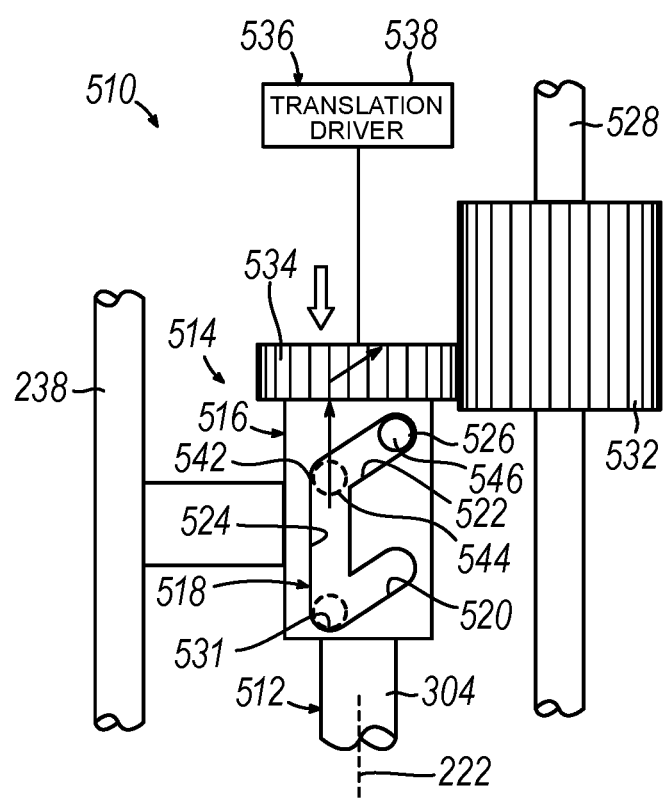
FIG. 18C depicts a schematic view of the activating mechanism of FIG. 18A, but with the follower moved along a second predetermined path of the barrel cam.

FIGS. 18A-18C show schematic views of a first exemplary alternative activating mechanism (510) configured for use with carriage (310) of FIG. 13 instead of activating mechanism (362). Actuation body (514) of activating mechanism (510) includes a barrel cam (516). Barrel cam (516) extends parallel to a longitudinal axis (222) (see FIGS. 13-14) defined by shaft assembly (212). Barrel cam (516) is configured to selectively rotate and selectively translate about longitudinal axis (222). Barrel cam (516) includes a cam slot (518). Cam slot (518) includes first and second predetermined paths (520, 522) as well as a longitudinally extending portion (524) interposed between first and second predetermined paths (520, 522). Longitudinally extending portion (524) connects first and second predetermined paths (520, 522). Longitudinally extending portion (524) extends parallel to longitudinal axis (222).

Drive (512) is operatively connected to a portion of end effector (214) or shaft assembly (212). In some versions, the portion of end effector (214) or shaft assembly (212) may include one of the lower and upper jaws (218, 220) of end effector (214). Drive (512) may include closure tube (304) and at least one follower, shown as a follower pin (526). Drive (512) may also include other suitable components. Follower pin (526) is configured to be received within cam slot (518), such that cam slot (518) guides movement of follower pin (526) as actuation body (514) moves along one of first and second predetermined paths (520, 522). Particularly, FIG. 18A shows follower pin (526) positioned in a proximal neutral position (530) of barrel cam (516) at a first end (531) of a longitudinally extending portion (524), prior to barrel cam (516) being rotated or translated as will be discussed with reference to FIGS. 18B-18C.

A rotational driver, shown as spline (528) which is similar to spline (242), is operatively engaged with actuation body (514) and is configured to selectively rotate actuation body (514). Particularly, spline (528) rotates a drive gear (532), similar to drive gear (322). Drive gear (532) is rotatably engaged with a driven gear (534) using spur shaped gear teeth. Barrel cam (516) is rotatably and translatably fixed relative to driven gear (534), which is similar to driven gear (324). Unlike drive gear (322), drive gear (532) includes a greater face width allowing drive gear (532) to remain engaged with driven gear (534) when the barrel cam (516) is moved between proximal and distal positions as shown in a comparison between FIGS. 18A-18C. Actuation body (514) is rotatably and translatably coupled with driven gear (534). Activating mechanism (510) includes a shifting mechanism (536) configured to direct actuation body (514) between first and second predetermined paths (520, 522). As shown, shifting mechanism (536) includes longitudinally extending portion (524) and a translation driver (538).

FIG. 18B shows a schematic view of activating mechanism (510) of FIG. 18A, but with follower pin (526) moved along first predetermined path (520) of barrel cam (516) from first end (531) of longitudinally extending portion (524) while in proximal neutral position (530) to a first rotated position (540) in first predetermined path (520). When the barrel cam (516) is proximally located, follower pin (526) may enter and access first predetermined path (520). Selection of first predetermined path (520) is configured to prevent actuation body (514) from accessing second predetermined path (522). This is because follower pin (526) is not rotatable into second predetermined path (522) without follower pin (526) moving relative to cam slot (518) (e.g., through translation of barrel cam (516) by translation driver (538)). End effector (214) is configured to perform a first actuation profile in response to movement of follower pin (526) due to actuation body (514) moving along first predetermined path (520). In some versions, the first actuation profile may allow a user to apply buttresses (410, 412) to at least one of lower and upper jaws (218, 220) of end effector (214). For example, buttresses (410, 412) may be applied to at least one of lower and upper jaws (218, 220) when surgical instrument (210) is not coupled with robotic arm (32), which is also referred to as an off-robot action.

FIG. 18C shows a schematic view of activating mechanism (510) of FIG. 18A, but with actuation body (514) translated distally and rotated. Translational driver (538) is engaged with actuation body (514) and is configured to selectively translate actuation body (514) from a first translational body position (see FIG. 18A) toward a second translational body position. Translational driver (538) selectively translates actuation body (514) causing follower pin (526) to move to second end (542) of longitudinally extending portion (524). Without this translation of actuation body (514), follower pin (526) cannot access second predetermined path (522). As shown, follower pin (526) is first moved along second predetermined path (522) of barrel cam (516) to a translated position (544). Once follower pin (526) is in translated position (544), follower pin (526) may then be moved to a second rotated position (546) by rotating actuation body (514) which rotates barrel cam (516) in a similar manner to follower pin (526) being moved to first rotated position (540) in first predetermined path (520) of FIG. 18B. As shown, selection of second predetermined path (522) prevents actuation body (514) from accessing first predetermined path (520) until translational driver (538) selectively translates actuation body (514) proximally to the position of FIG. 18A.

End effector (214) performs a second actuation profile in response to actuation body (514) moving along second predetermined path (522). In some versions, second actuation profile may manipulate tissue using robotic arm (32) of robotic surgical system (10) while surgical instrument (210) is coupled with robotic arm (32), also referred to as an on-robot action. More specifically, the second actuation profile may clamp and compress tissue between lower and upper jaws (218, 220) of end effector (214). The first and second actuation profiles may include other actions of end effector (214). When barrel cam (516) is distal, rotation of barrel cam (516) causes follower pin (526) to enter second predetermined path (522). In some versions, barrel cam (516) may fit within the same footprint of closure barrel (368).

C. Second Exemplary Alternative Activating Mechanism

Figure 19A:
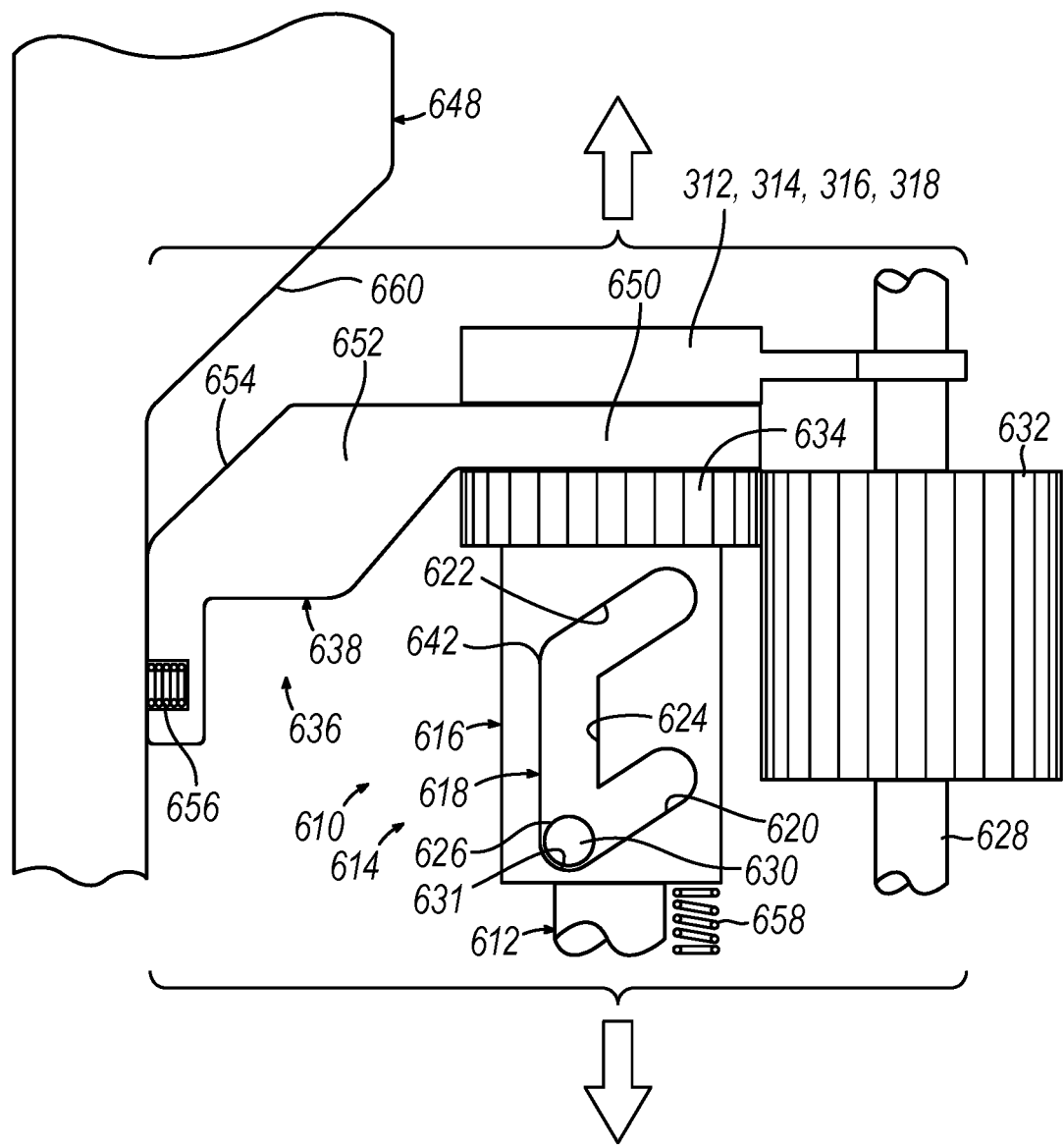
FIG. 19A depicts a schematic view of a second exemplary alternative activating mechanism configured for use with the carriage of FIG. 13, where the activating mechanism includes a closure barrel and a wedge, with a follower is positioned in a neutral position of the barrel cam.
Figure 19B:
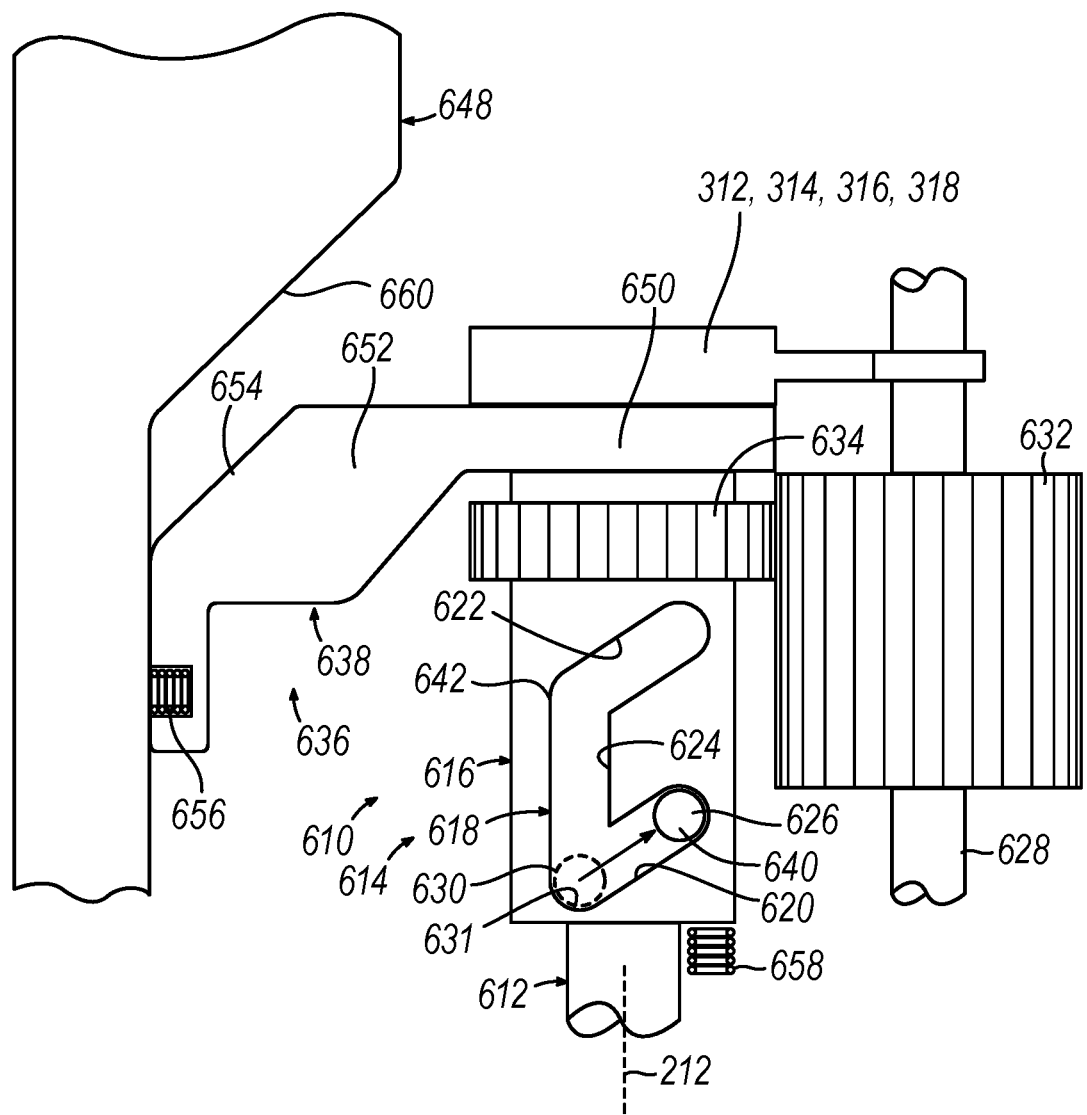
FIG. 19B depicts a schematic view of the activating mechanism of FIG. 19A, but with the wedge in a first position against a housing and the follower moved along a first predetermined path of the barrel cam.
Figure 19C:
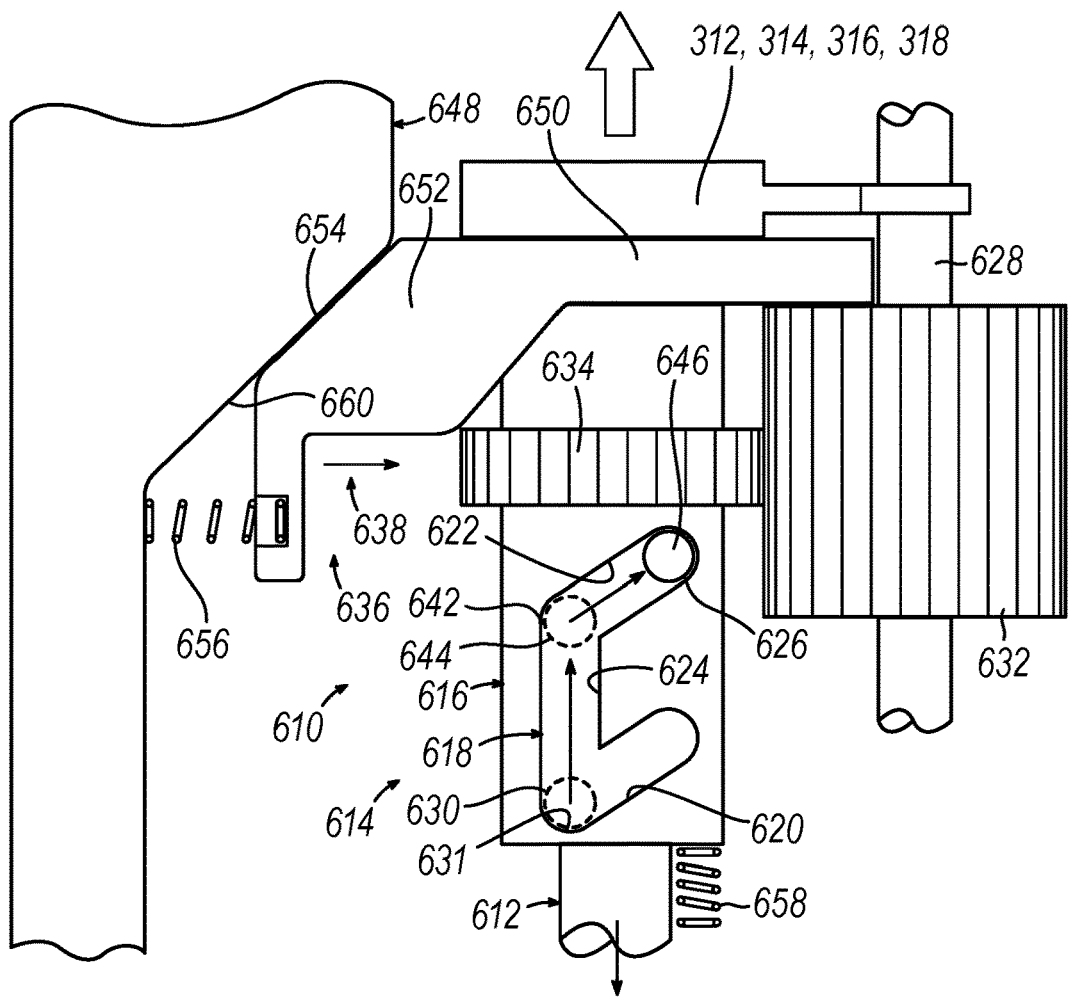
FIG. 19C depicts a schematic view of the activating mechanism of FIG. 19A, but with the wedge in a second position against the housing and the follower moved along a second predetermined path of the barrel cam.
Figure 20:
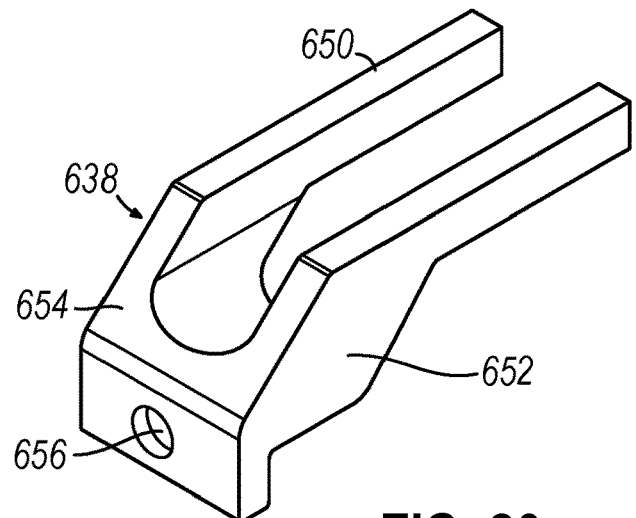
FIG. 20 depicts a perspective view of the wedge of FIG. 19A.

FIGS. 19A-20 show schematic views of a second exemplary alternative activating mechanism (610) configured for use with carriage (310) of FIG. 13 instead of activating mechanism (362). Similar to actuation body (514), actuation body (614) of activating mechanism (610) includes a barrel cam (616). Barrel cam (616) extends parallel to a longitudinal axis (222) (see FIGS. 13-14) defined by shaft assembly (212). Barrel cam (616) is configured to selectively rotate and selectively translate about longitudinal axis (222). Barrel cam (616) includes a cam slot (618), similar to cam slot (518). Cam slot (618) includes first and second predetermined paths (620, 622) as well as a longitudinally extending portion (624) interposed between first and second predetermined paths (620, 622).

Similar to drive (512), drive (612) is operatively connected to a portion of end effector (214) or shaft assembly (212). In some versions, the portion of end effector (214) or shaft assembly (212) may include one of the lower and upper jaws (218, 220) of end effector (214). Drive (612) may include closure tube (304) and at least one follower, shown as a follower pin (626). Drive (612) may also include other suitable components. Follower pin (626) is similar to follower pin (526). Follower pin (626) is configured to be received within cam slot (618), such that cam slot (618) guides movement of follower pin (626) as actuation body (614) moves along one of first and second predetermined paths (620, 622). Particularly, FIG. 19A shows follower pin (626) positioned in a proximal neutral position (630) of barrel cam (616) at a first end (631) of longitudinally extending portion (624), prior to barrel cam (616) being rotated or translated as will be discussed with reference to FIGS. 19B-19C.

A rotational driver, shown as spline (628) and similar to spline (528), is operatively engaged with actuation body (614) and is configured to selectively rotate actuation body (614). Particularly, spline (628) rotates a drive gear (632), similar to drive gear (532). Drive gear (632) is rotatably engaged with a driven gear (634) using spur shaped gear teeth. Barrel cam (616) is rotatably and translatably fixed relative to driven gear (634), which is similar to driven gear (324). Like drive gear (532), drive gear (632) includes a greater face width allowing drive gear (632) to remain engaged with driven gear (634) when the barrel cam (616) is moved between proximal and distal positions. Actuation body (614) is rotatably and translatably coupled with driven gear (634).

Activating mechanism (610) includes a shifting mechanism (636) configured to direct actuation body (614) between first and second predetermined paths (620, 622). Unlike shifting mechanism (536) shown in FIGS. 18A-18C, shifting mechanism (636) includes a wedge (638), a housing (648), and longitudinally extending portion (624). As best shown in FIG. 20 illustrating a perspective view of wedge (638), wedge (638) includes a thin forked portion (650), a thick forked portion (652), and a ramp (654). Ramp (654) is configured to selectively engage a ramp (660) of housing (648) causing wedge (638) to translate. As shown, ramps (654, 660) are planar faces; however, the shape and dimensions of ramps (654, 660) may vary. As shown in FIG. 19C, wedge (638) translates in a direction generally perpendicular to longitudinal axis (222). In some versions, housing (648) may be formed with or coupled to shroud (278) shown in FIG. 7. As shown in FIG. 19A, when carriage (310) is in a first position, ramp (654) is spaced from housing (648). In other versions when carriage (310) is in a first position, ramp (654) may engage housing (648) in a manner that does not affect the positioning of barrel cam (616). Wedge (638) may be biased toward housing (648) using a first biasing mechanism, shown in the form of a first spring (656). Barrel cam (616) may be biased distally using a second biasing mechanism, shown as a second spring (658). Other examples of first and second biasing mechanisms are also envisioned.

FIG. 19B shows a schematic view of activating mechanism (610) of FIG. 19A, with follower pin (626) moved along first predetermined path (620) of barrel cam (616) from first end (631) of longitudinally extending portion (624) while in proximal neutral position (630) to a first rotated position (640) in first predetermined path (620). As shown, wedge (638) is generally in the same position as in FIG. 19A. When carriage (310) is in the first position relative to housing (648), thin forked portion (650) of wedge (638) is disposed between one of layers (312, 314, 316, 318) of carriage (310) and barrel cam (616), which aligns first predetermined path (620) up with follower pin (626). When the barrel cam (616) is proximally located, follower pin (626) may enter and access first predetermined path (620). Selection of first predetermined path (620) is configured to prevent actuation body (614) from accessing second predetermined path (622). End effector (214) is configured to perform a first actuation profile in response to movement of follower pin (626) due to actuation body (614) moving along first predetermined path (620). In some versions, the first actuation profile may allow a user to apply buttresses (410, 412) to at least one of lower and upper jaws (218, 220) of end effector (214).

FIG. 19C shows a schematic view of activating mechanism (610) of FIG. 19A, but with wedge (638) moved to a second position against housing (648) and actuation body (614) translated distally and rotated. As carriage (310)

moves to a second position relative to housing (648), ramp (654) of wedge (638) contacts housing (648), causing wedge (638) to translate in a direction generally transverse to longitudinal axis (222). Ramp (654) of wedge (638) moves between one of layers (312, 314, 316, 318), of carriage (310) and barrel cam (616). This movement of ramp (654) aligns second predetermined path (622) with follower pin (626). When wedge (638) translates, barrel cam (616) translates distally, aligning second end (642) of longitudinally extending portion (624) with follower pin (626) at the start of second predetermined path (622). While this increases the spring force of first and second springs (656, 658), the force ramp (654) exerts on ramp (654) of wedge (638) and actuation body (614) exceeds the respective spring forces.

Wedge (638) selectively translates actuation body (614) causing follower pin (626) to move to second end (642) of longitudinally extending portion (624). Without this translation of actuation body (614), follower pin (626) may not access second predetermined path (622). As shown, follower pin (626) is first moved along second predetermined path (622) of barrel cam (616) to a translated position (644).

Once follower pin (626) is in translated position (644), follower pin (626) may then be moved to a second rotated position (646) by rotating actuation body (614) which rotates barrel cam (616). When barrel cam (616) is distal, rotation of barrel cam (616) causes follower pin (626) to enter second predetermined path (622). As shown, selection of second predetermined path (622) prevents actuation body (614) from accessing first predetermined path (620) until wedge (638) selectively translates actuation body (614) proximally to the position of FIG. 19A. End effector (214) performs a second actuation profile in response to actuation body (614) moving along second predetermined path (622), similar to second predetermined path (522). In some versions, second actuation profile may manipulate tissue using robotic arm (32) of robotic surgical system (10) while surgical instrument (210) is coupled with robotic arm (32), also referred to as an on-robot action. In some versions, barrel cam (616) may fit within the same footprint of closure barrel (368).

After entering one of first or second predetermined paths (620, 622), spline (628) may be rotated in the opposite direction to rotate barrel cam (616) so that follower pin (626) moves to first end (631) of longitudinally extending portion (624) after rotation out of first predetermined path (620) or moves to second end (642) of longitudinally extending portion (624) after rotation out of second predetermined path (622) depending on the entered path. Once follower pin (626) moves to second end (642) of longitudinally extending portion (624), housing (648) may be moved away from wedge (638). Moving housing (648) away from wedge (638) causes wedge (638) to translate back to the position of FIG. 19A to the spring force exerted by first spring (656), and barrel cam (616) to move proximally due to the spring force exerted by second spring (658).

D. Third Exemplary Alternative Activating Mechanism

Figure 21A:
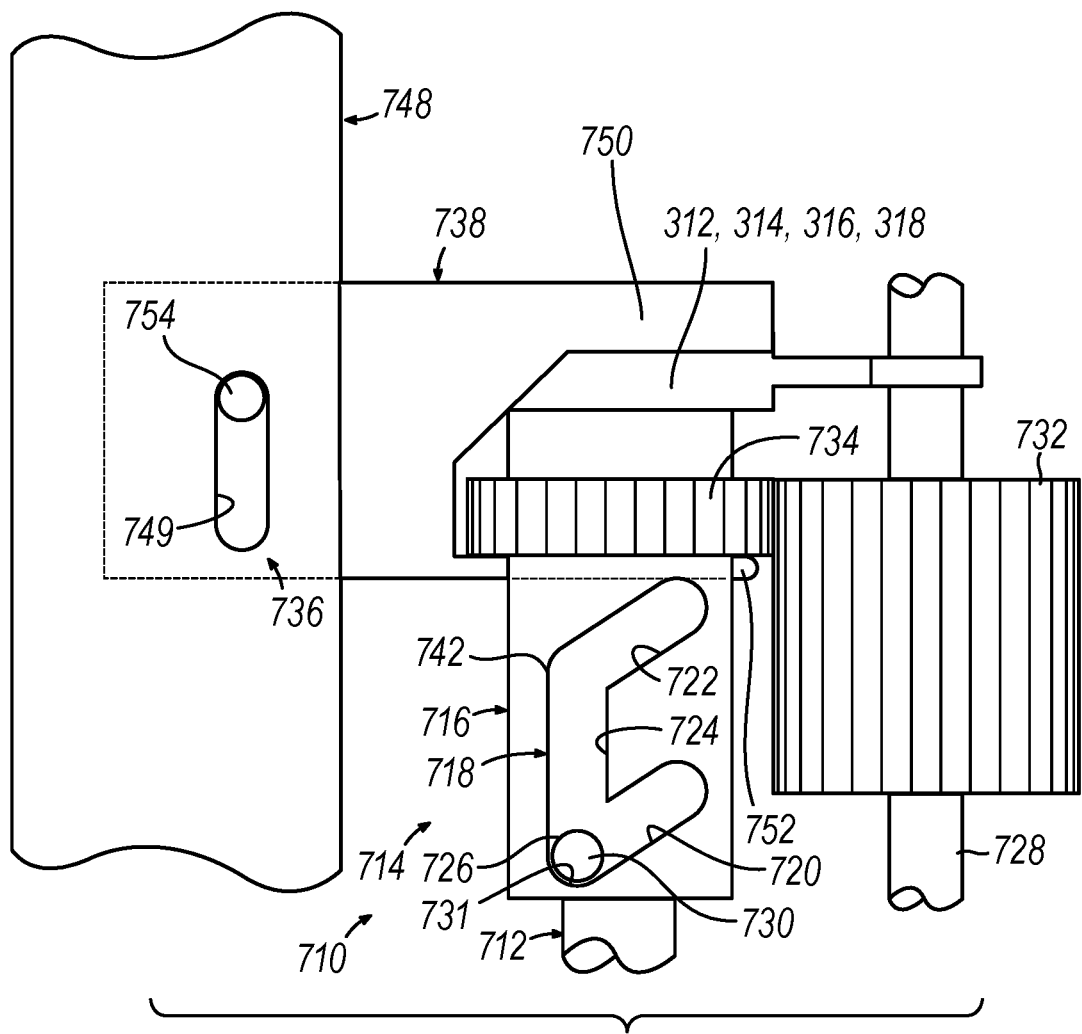
FIG. 21A depicts a schematic view a third exemplary alternative activating mechanism configured for use with the carriage of FIG. 13, where the activating mechanism includes a barrel cam and a pin, where a follower is positioned in a neutral position of the barrel cam.
Figure 21B:
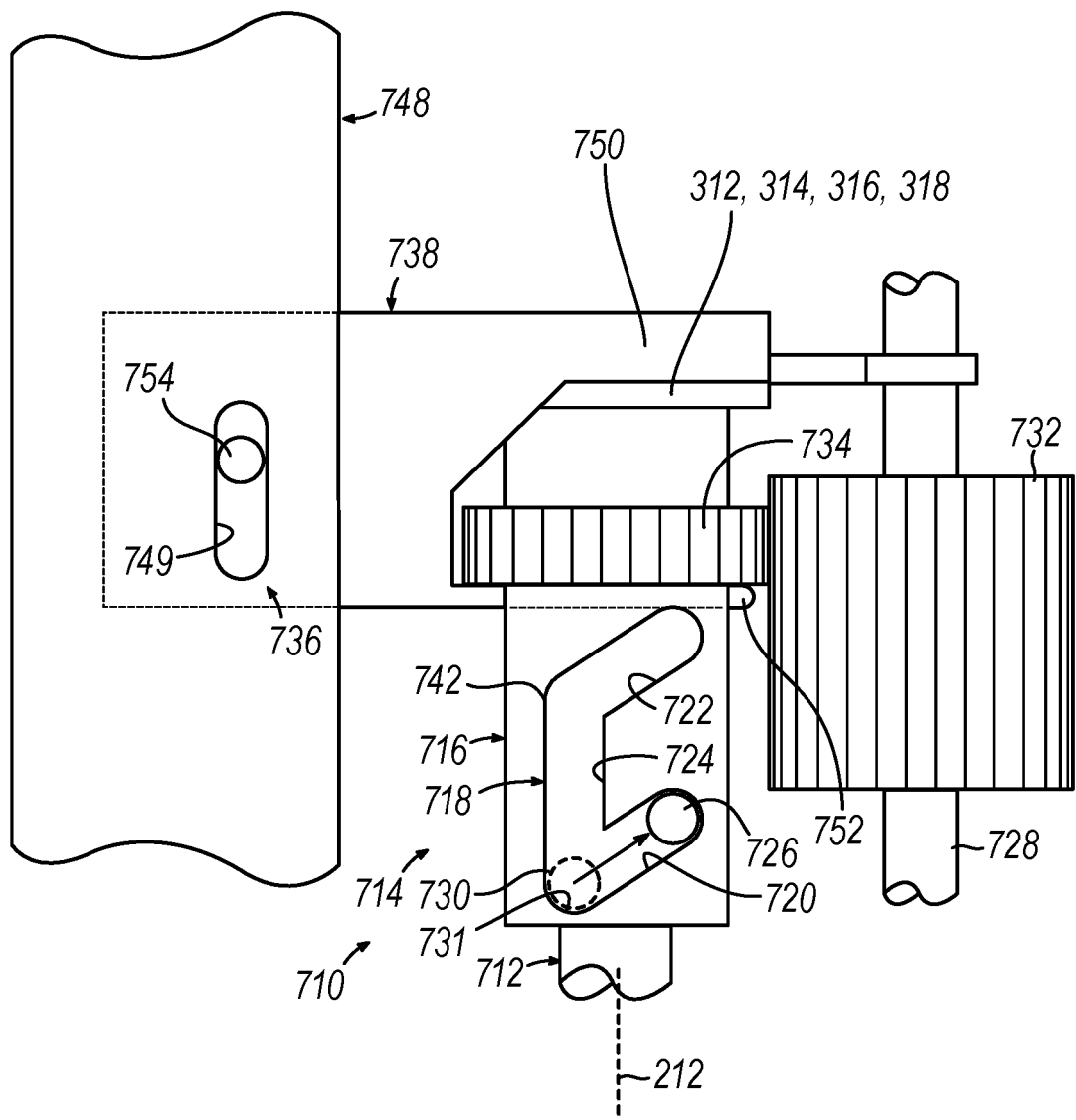
FIG. 21B depicts a schematic view of the carriage of FIG. 21A, but with the pin in a first position and the follower moved along a first predetermined path of the barrel cam.
Figure 21C:
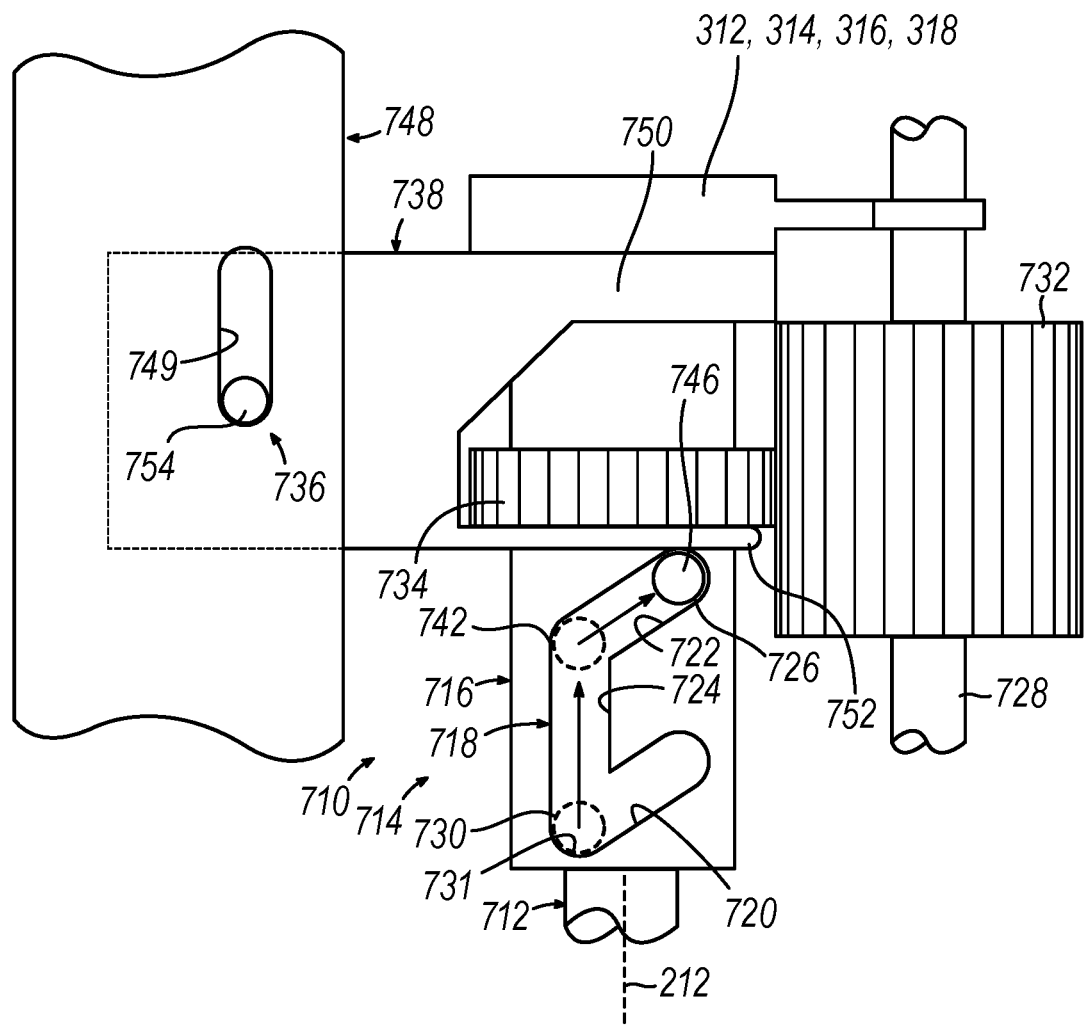
FIG. 21C depicts a schematic view of the carriage of FIG. 21A, but with the pin in a second position and the follower moved along a second predetermined path of the barrel cam.

FIGS. 21A-21C show schematic views of a third exemplary alternative activating mechanism (710) configured for use with carriage (310) of FIG. 13 instead of activating mechanism (362). Similar to actuation body (614), actuation body (714) of activating mechanism (710) includes a barrel cam (716), similar to barrel cam (616). Barrel cam (716) includes a cam slot (718). Cam slot (718) includes first and second predetermined paths (720, 722) as well as a longitudinally extending portion (724) interposed between first and second predetermined paths (720, 722).

Similar to drive (612), drive (712) is operatively connected to a portion of end effector (214) or shaft assembly (212). Drive (712) may include closure tube (304) and at least one follower, shown as a follower pin (726). Drive (712) may also include other suitable components. FIG. 21A shows follower pin (726) positioned in a proximal neutral position (730) of barrel cam (716) at a first end (731) of longitudinally extending portion (724), prior to barrel cam (716) being rotated or translated as will be discussed with reference to FIGS. 21B-21C. A rotational driver, shown as spline (728) which is similar to spline (628), is operatively engaged with actuation body (714) and is configured to selectively rotate actuation body (714). Particularly, spline (728) rotates a drive gear (732), similar to drive gear (632). Drive gear (732) is rotatably engaged with a driven gear (734) using spur shaped gear teeth.

Activating mechanism (710) includes a shifting mechanism (736) configured to direct actuation body (714) between first and second predetermined paths (720, 722). Similar to shifting mechanism (636) shown in FIGS. 19A-19C, shifting mechanism (736) includes a wedge (738), a housing (748), and longitudinally extending portion (724). However, unlike wedge (638), wedge (738) includes a proximal arm (750), a distal arm (752), and a pin (754). Unlike housing (648), housing (748) includes a cam slot (749). Wedge (738) may be pulled as well as pushed by housing (748), and may omit separate biasing mechanisms. While cam slot (749) is shown as extending parallel to longitudinal axis (222), it is envisioned that cam slot (749) may extend at an angle relative to longitudinal axis (222) and have a variety of suitable shapes and sizes. Pin (754) of wedge (638) is configured to selectively move within cam slot (749) to move follower pin (726) between first and second ends (731, 742) of longitudinally extending portion (724). As shown in FIG. 21C, wedge (738) translates in a direction generally perpendicular to longitudinal axis (222). In some versions, housing (748) may be formed with or coupled to shroud (278) shown in FIG. 7.

FIG. 21B shows a schematic view of activating mechanism (710) of FIG. 21A, with follower pin (726) moved along first predetermined path (720) of barrel cam (716) from first end (731) of longitudinally extending portion (724) while in proximal neutral position (730) to a first rotated position (740) in first predetermined path (720). As shown, wedge (738) is generally in the same position as in FIG. 21A.

FIG. 21C shows a schematic view of activating mechanism (710) of FIG. 21A, but with wedge (738) moved to a second position relative to housing (748) and actuation body (714) translated distally and rotated. Wedge (738) selectively translates actuation body (714) causing follower pin (726) to move to second end (742) of longitudinally extending portion (724). Without this translation of actuation body (714), follower pin (726) may not access second predetermined path (722). As carriage (310) moves to a second position relative to housing (748), pin (754) of wedge (738) moves distally within cam slot (749) of housing (748), causing wedge (738) to translate transversely. Pin (754) of wedge (738) moves between one of layers (312, 314, 316, 318) of carriage (310) and barrel cam (716), which aligns second predetermined path (722) with follower pin (726). When wedge (738) translates, proximal arm (750) of wedge (738) causes barrel cam (716) to translate distally, aligning second end (742) of longitudinally extending portion (724) with follower pin (726) at the start of second predetermined path (722). As shown, follower pin (726) is first moved along second predetermined path (722) of barrel cam (716) to a translated position (744).

Once follower pin (726) is in translated position (744), follower pin (726) may then be moved to a second rotated position (746) by rotating actuation body (714) which rotates barrel cam (716), similar to second rotated position (646) shown in FIG. 21C. Selection of second predetermined path (722) prevents actuation body (714) from accessing first predetermined path (720) until wedge (738) selectively translates actuation body (714) proximally to the position of FIG. 21A. End effector (214) performs a second actuation profile in response to actuation body (714) moving along second predetermined path (722), similar to second predetermined path (622).

After entering one of first or second predetermined paths (720, 722), spline (728) may be rotated similar to spline (628). Once follower pin (726) moves to second end (742) of longitudinally extending portion (724), housing (748) may be move away proximally. Moving housing (748) proximally causes pin (754) of wedge (738) to translate back to the position of FIG. 21A. When wedge (738) translates, distal arm (752) of wedge (738) causes barrel cam (716) to translate proximally, aligning second end (742) of longitudinally extending portion (724) with follower pin (726) at first end (731) of longitudinally extending portion (724).

E. Fourth Exemplary Alternative Activating Mechanism

FIGS. 22A-22D show schematic views of a portion of a fourth exemplary alternative activating mechanism (810) configured for use with carriage (310) of FIG. 13. Actuation body (814) of activating mechanism (810) includes a barrel cam (816), a portion of which is shown schematically in an un-rolled configuration in FIGS. 22A-22D. Barrel cam (816) may be used instead of closure barrel (386). Unlike closure barrel (386) that includes first and second cam profiles (380, 382), barrel cam (816) includes a continuous cam slot (818). Continuous cam slot (818) extends entirely around the circumference of barrel cam (816). Continuous cam slot (818) includes first and second predetermined paths (820, 822). First and second predetermined paths (820, 822) collectively extend continuously around the entire circumference of barrel cam (816). In some versions, continuous cam slot (818) may extend only partially though the inside of barrel cam (816). Alternatively, continuous cam slot (818) may include exterior connecting portions (not shown) configured to connect first and body second portions (824, 828) of barrel cam (816). In other versions, first body portion may be coupled with driven gear (324) and second body portion (828) may be operatively coupled with closure tube (304) as shown in FIGS. 13-14.

Drive (812) is operatively connected to a portion of end effector (214) or shaft assembly (212). In some versions, the portion of end effector (214) or shaft assembly (212) may include one of lower and upper jaws (218, 220) of end effector (214). Drive (812) may include closure tube (304) and at least one follower, shown as a follower pin (826). Drive (812) may also include other suitable components. Follower pin (826) is configured to be received within continuous cam slot (818), such that continuous cam slot (818) guides movement of follower pin (826) as actuation body (814) moves along one of first and second predetermined paths (820, 822). As a result, follower pin (826) may travel through second predetermined path (822) and then enter first predetermined path (820).

Figure 22A:
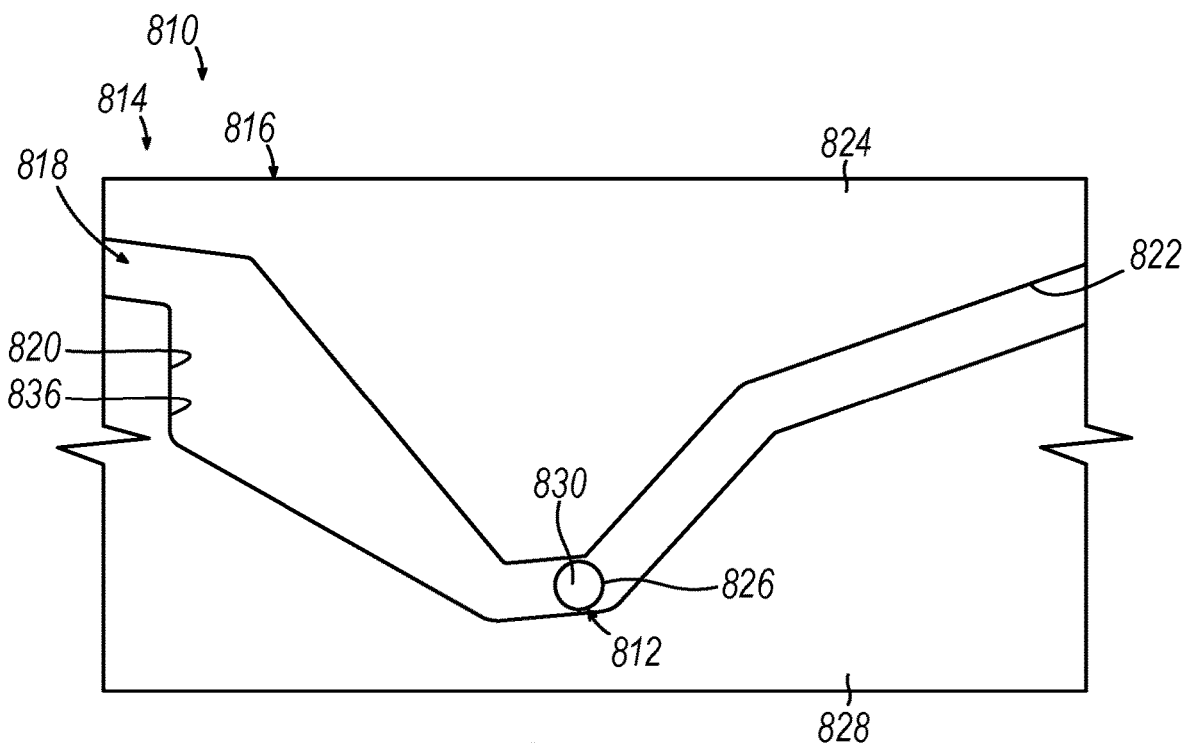
FIG. 22A depicts a schematic view of a portion of a fourth exemplary alternative activating mechanism that includes a portion of the barrel cam similar to FIG. 16, where a follower is positioned in a neutral position of the barrel cam.

FIG. 22A shows follower pin (826) positioned in a neutral position (830) of barrel cam (816), prior to barrel cam (816) being rotated as will be discussed with reference to FIGS. 22B-22D. In neutral position (830), barrel cam (816) may be rotated clockwise or counterclockwise affecting the selected path of follower pin (826). Actuation body (814) is rotatably and translatably coupled with driven gear (324), and is configured to move similar to driven gear (324).

Figure 22B:
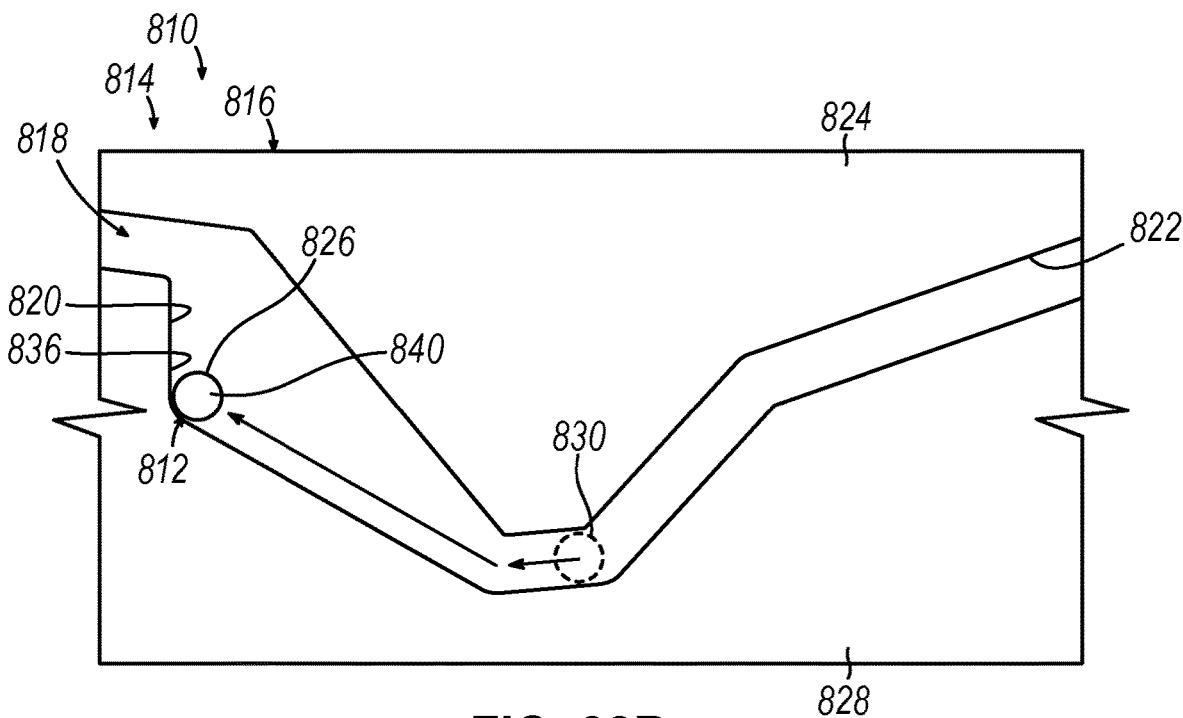
FIG. 22B depicts a schematic view of the follower moved along a first predetermined path of the barrel cam of FIG. 22A.

FIG. 22B shows a schematic view of follower pin (826) moved along first predetermined path (820) of barrel cam (816) from neutral position (830) to a first rotated position (840) along first predetermined path (820). As shown, first predetermined path (820) has a non-uniform width. Selection of first predetermined path (820) is configured to prevent actuation body (814) from accessing second predetermined path (822). However, selection of the second predetermined path (822) does not prevent follower pin (826) from accessing first predetermined path (820). This is because follower pin (826) is not rotatable into second predetermined path (822) without follower pin (826) overcoming a blocking feature (836), which is shown as a wall. End effector (214) is configured to perform a first actuation profile in response to movement of follower pin (826) due to actuation body (814) rotating follower pin (826) along first predetermined path (820). In some versions, the first actuation profile may allow a user to apply buttresses (410, 412) to at least one of lower and upper jaws (218, 220) of end effector (214). For example, buttresses (410, 412) may be applied to at least one of lower and upper jaws (218, 220) when surgical instrument (210) is not coupled with robotic arm (32), which is also referred to as an off-robot action.

Figure 22C:
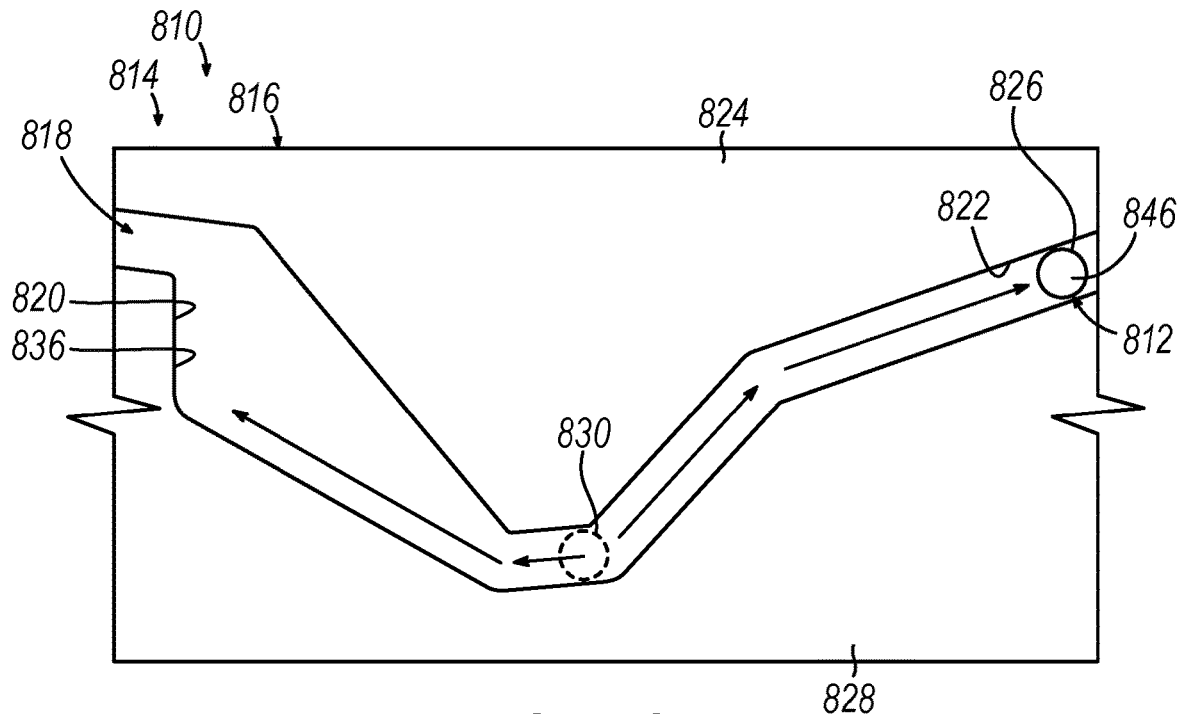
FIG. 22C depicts a schematic view of the follower moved along a second predetermined path of the barrel cam of FIG. 22A.

FIG. 22C shows a schematic view of follower pin (826) moved along second predetermined path (822) of barrel cam (816) of FIG. 22A. Alternatively, follower pin (826) may be rotated in the second direction to exit first predetermined path (820) and subsequently enter second predetermined path (822). In some versions, second actuation profile may manipulate tissue using robotic arm (32) of robotic surgical system (10) while surgical instrument (210) is coupled with robotic arm (32), also referred to as an on-robot action. More specifically, the second actuation profile may clamp and compress tissue between lower and upper jaws (218, 220) of end effector (214). The first and second actuation profiles may include other actions of end effector (214).

Figure 22D:
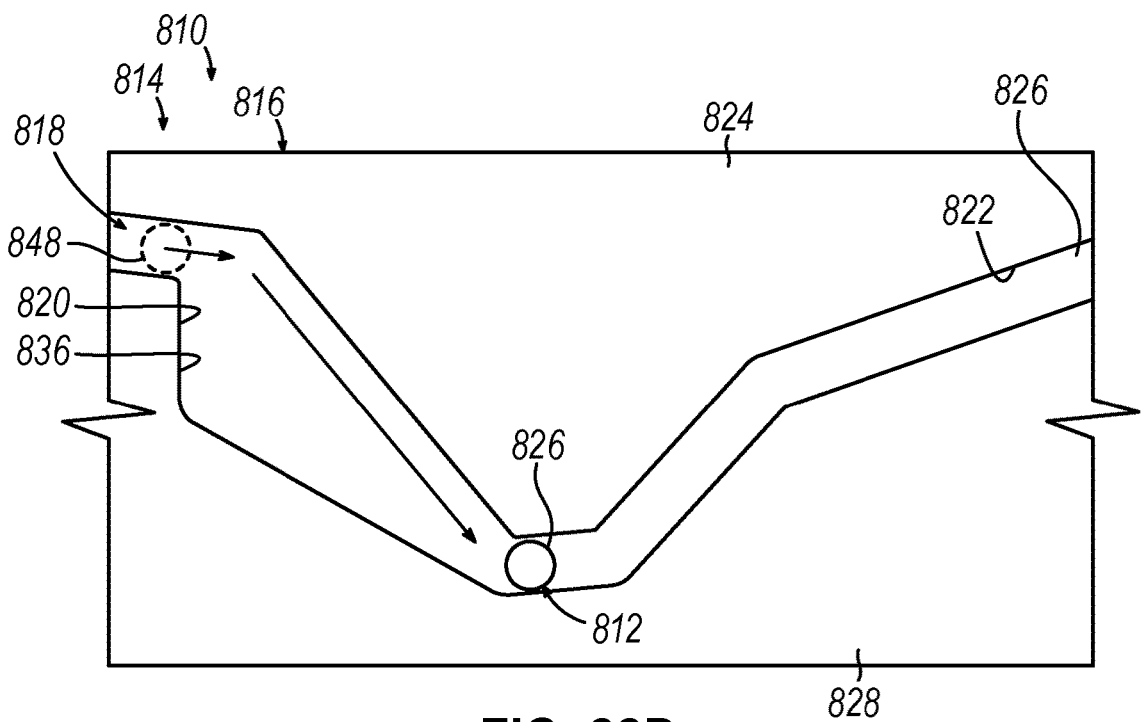
FIG. 22D depicts a schematic view of the follower moved along the first predetermined path of the barrel cam of FIG. 22B but in an opposite direction.

FIG. 22D shows a schematic view of follower pin (826) moved along first predetermined path (820) of barrel cam (816) of FIG. 22B but in an opposite direction, which may be used for bailout action to in a direction consistent for the user. As shown, follower pin (826) moves from a bailout position (848) to neutral position (830). This bailout action may open lower and upper jaws (218, 220). End effector (214) performs a second actuation profile in response to actuation body (814) moving along second predetermined path (822).

F. Fifth Exemplary Alternative Activating Mechanism

Figure 23:
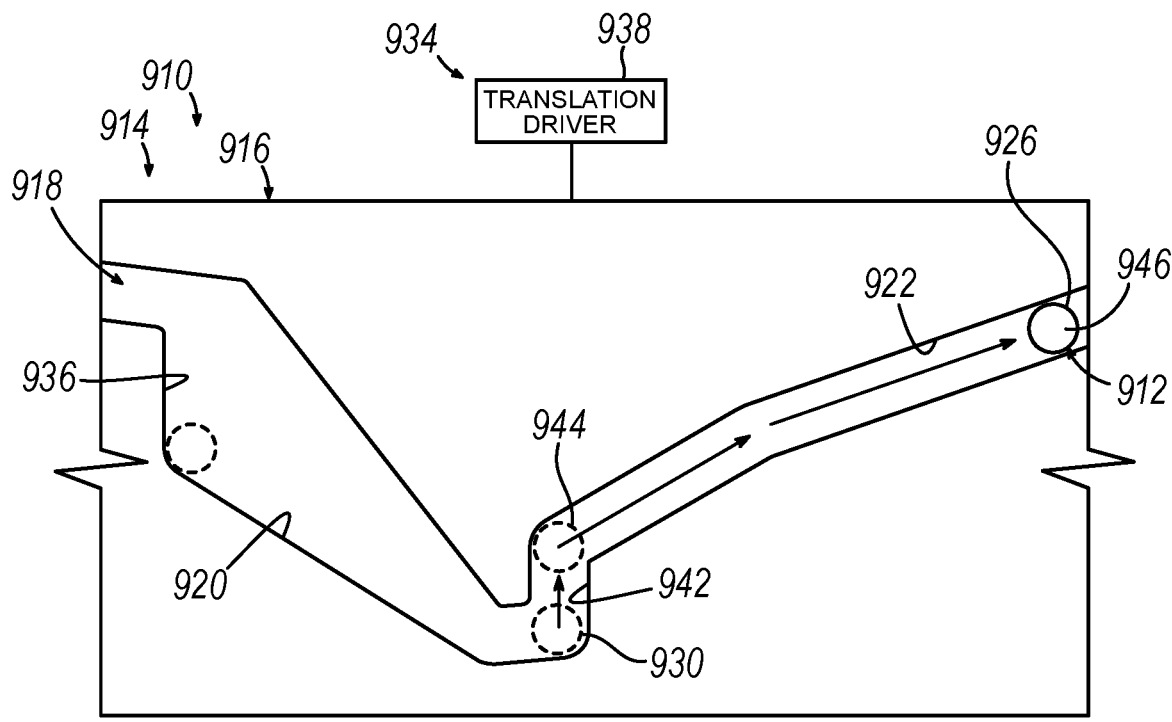
FIG. 23 depicts a schematic view of a portion of a fifth exemplary alternative activating mechanism that includes a portion of a barrel cam similar to FIG. 16, where a follower is moved along a predetermined path past a blocking feature of the barrel cam.

FIG. 23 show a schematic view of a portion of a fifth exemplary alternative activating mechanism (910) configured for use with carriage (310) of FIG. 13. Actuation body (914) of activating mechanism (910) includes a barrel cam (916), a portion of which is shown schematically in an un-rolled configuration in FIG. 23. In this embodiment, barrel cam (916) may be used instead of barrel cam (816). Similar to barrel cam (816), barrel cam (916) includes a continuous cam slot (918). Similar to continuous cam slot (918), continuous cam slot (918) includes first and second predetermined paths (920, 922).

Similar to drive (812), drive (912) may include closure tube (304) and at least one follower, shown as a follower pin (926). Follower pin (926) is similar to follower pin (826). Drive (912) may also include other suitable components. Follower pin (926) is configured to be received within continuous cam slot (918), such that continuous cam slot (918) guides movement of follower pin (926) as actuation body (914) moves along one of first and second predetermined paths (920, 922). Similar to follower pin (826) shown in FIG. 22B, follower pin (926) may be moved along first predetermined path (920) of barrel cam (916) from a neutral position (930) to a first rotated position (940) along first predetermined path (920). As shown, first predetermined path (920) has a non-uniform width. Selection of first predetermined path (920) is configured to prevent actuation body (914) from accessing second predetermined path (922). This is because follower pin (926) is not rotatable into second predetermined path (922) without follower pin (926) overcoming blocking feature (936). Similar to activating mechanism (910), end effector (214) is configured to perform a first actuation profile in response to movement of follower pin (926) due to actuation body (914) moving along first predetermined path (920).

Unlike activating mechanism (810), activating mechanism (910) includes a shifting mechanism (934) configured to direct actuation body (914) between first and second predetermined paths (920, 922). As shown, shifting mechanism (934) includes a translation driver (938), similar to translation driver (538) shown and described with reference to FIGS. 18A-18C. Follower pin (926) moved from a neutral position (930) to a translated position (944) along second predetermined path (922) of barrel cam (916).

FIG. 23 shows actuation body (914) translated distally and rotated. Translational driver (938) is engaged with actuation body (914) and is configured to selectively translate actuation body (914) causes follower pin (926) to move to translated position (944). Without this translation of actuation body (914), follower pin (926) cannot access second predetermined path (922) unlike second predetermined path (822). This is because access to second predetermined path (922) is restricted by blocking feature (942). Blocking feature (942), shown as a wall, is interposed between first and second predetermined paths (920, 922). Once follower pin (926) is in translated position (944), follower pin (926) may then be moved to a second rotated position (946) by rotating actuation body (914) which rotates barrel cam (916). However, selection of the second predetermined path (922) does not prevent the actuation body from accessing first predetermined path (920). Instead, selection of second predetermined path (922) allows actuation body (914) to access first predetermined path (920) by continuing to rotate actuation body (914) in the same direction so that follower pin (926) moves to first predetermined path (920) which is connected with second predetermined path (922). Similar to activating mechanism (910), end effector (214) performs a second actuation profile in response to actuation body (914) moving along second predetermined path (922).

G. Sixth Exemplary Alternative Activating Mechanism

Figure 24:
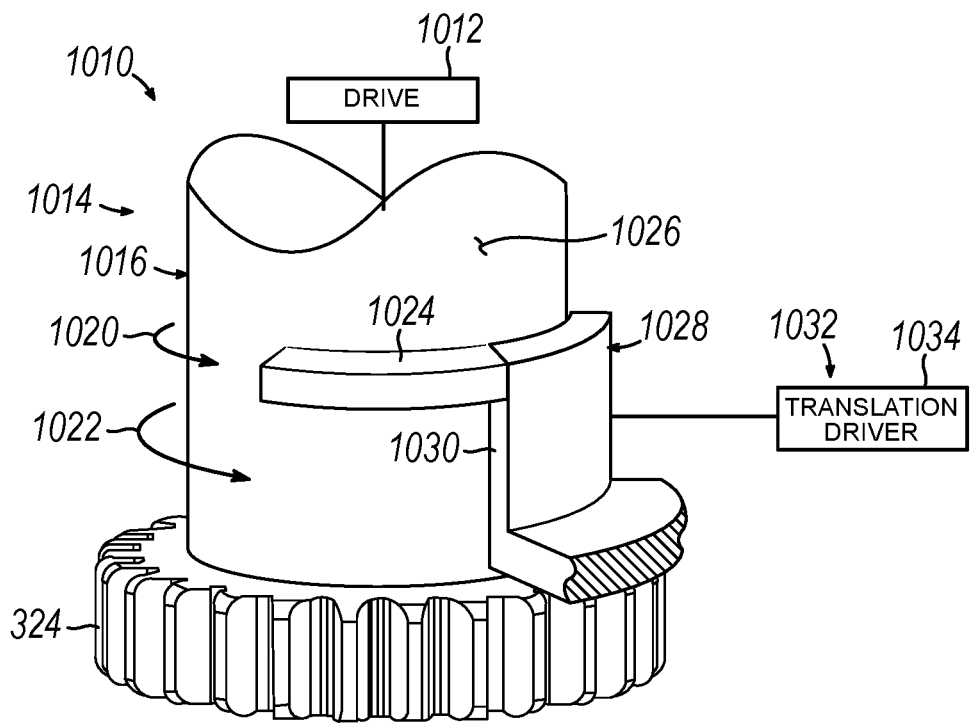
FIG. 24 depicts a schematic perspective view of a sixth exemplary alternative activating mechanism that includes an actuation body rotated into contact with a portion of a housing.
Figure 25A:
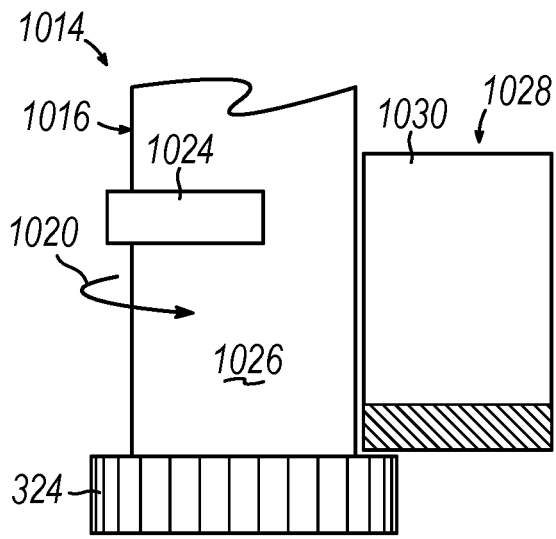
FIG. 25A depicts a schematic view of the activating mechanism and the housing of FIG. 24, but prior to the actuation body being rotated into contact with the housing.
Figure 25B:
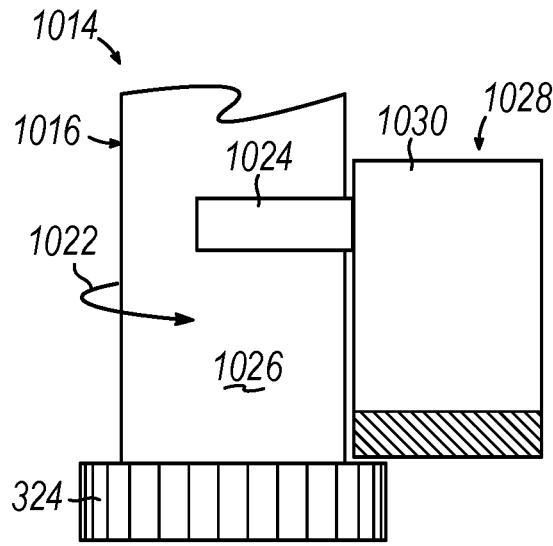
FIG. 25B depicts a schematic view of the activating mechanism and the housing of FIG. 25A, but after the actuation body is rotated into contact with the housing.

FIGS. 24-25B show a sixth exemplary alternative activating mechanism (1010) configured for use with carriage (310) of FIG. 13 instead of activating mechanism (362). Drive (1012) is operatively connected to a portion of end effector (214) or shaft assembly (212). Actuation body (1014) of activating mechanism (1010) includes a barrel cam (1016). Actuation body (1014) may move along first and second predetermined paths (1020, 1022).

Barrel cam (1016) extends parallel to a longitudinal axis (222) (see FIGS. 13-14) defined by shaft assembly (212). Barrel cam (1016) is configured to selectively rotate and selectively translate about longitudinal axis (222). Barrel cam (1016) includes one or more cam slots (not shown), but which may be similar to first and second cam profiles (380, 382) or cam slots (518, 618, 718, 818, 918). Barrel cam (1016) includes a projection (1024) extending radially outward from an outer surface (1026). Projection (1024) may be integrally formed with barrel cam (1016) or may be coupled to barrel cam (1016) Barrel cam (1016) is rotatably and translatably fixed relative to driven gear (324), similar to closure barrel (368). A housing (1028) may be formed with or coupled to shroud (278) shown in FIG. 7. Housing (1028) includes a projection (1030), shown in the form of a wall. Projection (1024) of barrel cam (1016) selectively contacts projection (1030) of housing (1028) as projection 1024) rotates relative to projection (1030) due to interaction with spline (242).

When carriage (310) is not fully inserted (e.g., fully retracted), barrel cam (1016) is translated so that projection (1024) of barrel cam (1016) is in-plane with projection (1030) extending from housing (1028). The interaction between projections (1024, 1030) enables rotation of barrel cam (1016) for the manual operation of first predetermined path (1020), for example during manual operation of surgical instrument (210) when surgical instrument (210) is not coupled with robotic arm (32), which is also referred to as an off-robot action. As a result, when surgical instrument (210) is off-robot, barrel cam (1016) may only be rotated in the desired manual range to access first predetermined path (1020). As shown in FIG. 25A, when carriage (310) is in a first position, projection (1030) is spaced from projection (1024). FIG. 25A shows a schematic view of activating mechanism (1010) and housing (1028) of FIG. 24, but prior to actuation body (1014) being rotated into contact with housing (1028). FIG. 25B depicts a schematic view of activating mechanism (1010) and housing (1028) of FIG. 25A, but after actuation body (1014) is rotated into contact with housing (1028). The user may be prevented from accessing second predetermined path (1022) or a portion thereof. End effector (214) is configured to perform a first actuation profile in response actuation body (1014) moving along first predetermined path (1020). In some versions, the first actuation profile may allow a user to apply buttresses (410, 412) to at least one of lower and upper jaws (218, 220) of end effector (214).

If carriage (310) is inserted into the patient for robotic operation, projection (1024) of barrel cam (1016) may rotate freely and access second predetermined path (1022). In other words, the interaction between projections (1024, 1030) enables access to second predetermined path (1022) for the robotic operation of surgical instrument (210). End effector (214) performs a second actuation profile in response to actuation body (1014) moving along second predetermined path (1022). In some versions, second actuation profile may manipulate tissue using robotic arm (32) of robotic surgical system (10) while surgical instrument (210) is coupled with robotic arm (32), also referred to as an on-robot action. More specifically, the second actuation profile may clamp and compress tissue between lower and upper jaws (218, 220) of end effector (214). The first and second actuation profiles may include other actions of end effector (214). In some versions, barrel cam (1016) may fit within the same footprint of closure barrel (368).

In some versions, activating mechanism (1010) includes an optional shifting mechanism (1032) configured to direct actuation body (1014) between first and second predetermined paths (1020, 1022). As shown, shifting mechanism (1032) includes a translation driver (1034) (see FIG. 24). Translational driver (1034) moves projection (1030) of housing (1028) between a blocking configuration and a non-blocking configuration. Projection (1030) of housing (1028) is configured to contact projection (1024) of barrel cam (1016) in the blocking configuration. Conversely, projection (1030) of housing (1028) is configured to not affect projection (1024) of barrel cam (1016) in the non-blocking configuration. Translational driver (1034) may provide a dedicated input from table-based robotic system (10 to block and enable rotation of barrel cam (1016) between the blocking configuration and the non-blocking configuration. Software may command projection (1030) of housing (1028) in and out of engagement with projection (1024) of barrel cam (1016).

Figure 26A:
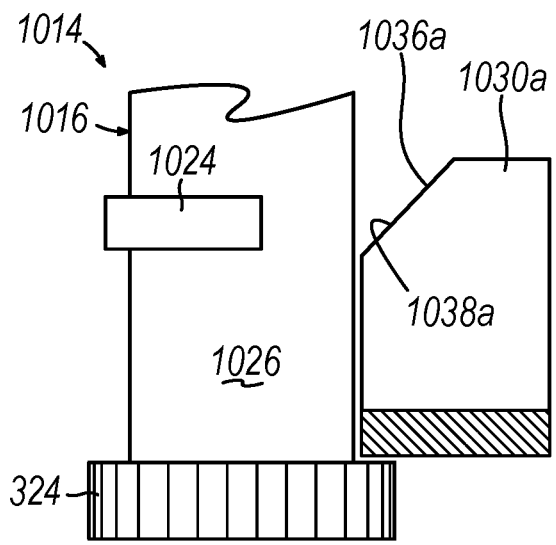
FIG. 26A depicts a schematic perspective view of activation body of FIG. 25A, but with the housing including a lead in portion spaced from the actuation body.
Figure 26B:
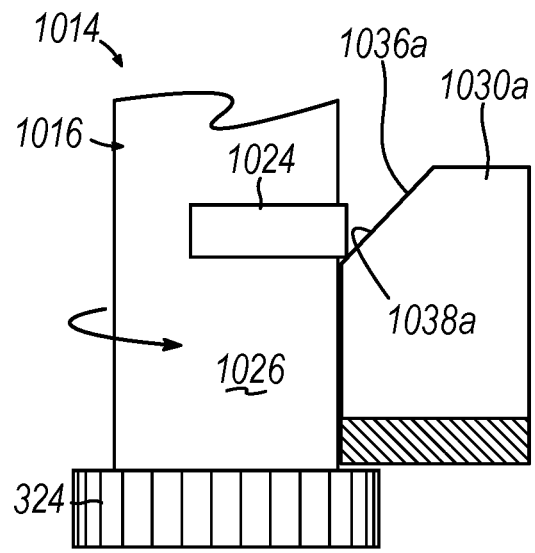
FIG. 26B depicts a schematic view of the of activation body of FIG. 26A, but after the actuation body is rotated into contact with the lead in portion of the housing.

In some versions, as shown in FIGS. 26A-26B, a contact surface (1036a) of a projection (1030a) may include a lead in portion (1038a) to assist in rotational alignment of projection (1024) of barrel cam (1016) with projection (1030a) of housing (1028). Projection (1030a) is generally otherwise similar to projection (1030). While not shown, projection (1024) may have a complementary lead in portion configured to align and contact lead in portion (1038a).

H. Seventh Exemplary Alternative Activating Mechanism

Figure 27A:
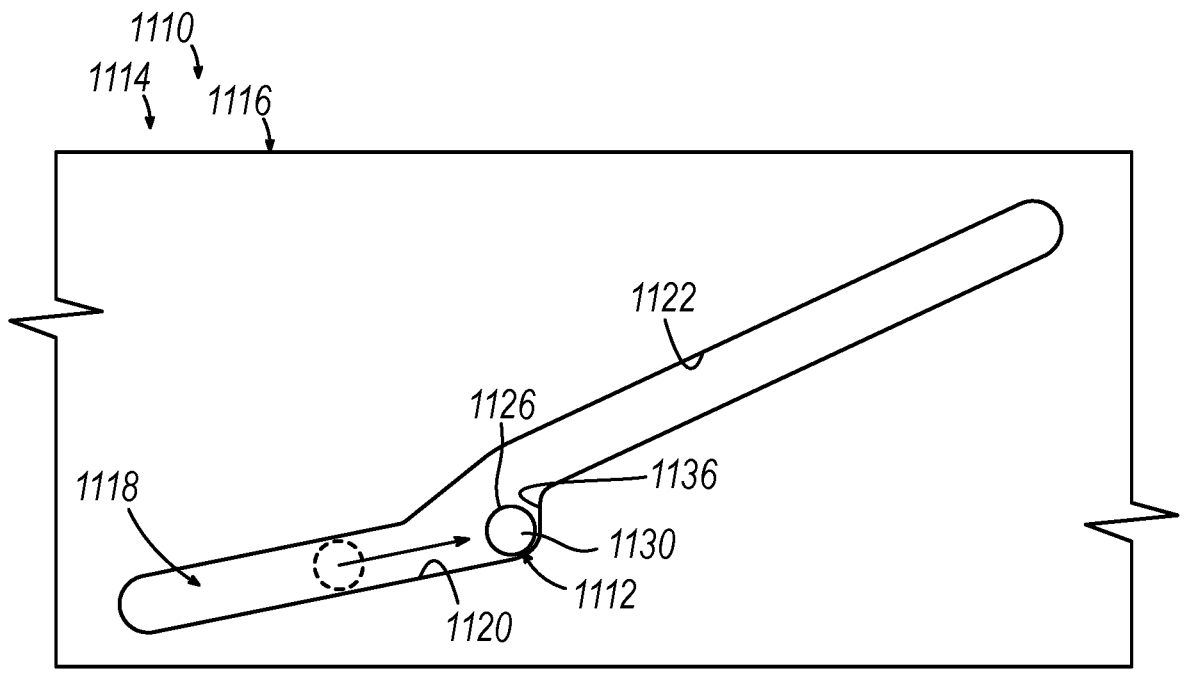
FIG. 27A depicts a schematic view of a seventh exemplary alternative activating mechanism that includes a portion of a barrel cam similar to FIG. 16, where a follower is moved along a first predetermined path against a blocking feature of the barrel cam.
Figure 27B:
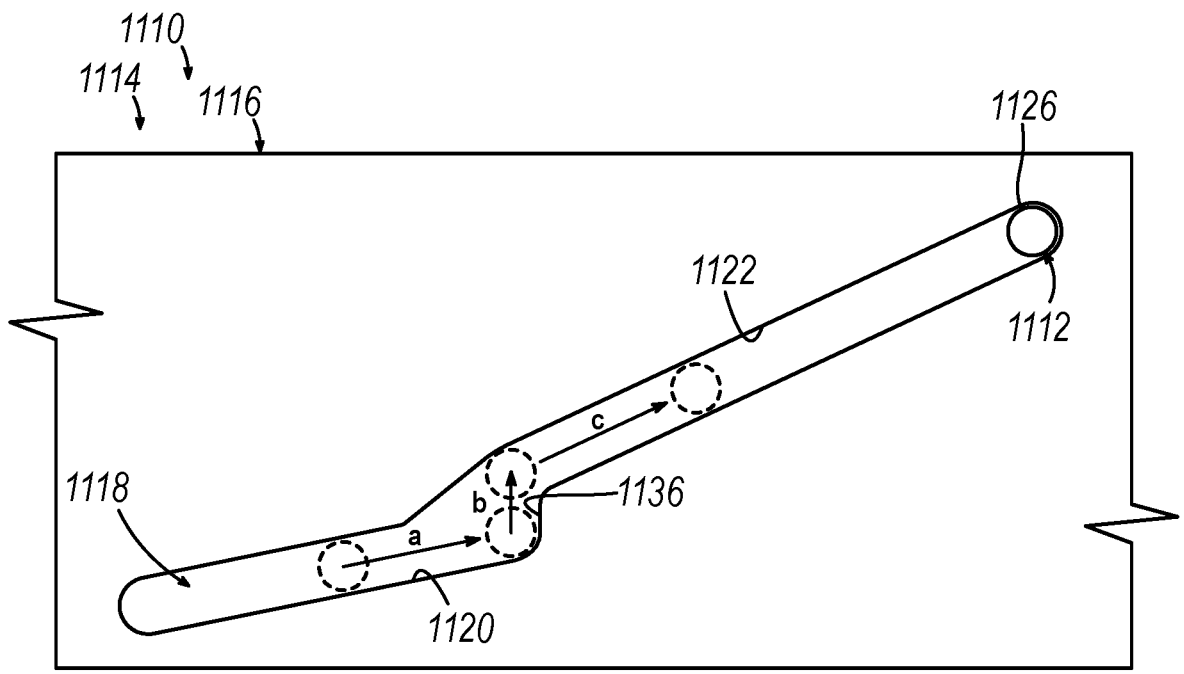
FIG. 27B depicts a schematic view of the follower moved along the first and second predetermined paths of the barrel cam of FIG. 27A, past the blocking feature of the barrel cam.
Figure 27C:
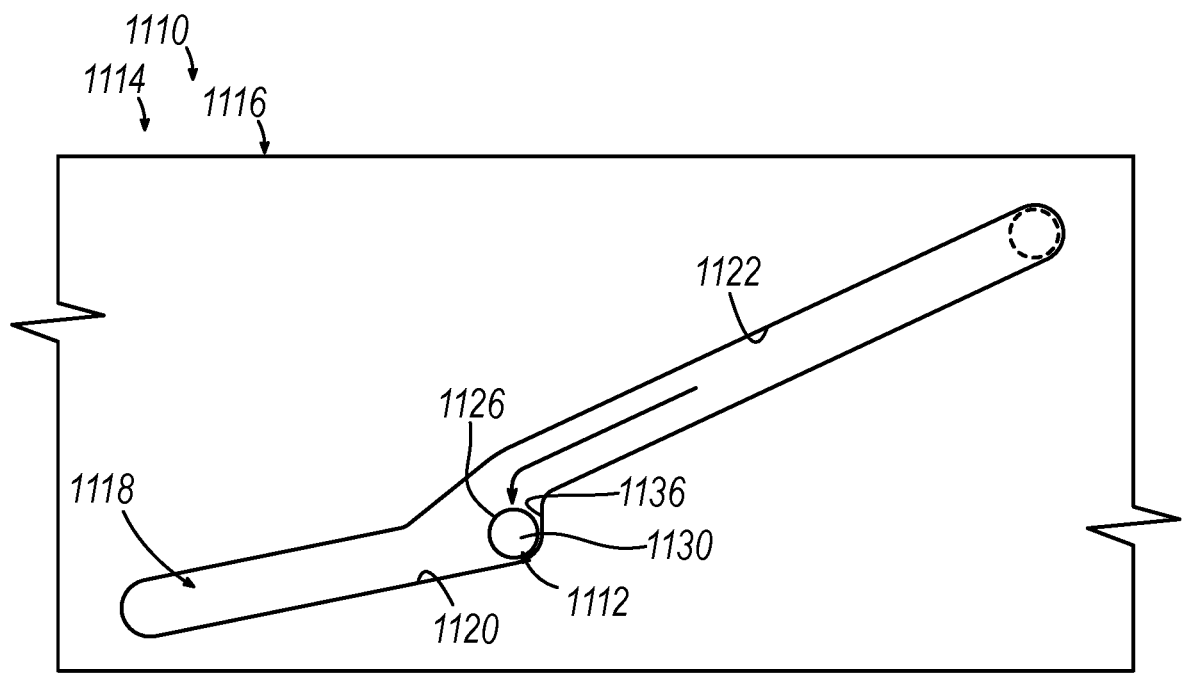
FIG. 27C depicts a schematic view of the follower moved along the second predetermined path of the barrel cam of FIG. 27B but in the opposite direction down the blocking feature.
Figure 28:
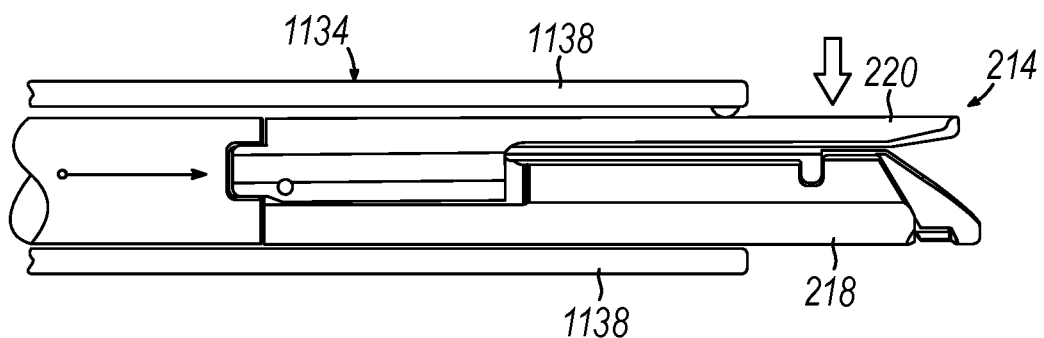
FIG. 28 depicts a schematic view of a nose cone moving the end effector of FIG. 8A to a closed configuration with the nose cone being configured for use with the activating mechanism of FIG. 27B.

FIGS. 27A-28 show schematic views of a portion of a seventh exemplary alternative activating mechanism (1110) configured for use with carriage (310) of FIG. 13. Actuation body (1114) of activating mechanism (1110) includes a barrel cam (1116), a portion of which is shown schematically in an un-rolled configuration in FIGS. 27A-27C. In this embodiment, barrel cam (1116) may be used instead of barrel cam (916). Similar to barrel cam (916) shown in FIGS. 22A-22D, barrel cam (1116) includes a cam slot (1118). Cam slot (1118) includes first and second predetermined paths (1120, 1122).

Similar to drive (912), drive (1112) may include a closure tube (similar to closure tube (304)) and at least one follower, shown as a follower pin (1126). Follower pin (1126) is similar to follower pin (926). Drive (1112) may also include other suitable components. Follower pin (1126) is configured to be received within cam slot (1118), such that cam slot (1118) guides movement of follower pin (1126) as actuation body (1114) moves follower pin (1126) along one of first and second predetermined paths (1120, 1122). First predetermined path (1120) is separated from second predetermined path (1122) using a blocking feature (1136), which is shown as a wall. As shown, first predetermined path (1120) has a non-uniform width. Similar to activating mechanism (1110), end effector (214) is configured to perform a first actuation profile in response to movement of follower pin (1126) due to actuation body (1114) moving along first predetermined path (1120). The user may close lower and upper jaws (218, 220) using an actuation mechanism (e.g., a manual closure knob), which positions follower pin (1126) at the end of first predetermined path (1120).

As shown in FIG. 27A, follower pin (1126) is moved along first predetermined path (1120) against blocking feature (1136) of barrel cam (1116) by rotating barrel cam (1116). The user is blocked from transitioning from first predetermined path (1120) (also referred to a manual portion) to second predetermined path (1122) (also referred to as powered portion) by blocking feature (1136). Blocking feature (1136) faces first predetermined path (1120) such that, when barrel cam (1116) is rotated through first predetermined path (1120) towards the second predetermined path (1122), follower pin (1126) is prevented by blocking feature (1136) from entering second predetermined path (1122). In other words, follower pin (1126) is not rotatable into second predetermined path (1122) without follower pin (1126) overcoming blocking feature (1136). However, follower pin (1126) may transition from second predetermined path (1122) to first predetermined path (1120) freely. In other words, when follower pin (1126) is in second predetermined path (1122) and moves toward first predetermined path (1120), follower pin (1126) may fall off blocking feature (1136) and enter first predetermined path (1120) uninhibited.

To overcome blocking feature (1136), activating mechanism (1110) includes a shifting mechanism (1134) as shown with additional reference to FIG. 28. Shifting mechanism (1134) is shown as including a nose cone (1138) configured to direct actuation body (1114) from first predetermined path (1120) to second predetermined path (1122). Nose cone (1138) moves lower and upper jaws (218, 220) to a closed configuration. To access second predetermined path (1122), the user may couple surgical instrument (210) with robotic arm (32) of table-based robotic system (10). Table-based robotic system (10) gains control to manipulate the insertion and closure axis. Table-based robotic system (10) may retract the insertion axis until lower and upper jaws (218, 220) of surgical instrument (210) collide with nose cone (1138). FIG. 28 shows the action of lower and upper jaws (218, 220) during this motion. The external collision pulls lower and upper jaws (218, 220) further closed, pulling follower pin (1126) up as shown in FIG. 27B, so that follower pin (1126) may overcomes blocking feature (1136). More specifically, this movement of nose cone (1138) allows follower pin (1126) to move from first predetermined path (1120) to second predetermined path (1122) when surgical instrument (210) is subjected to a series of movements (a, b, c). Table-based robotic system (10) may rotate barrel cam (1116), causing follower pin (1126) to move past blocking feature (1136) into second predetermined path (1122) of cam slot (1118). Similar to activating mechanism (1110), end effector (214) performs a second actuation profile in response to actuation body (1114) moving along second predetermined path (1122).

As shown in FIG. 27C, follower pin (1126) may transition from first predetermined path (1120) to second predetermined path (1122) under robotic control. Tension in the articulation system may pull the shaft allowing follower pin (1126) to overcome blocking feature (1136). Benefits of activating mechanism (1110) may include avoiding undesired user action with using blocking feature (1136) and complex robot action utilizes existing mechanisms and software. FIG. 27C shows a schematic view of follower pin (1126) moved along second predetermined path (1122) of barrel cam (1116) of FIG. 27B but in opposite direction toward blocking feature (1136).

I. Eighth Exemplary Alternative Activating Mechanism

Figure 29A:
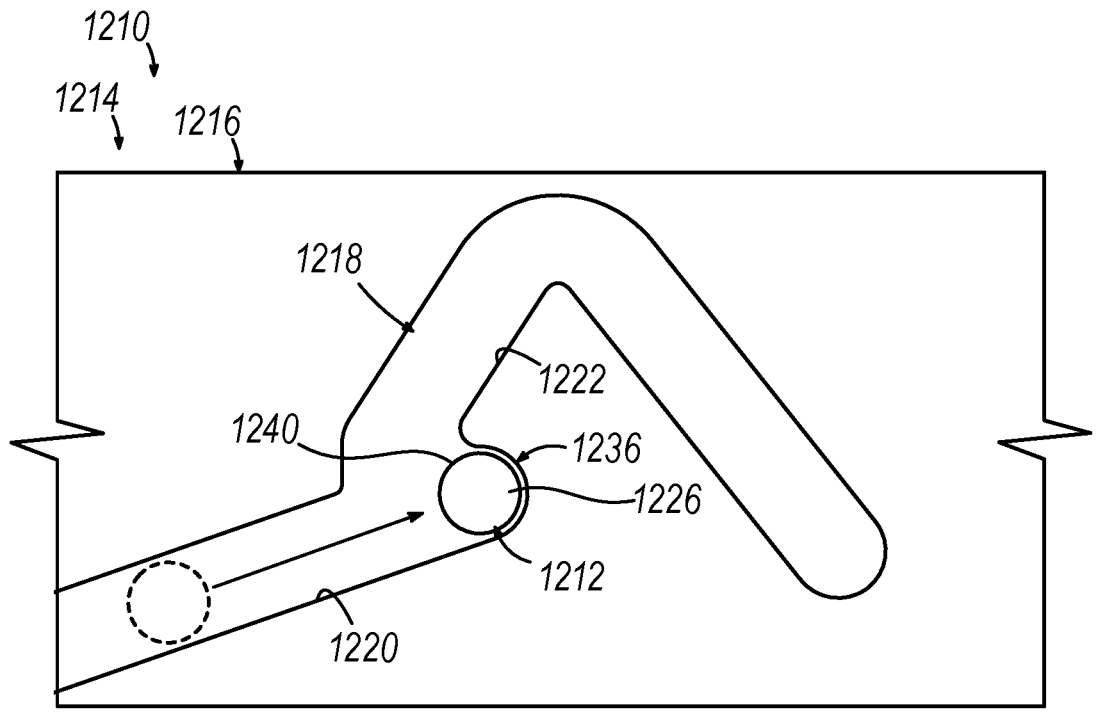
FIG. 29A depicts a schematic view of an eighth exemplary alternative activating mechanism that includes a barrel cam, where a follower is moved along a first predetermined path against a blocking feature of the barrel cam.
Figure 29B:
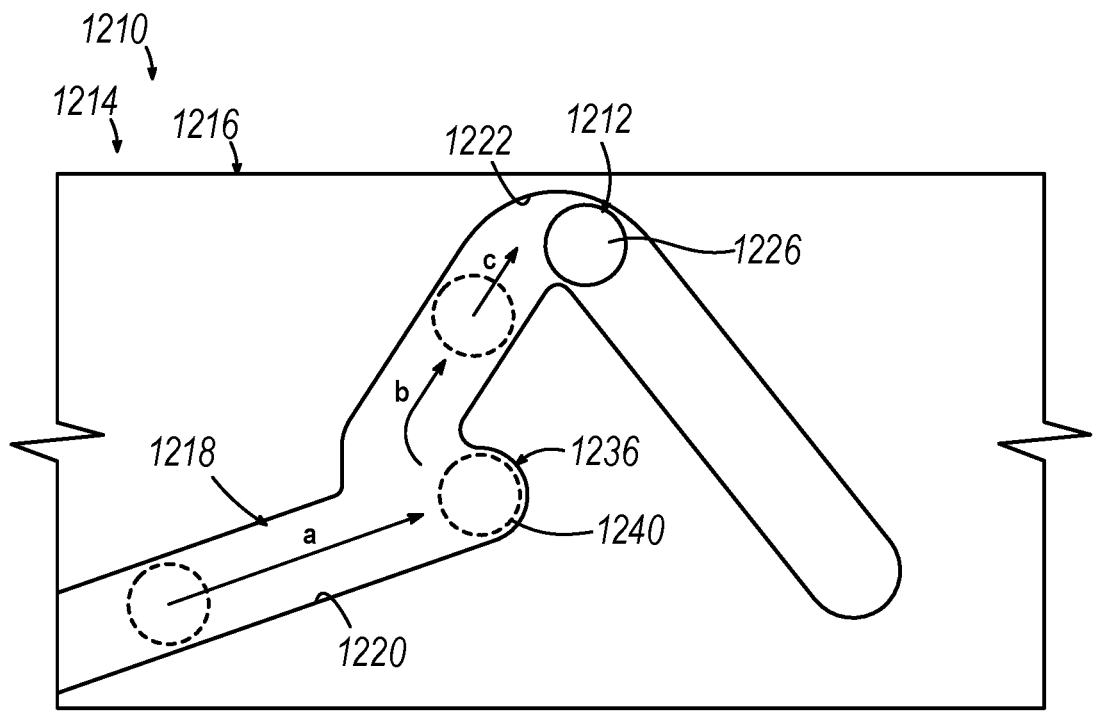
FIG. 29B depicts a schematic view of the follower moved along first and second predetermined paths of the barrel cam of FIG. 29A.

FIGS. 29A-29B show schematic views of a portion of an eighth exemplary alternative activating mechanism (1210) configured for use with carriage (310) of FIG. 13. Actuation body (1214) of activating mechanism (1210) includes a barrel cam (1216), a portion of which is shown schematically in an un-rolled configuration in FIGS. 29A-29B. In this embodiment, barrel cam (1216) may be used instead of barrel cam (1116). Similar to barrel cam (1116) shown in FIGS. 27A-27C, barrel cam (1216) includes a cam slot (1218). Cam slot (1218) includes first and second predetermined paths (1220, 1222).

Follower pin (1226) is similar to follower pin (1126). Follower pin (1226) is configured to be received within cam slot (1218), such that cam slot (1218) guides movement of follower pin (1226) as actuation body (1214) moves along one of first and second predetermined paths (1220, 1222). First predetermined path (1220) is separated from second predetermined path (1222) using a blocking feature (1236), which is shown as a wall. Unlike blocking feature (1136), blocking feature (1236) includes an overhang portion (1240). Overhang portion (1240) may allow follower pin (1226) to move from first predetermined path (1220) (also referred to a manual portion) to second predetermined path (1222) (also referred to as powered portion) under a sufficiently high user load.

As shown in FIG. 29A, follower pin (1226) is moved along first predetermined path (1220) against blocking feature (1236) of barrel cam (1216) by rotating barrel cam (1216). In some versions, this overhang portion (1240) may provide a tactile indication to ensure buttresses (410, 412) are fully applied. Similar to follower pin (1126), follower pin (1226) is not rotatable into second predetermined path (1222) without follower pin (1226) overcoming blocking feature (1236). The user is blocked from transitioning from first predetermined path (1220) to second predetermined path (1222) by blocking feature (1236). However, this blocking feature (1236) may be overcome.

To overcome blocking feature (1236), activating mechanism (1210) includes a shifting mechanism (not shown) but which may be similar to shifting mechanism (1134). For example, the shifting mechanism may include a nose cone similar to nose cone (1138) or a translation driver similar to translation driver (938). To access second predetermined path (1222), the user may couple surgical instrument (210) with robotic arm (32) of table-based robotic system (10). Movement of a nose cone (not shown) but which may be similar to nose cone (1138) may allow follower pin (1226) to move from first predetermined path (1220) to second predetermined path (1222) when surgical instrument (210) is subjected to a series of movements (a, b, c). Similar to activating mechanism (1110), end effector (214) performs a second actuation profile in response to actuation body (1214) moving along second predetermined path (1222).

J. Ninth Exemplary Alternative Activating Mechanism

FIGS. 30A-32B show schematic views of a ninth exemplary alternative activating mechanism (1310) configured for use with carriage (310) of FIG. 13 instead of activating mechanism (362). Similar to actuation body (614), actuation body (1314) of activating mechanism (1310) includes a barrel cam (1316), similar to barrel cam (616). Barrel cam (1316) includes a cam slot (1318). Cam slot (1318) includes first and second predetermined paths (1320, 1322) as well as a connecting portion (1324) interposed between first and second predetermined paths (1320, 1322). First and second predetermined paths (1320, 1322) overlap at connecting portion (1324). Connecting portion (1324) may be considered a full-open position.

First and second predetermined paths (1320, 1322) have different paths of different diameter and depths. First predetermined path (1320) has a first width (W1) and a first thickness (T1). Second predetermined path (1322) has a second width (W2) and a second thickness (T2). First thickness (T1) is greater than second thickness (T2), and second width (W2) is less than first width (W1). First predetermined path (1320), which has a larger diameter and is cut shallower into barrel cam (1316). Second predetermined path (1322), which in some versions may be used for teleoperation, has a smaller diameter and is cut deeper into barrel cam (1316).

Similar to drive (612), drive (1312) is operatively connected to a portion of end effector (214) or shaft assembly (212). Drive (1312) may include closure tube (304) and at least one follower, shown as a follower pin (1326). Follower pin (1326) is shown in the form of a yoke pin. Activating mechanism (1310) includes a shifting mechanism (1330) configured to direct actuation body (1314) between first and second predetermined paths (1320, 1322). Similar to shifting mechanism (636) shown in FIGS. 19A-19C, shifting mechanism (1330) includes a housing (1342). In some versions, housing (1342) may be formed with or coupled to shroud (278) shown in FIG. 7. Follower pin (1326) includes first portion (1332) having a first diameter, a second portion (1334) having a second diameter, and a third portion (1336) having a third diameter. Third diameter is greater than second diameter, and second diameter is greater than first diameter. A biasing member, shown as coil spring (1338), extends around the circumference of second portion (1334). Coil spring (1338) abuts a wall (1340) of third portion (1336). As barrel cam (1316) rotates, follower pin (1326) translates within the predetermined path and closes lower and upper jaws (218, 220) of end effector (214). The closure spline may be turned with ADM motors or a manual open/close knob (not shown) (off-robot compared to teleoperation) and a shift in radius of follower pin (1326) to transition between first and second predetermined paths (1320, 1322).

Figure 30B:
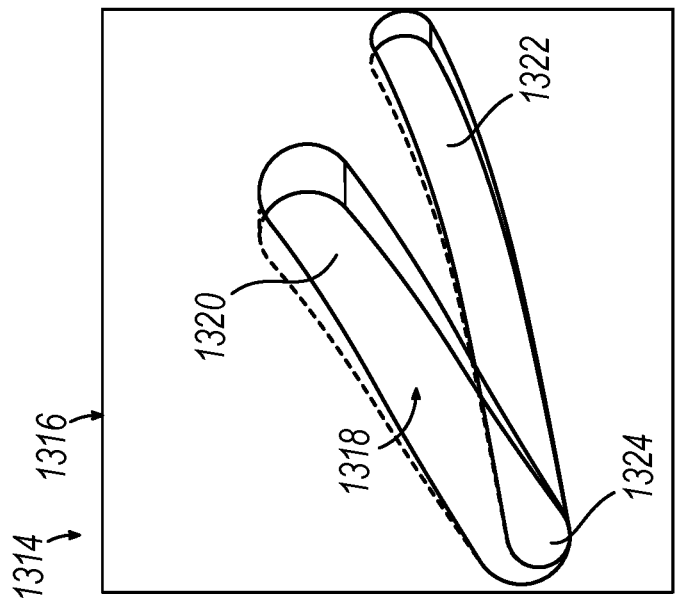
FIG. 30B depicts a perspective view of the barrel cam of FIG. 30A.
Figure 30A:
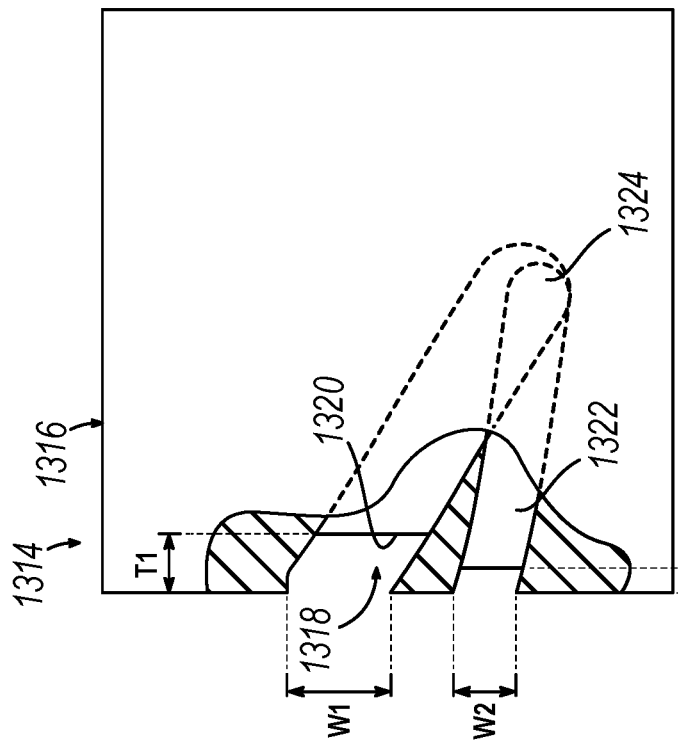
FIG. 30A depicts a partial cross-sectional view of a ninth exemplary alternative activating mechanism that includes a barrel cam with first and second predetermined paths.
Figure 31B:
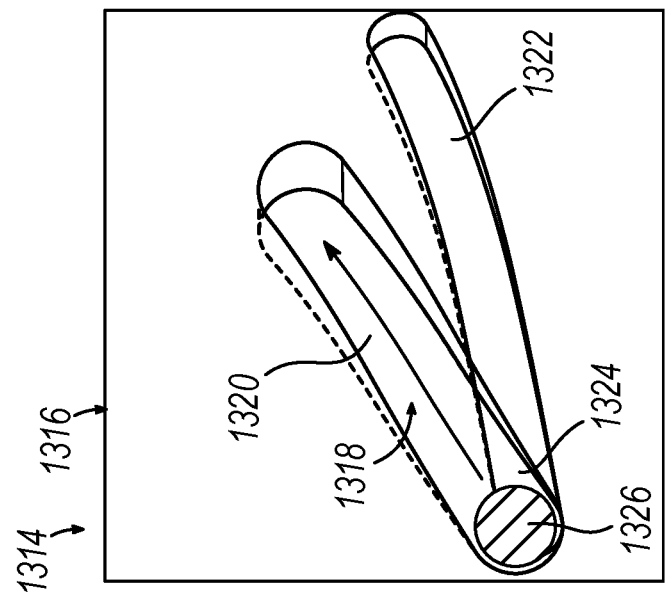
FIG. 31B depicts a partial cross-sectional perspective view of the follower and the barrel cam of FIG. 31A.
Figure 31A:
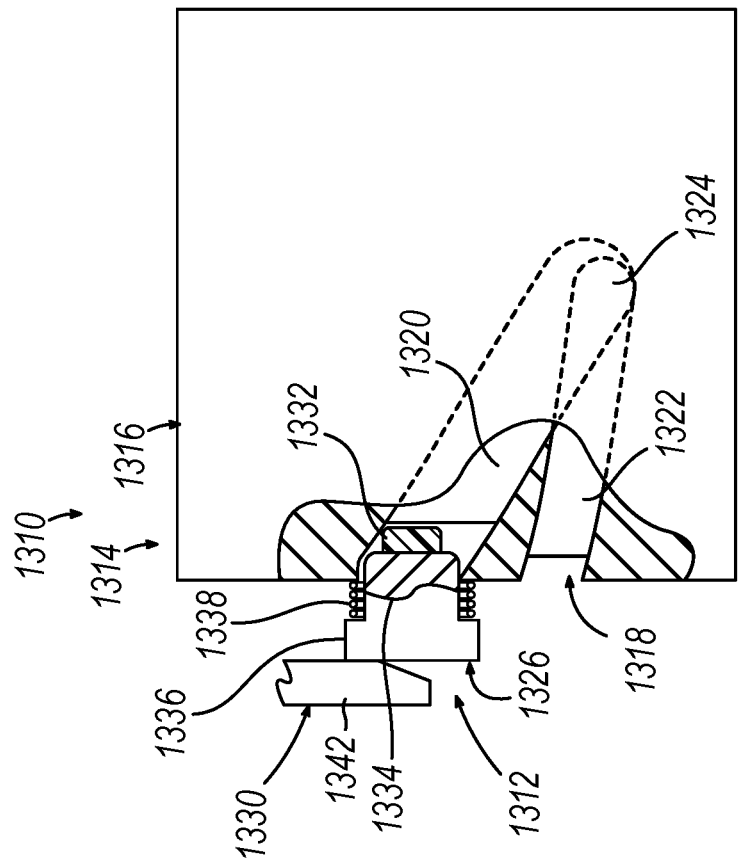
FIG. 31A depicts a partial cross-sectional view of a follower being guided by a housing to the first predetermined path of FIG. 30A.

FIG. 31A shows a partial cross-sectional view of follower pin (1326) being pushed by housing (1342) within first predetermined path (1320) of FIG. 30A, and FIG. 31B shows a partial cross-sectional perspective view of follower pin (1326) and barrel cam (1316) of FIG. 31A. As shown in FIG. 31A-31B, second portion (1334) of follower pin (1326) moves along first predetermined path (1320). In some versions, first predetermined path (1320) may be used for off robot application (e.g., to manually apply one or more buttresses (410, 412). While not coupled with table-based robotic system (10), a housing (1342) from insertion maintains coil spring (1338) of follower pin (1326) in a compressed position. As shown in FIG. 31A, housing (1342) pushes follower pin (1326) into first predetermined path (1320), so that coil spring (1338) moves to a compressed configuration. Follower pin (1326) is spring biased away from first predetermined path (1320). This causes second portion (1334) of follower pin (1326) to interface with first predetermined path (1320) which has larger diameter and deeper path of cam slot (1318), which may be optimized for manual (e.g., off-robot) actions.

Figure 32B:
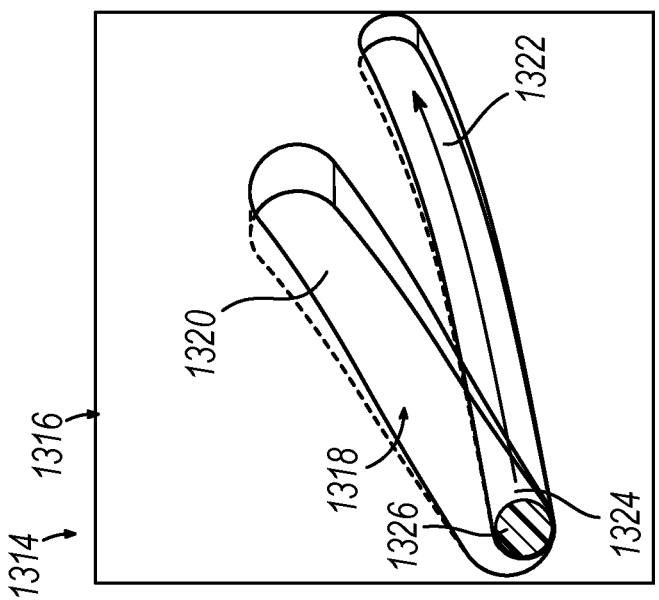
FIG. 32B depicts a partial cross-sectional perspective view of the follower and the barrel cam of FIG. 32A.
Figure 32A:
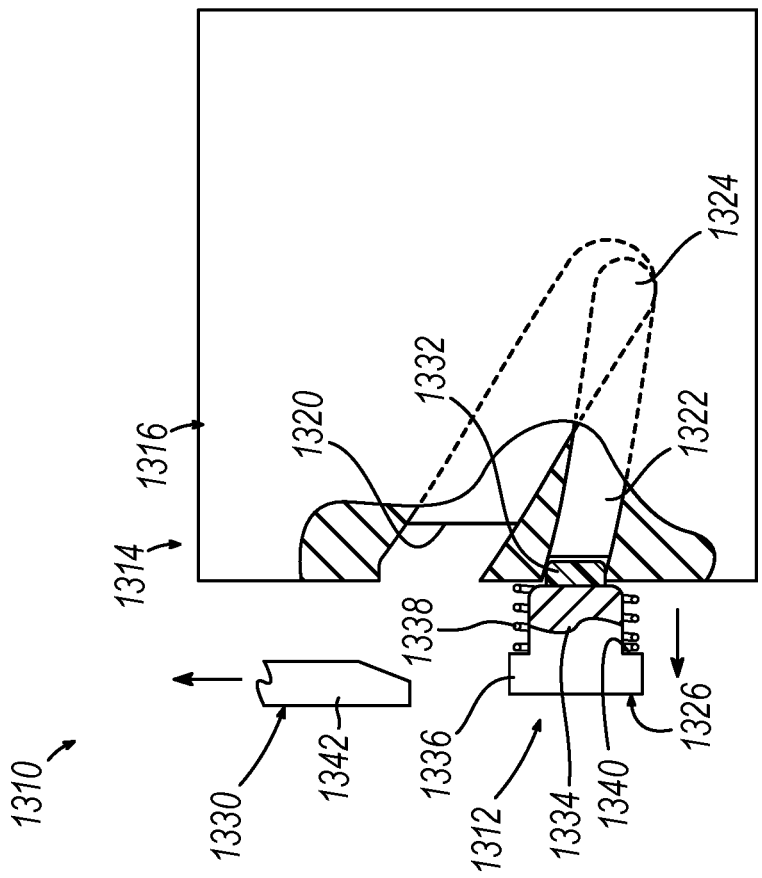
FIG. 32A depicts a partial cross-sectional view of a follower being guided to the second predetermined path of FIG. 30A.

FIG. 32A shows a partial cross-sectional view of follower pin (1326) being pushed by a housing (1342) within second predetermined path (1322) of FIG. 30A, and FIG. 32B shows a partial cross-sectional perspective view of follower pin (1326) and barrel cam (1316) of FIG. 32A. Second predetermined path (1322) may be used for robotic operations, also referred to as teleoperation, when surgical instrument (210) is coupled with robotic arm (32). When the surgical instrument (210) is coupled with table-based robotic system (10), housing (1342) moves out of the way. As shown in FIG. 30A, housing (1342) moves out of the way, so that follower pin (1326) moves radially outward. In other words, first portion (1332) of follower pin (1326) now interfaces with second predetermined path (1322) that has a smaller diameter and shallower path of cam slot (1318), which may be optimized for teleoperation. Benefits of activating mechanism (1310) may include creating two or more zones for multiple uses, leveraging different directions of turning in cam slot (1318), utilizing a single mechanism, and using compact packaging. This allows follower pin (1326) to move radially outward to an extended position. During removal of surgical instrument (210), housing (1342) may reset the position of follower pin (1326) for off-robot use.

K. Tenth Exemplary Alternative Activating Mechanism

Figure 33:
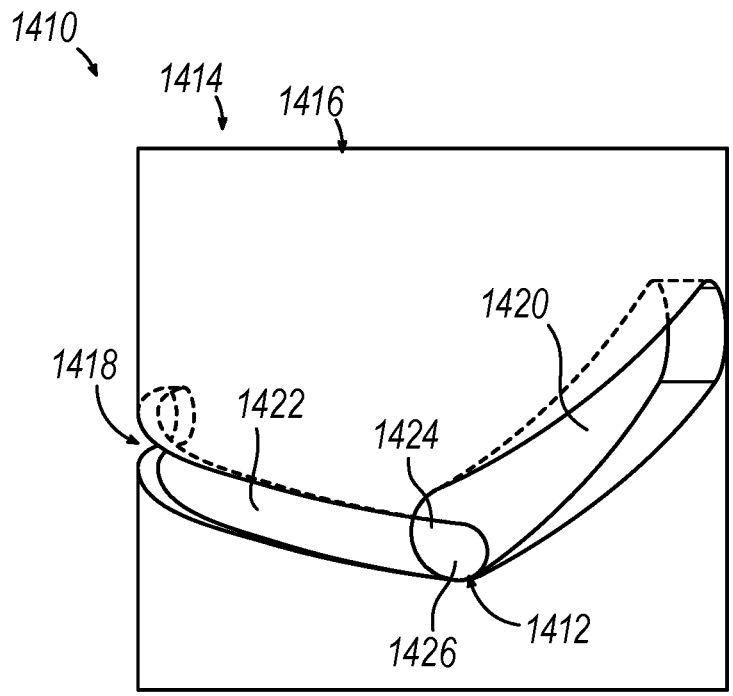
FIG. 33 depicts a perspective view of a tenth exemplary alternative activating mechanism that includes a barrel cam with first and second predetermined paths.
Figure 34:
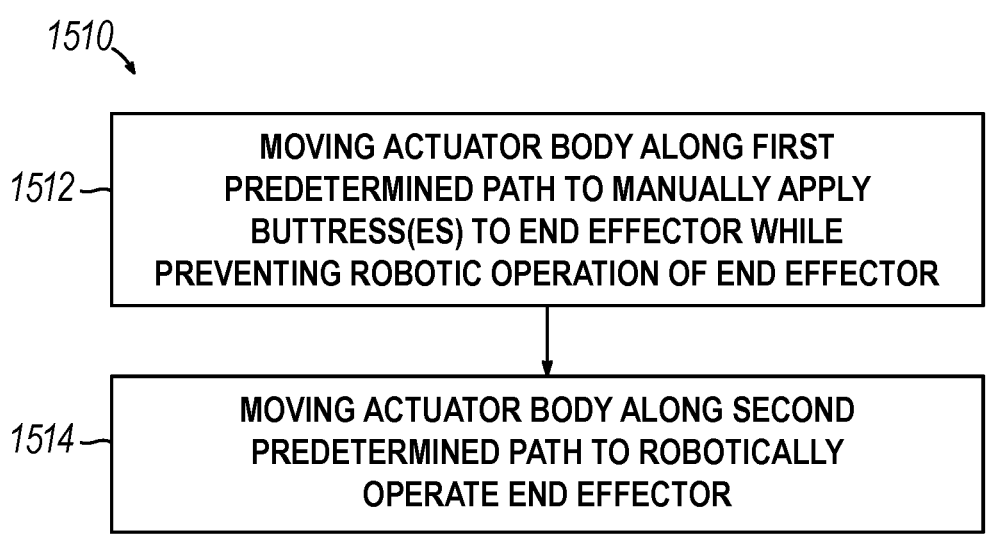
FIG. 34 depicts a diagrammatic view of an exemplary method of operating the table-based robotic system of FIG. 1.

FIG. 33 show a schematic view of a tenth exemplary alternative activating mechanism (1410) configured for use with carriage (310) of FIG. 13 instead of activating mechanism (362). Similar to actuation body (1314), actuation body (1414) of activating mechanism (1410) includes a barrel cam (1416). Barrel cam (1416) includes a cam slot (1418) similar to cam slot (1318) which is configured to receive a follower pin (1426), similar to follower pin (1326). Cam slot (1418) includes first and second predetermined paths (1420, 1422) as well as a connecting portion (1424) interposed between first and second predetermined paths (1420, 1422). First and second predetermined paths (1420, 1422) overlap at connecting portion (1424), which may also be considered a full-open position. As shown, first and second predetermined paths (1420, 1422) are diverging.

First and second predetermined paths (1420, 1422) have different diameters and different depths. First predetermined path (1420) has a first width (W1), and second predetermined path (1422) has a second width (W2) that is lesser than first width (W1). First predetermined path (1420), which in some versions may be used for off robot application, has a larger diameter and is cut shallower similar to first predetermined path (1320). Second predetermined path (1422), which in some versions may be used for teleoperation, has a smaller diameter and is cut deeper similar to second predetermined path (1322). The operation of barrel cam (1416) is similar to the operation of barrel cam (1316) described above with reference to FIGS. 30A-32B.

L Exemplary Method

A method (1510) of operating surgical instrument (210) of a robotic surgical system (10) is also described. At step (1512), method (1510) includes moving actuation body (514, 614, 714, 814, 914, 1014, 1114, 1214, 1314, 1414) of activating mechanism (510, 610, 710, 810, 910, 1010, 1110, 1210, 1310, 1410) along first predetermined path (520, 620, 720, 820, 920, 1020, 1120, 1220, 1320, 1420) to manually apply a buttress (410, 412) to at least one of lower and upper jaws (218, 220) of end effector (214) while preventing robotic operation of end effector (214). In other words, end effector (214) performs the first actuation profile in response to actuation body (514, 614, 714, 814, 914, 1014, 1114, 1214, 1314, 1414) moving along a first predetermined path (520, 620, 720, 820, 920, 1020, 1120, 1220, 1320, 1420). Selection of first predetermined path (520, 620, 720, 820, 920, 1020, 1120, 1220, 1320, 1420) is configured to prevent actuation body (514, 614, 714, 814, 914, 1014, 1114, 1214, 1314, 1414) from accessing second predetermined path (522, 622, 722, 822, 922, 1022, 1122, 1222, 1322, 1422).

At step (1514), method (1510) includes moving actuation body (514, 614, 714, 814, 914, 1014, 1114, 1214, 1314, 1414) along a second predetermined path (522, 622, 722, 822, 922, 1022, 1122, 1222, 1322, 1422) to robotically operate end effector (214) of surgical instrument (210) of a robotic surgical system, such as table-based robotic system (10). In other words, end effector (214) is configured to perform the second actuation profile in response to actuation body (514, 614, 714, 814, 914, 1014, 1114, 1214, 1314, 1414) moving along second predetermined path (522, 622, 722, 822, 922, 1022, 1122, 1222, 1322, 1422). In some versions, second actuation profile may manipulate tissue using robotic arm (32) of table-based robotic system (10). More specifically, the second actuation profile may clamp and compress tissue between lower and upper jaws (218, 220) of end effector (214). The first and second actuation profiles may include other actions of end effector (214).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector comprising: (i) a first jaw, and (ii) a second jaw, wherein at least one of the first and second jaws is pivotable relative to the other of the first and second jaws between an open position and a closed position; (b) a shaft assembly extending proximally from the end effector, wherein the shaft assembly defines a longitudinal axis; (c) a drive operatively connected to a portion of at least one of the end effector or the shaft assembly; and (d) an activating mechanism including an actuation body operatively connected to the drive, wherein the portion is configured to perform a first actuation profile in response to the actuation body moving along a first predetermined path or perform a second actuation profile in response to the actuation body moving along a second predetermined path, wherein selection of the first predetermined path is configured to prevent the actuation body from accessing the second predetermined path.

Example 2

The surgical instrument of Example 1, wherein selection of the second predetermined path is configured to prevent the actuation body from accessing the first predetermined path.

Example 3

The surgical instrument of any one or more of Examples 1 through 2, wherein the drive includes a follower, wherein the actuation body includes a cam slot, and wherein the follower is configured to be received within the cam slot such that the cam slot guides movement of the follower as the actuation body moves along the first or second predetermined paths.

Example 4

The surgical instrument of Example 3, wherein the actuation body includes a barrel cam having the cam slot that forms the first and second predetermined paths, wherein the barrel cam extends parallel to the longitudinal axis and configured to selectively rotate about the longitudinal axis, and wherein the barrel cam is further configured to selectively translate along the longitudinal axis.

Example 5

The surgical instrument of Example 4, wherein the first and second predetermined paths collectively extend continuously around the entire circumference of the barrel cam.

Example 6

The surgical instrument of Example 4, further comprising a housing that includes a first projection, wherein the barrel cam includes a second projection that is configured to selectively contact the first projection as at least one of the first or second projections rotates relative to the other of the first or second projections.

Example 7

The surgical instrument of Example 6, wherein the second projection extends outwardly from an outer surface of the barrel cam.

Example 8

The surgical instrument of any one or more of Examples 6 through 7, wherein the first projection includes a lead in portion configured to assist in rotational alignment of the first and second projections.

Example 9

The surgical instrument of any one or more of Examples 4 through 8, further comprising an actuator configured to move one of the first or second projections between a blocking configuration and a non-blocking configuration, wherein the second projection is configured to contact the first projection in the blocking configuration, and wherein the second projection is configured to not contact the first projection in the non-blocking configuration.

Example 10

The surgical instrument of any one or more of Examples 1 through 9, further comprising a shifting mechanism configured to direct the actuation body between the first and second predetermined paths.

Example 11

The surgical instrument of Example 10, further comprising a hard stop interposed between the first and second predetermined paths and configured to be overcome by activating the shifting mechanism.

Example 12

The surgical instrument of any one or more of Examples 9 through 11, wherein the shifting mechanism includes a longitudinally extending portion extending parallel to the longitudinal axis, wherein the longitudinal slot connects the first and second predetermined paths.

Example 13

The surgical instrument of any one or more of Examples 10 through 12, wherein the surgical instrument comprises a housing and a carriage configured to move along the housing, wherein the shifting mechanism includes a wedge configured to move between first and second positions and thereby adjust the actuation body between the first and second predetermined paths, wherein in the disengaged position the actuation body is configured to travel along the first predetermined path, wherein in the engaged position the actuation body is configured to travel along the second predetermined path.

Example 14

The surgical instrument of Example 13, wherein the wedge includes a thin forked portion, a thick forked portion and a ramp, wherein the ramp is configured to engage the housing in the engaged position when the carriage is in a first position, wherein the wherein the ramp is configured to not engage the housing in the engaged position when the carriage is in second position and the first predetermined path.

Example 15

The surgical instrument of any one or more of Examples 13 through 14, wherein the wedge is biased toward the housing using a first biasing mechanism, wherein the cam is biased distally using a second biasing mechanism.

Example 16

The surgical instrument of any one or more of Examples 1 through 15, wherein the activating mechanism further includes a translational driver, wherein the translational driver is engaged with the actuation body and configured to selectively translate the actuation body from a first translational body position, toward a second translational body position.

Example 17

The surgical instrument of any one or more of Examples 1 through 16, wherein the surgical instrument includes a robotic arm, wherein the first actuation profile is configured to apply a buttress to at least one of the first and second jaws of the end effector, wherein the second actuation profile is configured to clamp tissue between the first and second jaws of the end effector.

Example 18

The surgical instrument of any one or more of Examples 1 through 17, further compressing a drive gear, wherein the actuation body includes a driven gear configured to be rotated by the drive gear, wherein the actuation body is rotatably and translatably coupled with the driven gear.

Example 19

The surgical instrument of any one or more of Examples 1 through 18, wherein the first predetermined path has a non-uniform width.

Example 20

The surgical instrument of any one or more of Examples 1 through 19, wherein the surgical instrument comprises a housing and a carriage configured to move along the housing, wherein the carriage is movably mounted to at least one spline, wherein the elongate shaft extends distally from the carriage.

Example 21

A robotic surgical system comprising: (a) a robotic arm; and (b) a surgical instrument configured removably coupled with the robotic arm; (i) an end effector; (ii) a shaft assembly extending proximally from the end effector, wherein the shaft assembly defines a longitudinal axis; (iii) a drive operatively connected to a portion of at least one of the end effector or the shaft assembly; and (iv) an activating mechanism including an actuation body operatively connected to the drive, wherein the portion is configured to perform a first actuation profile in response to the actuation body moving along a first predetermined path for applying at least one buttress to the end effector or perform a second actuation profile in response to the actuation body moving along a second predetermined path for manipulating tissue using the robotic arm of the robotic surgical system, wherein selection of the second predetermined path is configured to prevent the actuation body from accessing the first predetermined path profile.

Example 22

The robotic surgical system of Example 21, wherein selection of the second predetermined path is configured to prevent the actuation body from accessing the first predetermined path.

Example 23

A method operating a surgical instrument of a robotic surgical system, wherein the robotic surgical system includes a robotic arm, and a surgical instrument configured removably coupled with the robotic arm, wherein the surgical instrument includes an end effector, a shaft assembly extending proximally from the end effector, wherein the shaft assembly defines a longitudinal axis, a drive operatively connected to a portion of at least one of the end effector or the shaft assembly, and an activating mechanism, wherein the activating mechanism includes an actuation body operatively connected to the drive, the method comprising: (a) moving the actuation body along a first predetermined path to manually apply a buttress to the end effector while preventing robotic operation of the end effector; and (b) moving the actuation body along a second predetermined path to robotically operate the end effector of the surgical instrument of the robotic surgical system.

Example 24

The method of Example 23, further comprising shifting the actuation body from the first predetermined path to the second predetermined path to allow for robotic operation of the end effector.

Example 25

The method of any one or more of Examples 23 through 24, wherein moving the actuation body along the first predetermined path further comprises rotating the actuation body in a first direction, wherein moving the actuation body along the second predetermined path further comprises rotating the actuation body in a second direction that is opposite to the first direction.

V. MISCELLANEOUS

Furthermore, any one or more of the teachings herein may be combined with any one or more of the teachings disclosed in U.S. patent application Ser. No. 17/245,332, entitled "Variable Jaw Closure of a Robotic Surgical System," filed Apr. 30, 2021, and issued as U.S. Pat. No. 11,937,892 on Mar. 26, 2024; U.S. patent application Ser. No. 17/245,340, entitled "Robotic Surgical System with an Articulation Lockout," filed Apr. 30, 2021, and published as U.S. Pat. Pub. No. 2022/0346891 on Nov. 3, 2022, now abandoned; U.S. patent application Ser. No. 17/245,351, entitled "Multi-Zone Jaw Closure of a Robotic Surgical System," filed Apr. 30, 2021, and published as U.S. Pat. Pub. No. 2022/0346898 on Nov. 3, 2022, now abandoned; and U.S. patent application Ser. No. 17/245,100, entitled "Translatable Barrel Cam of a Robotic Surgical System," filed Apr. 30, 2021, and issued as U.S. Pat. No. 11,607,218 on Mar. 21, 2023. The disclosure of each of these patent applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector comprising:
      (i) a first jaw, and
      (ii) a second jaw, wherein at least one of the first and second jaws is pivotable relative to the other of the first and second jaws between an open position and a closed position;
   (b) a shaft assembly extending proximally from the end effector, wherein the shaft assembly defines a longitudinal axis;
   (c) a drive operatively connected to a portion of at least one of the end effector or the shaft assembly; and
   (d) an activating mechanism including an actuation body operatively connected to the drive, wherein the portion is configured to perform a first actuation profile in response to the actuation body moving along a first predetermined path or perform a second actuation profile in response to the actuation body moving along a second predetermined path, wherein selection of the first predetermined path is configured to prevent the actuation body from accessing the second predetermined path,
   wherein the activating mechanism further includes a translational driver, wherein the translational driver is engaged with the actuation body and configured to selectively translate the actuation body from a first translational body position toward a second translational body position.

2. The surgical instrument of claim 1, wherein selection of the second predetermined path is configured to prevent the actuation body from accessing the first predetermined path.

3. The surgical instrument of claim 1, wherein the drive includes a follower, wherein the actuation body includes a cam slot, and wherein the follower is configured to be received within the cam slot such that the cam slot guides movement of the follower as the actuation body moves along the first or second predetermined paths.

4. The surgical instrument of claim 3, wherein the actuation body includes a barrel cam having the cam slot that forms the first and second predetermined paths, wherein the barrel cam extends parallel to the longitudinal axis and configured to selectively rotate about the longitudinal axis, and wherein the barrel cam is further configured to selectively translate along the longitudinal axis.

5. The surgical instrument of claim 4, wherein the first and second predetermined paths collectively extend continuously around an entire circumference of the barrel cam.

6. The surgical instrument of claim 4, further comprising a housing that includes a first projection, wherein the barrel cam includes a second projection that is configured to selectively contact the first projection as at least one of the first or second projections rotates relative to the other of the first or second projections.

7. The surgical instrument of claim 6, wherein the second projection extends outwardly from an outer surface of the barrel cam.

8. The surgical instrument of claim 4, further comprising an actuator configured to move one of the first or second projections between a blocking configuration and a non-blocking configuration, wherein the second projection is configured to contact the first projection in the blocking configuration, and wherein the second projection is configured to not contact the first projection in the non-blocking configuration.

9. The surgical instrument of claim 1, further comprising a shifting mechanism configured to direct the actuation body between the first and second predetermined paths.

10. The surgical instrument of claim 9, further comprising a hard stop interposed between the first and second predetermined paths and configured to be overcome by activating the shifting mechanism.

11. The surgical instrument of claim 9, wherein the shifting mechanism includes a longitudinally extending portion extending parallel to the longitudinal axis, wherein a longitudinal slot connects the first and second predetermined paths.

12. The surgical instrument of claim 9, wherein the surgical instrument comprises a housing and a carriage configured to move along the housing, wherein the shifting mechanism includes a wedge configured to move between disengaged and engaged positions and thereby adjust the actuation body between the first and second predetermined paths, wherein in the disengaged position the actuation body is configured to travel along the first predetermined path, wherein in the engaged position the actuation body is configured to travel along the second predetermined path.

13. The surgical instrument of claim 12, wherein the wedge includes a thin forked portion, a thick forked portion and a ramp, wherein the ramp is configured to engage the housing in the engaged position when the carriage is in a first position, wherein the ramp is configured to not engage the housing in the disengaged position when the carriage is in second position and the first predetermined path.

14. The surgical instrument of claim 1, wherein the surgical instrument includes a robotic arm, wherein the first actuation profile is configured to apply a buttress to at least one of the first and second jaws of the end effector, wherein the second actuation profile is configured to clamp tissue between the first and second jaws of the end effector.

15. A surgical instrument, comprising:
   (a) an end effector comprising:
   (b) a shaft assembly extending proximally from the end effector, wherein the shaft assembly defines a longitudinal axis;
   (c) a drive operatively connected to a portion of at least one of the end effector or the shaft assembly, wherein the drive includes a follower; and
   (d) an activating mechanism including an actuation body having a cam slot that receives the follower such that the cam slot guides movement of the follower as the actuation body moves along a first predetermined path or a second predetermined path, wherein the portion is configured to perform a first actuation profile in response to the actuation body moving along the first predetermined path or perform a second actuation profile in response to the actuation body moving along the second predetermined path, wherein selection of the first predetermined path is configured to prevent the actuation body from accessing the second predetermined path, wherein the actuation body includes a barrel cam having the cam slot that forms the first and second predetermined paths.

16. The surgical instrument of claim 15, wherein the barrel cam extends parallel to the longitudinal axis and configured to selectively rotate about the longitudinal axis, and wherein the barrel cam is further configured to selectively translate along the longitudinal axis.

17. The surgical instrument of claim 15, wherein the end effector includes:
(i) a first jaw, and
(ii) a second jaw, wherein at least one of the first and second jaws is pivotable relative to the other of the first and second jaws between an open position and a closed position.

18. A surgical instrument, comprising:
(a) an end effector comprising:
(b) a shaft assembly extending proximally from the end effector, wherein the shaft assembly defines a longitudinal axis;
(c) a drive operatively connected to a portion of at least one of the end effector or the shaft assembly;
(d) an activating mechanism including an actuation body operatively connected to the drive, wherein the portion is configured to perform a first actuation profile in response to the actuation body moving along a first predetermined path or perform a second actuation profile in response to the actuation body moving along a second predetermined path, wherein selection of the first predetermined path is configured to prevent the actuation body from accessing the second predetermined path; and
(e) a shifting mechanism configured to direct the actuation body between the first and second predetermined paths wherein the shifting mechanism includes a wedge configured to move between first and second positions and thereby adjust the actuation body between the first and second predetermined paths.

19. The surgical instrument of claim 18, wherein in the first position the actuation body is configured to travel along the first predetermined path, wherein in the second position the actuation body is configured to travel along the second predetermined path.

20. The surgical instrument of claim 19, wherein the surgical instrument comprises a housing and a carriage configured to move along the housing.

* * * * *